US010961499B2

(12) United States Patent
Corre et al.

(10) Patent No.: US 10,961,499 B2
(45) Date of Patent: Mar. 30, 2021

(54) METHOD FOR THE FERMENTATIVE PRODUCTION OF MOLECULES OF INTEREST BY MICROORGANISMS COMPRISING GENES CODING SUGAR PHOSPHOTRANSFERASE SYSTEM (PTS)

(71) Applicant: METABOLIC EXPLORER, Saint Beauzire (FR)

(72) Inventors: Gwénaëlle Corre, Saint Beauzire (FR); Céline Raynaud, Saint Beauzire (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 16/315,977

(22) PCT Filed: Jul. 6, 2017

(86) PCT No.: PCT/EP2017/067025

§ 371 (c)(1),
(2) Date: Jan. 7, 2019

(87) PCT Pub. No.: WO2018/007560

PCT Pub. Date: Jan. 11, 2018

(65) Prior Publication Data

US 2019/0276794 A1 Sep. 12, 2019

(30) Foreign Application Priority Data

Jul. 8, 2016 (WO) .................. PCT/IB2016/001123

(51) Int. Cl.

| | |
|---|---|
| ***C12N 15/70*** | (2006.01) |
| ***C12N 1/20*** | (2006.01) |
| ***C12N 1/16*** | (2006.01) |
| ***C12N 9/12*** | (2006.01) |
| ***C07K 14/245*** | (2006.01) |
| ***C12P 7/18*** | (2006.01) |
| ***C12P 7/42*** | (2006.01) |
| ***C12R 1/19*** | (2006.01) |
| ***C12P 7/06*** | (2006.01) |
| ***C12N 9/00*** | (2006.01) |

(52) U.S. Cl.

CPC .............. *C12N 1/20* (2013.01); *C07K 14/245* (2013.01); *C12N 1/16* (2013.01); *C12N 9/00* (2013.01); *C12N 9/1294* (2013.01); *C12N 15/70* (2013.01); *C12P 7/06* (2013.01); *C12P 7/18* (2013.01); *C12P 7/42* (2013.01); *C12R 1/19* (2013.01); *C12N 9/1205* (2013.01); *C12Y 207/09002* (2013.01); *Y02E 50/10* (2013.01)

(58) Field of Classification Search

CPC .................. C07K 14/245; C12N 15/70; C12Y 207/09002; C12Y 207/11033

See application file for complete search history.

(56) References Cited

U.S. PATENT DOCUMENTS

2003/0219798 A1* 11/2003 Gokarn .................. C12P 23/00 435/6.13

FOREIGN PATENT DOCUMENTS

| | | | |
|---|---|---|---|
| DE | 10130192 | A1 | 4/2002 |
| RU | 2 461 627 | C2 | 12/2010 |
| WO | WO 02/22829 | A2 | 3/2002 |
| WO | WO 02/29080 | A2 | 4/2002 |
| WO | WO 03/040373 | A2 | 5/2003 |
| WO | WO 2008/052596 | A1 | 12/2010 |
| WO | 2015177800 | * | 11/2015 |
| WO | WO 2016/050959 | A2 | 4/2016 |

OTHER PUBLICATIONS

Burnell. 2010; Cloning and characterization of *Escherichia coli* DUF299: a bifunctional ADP-dependent kinase-Pi-dependent pyrophosphorylase from bacteria. BMC Biochemistry. 11(1): 1-8.*

Hermann-Krauss et al. 2013; Archaeal production of polyhydroxyalkanoate (PHA) co- and terpolyesters from biodiesel industry-derived by-products. Archaea. vol. 2013, pp. 1-10.*

Trinh et al. 2008; Minimal *Escherichi coli* cell for the most efficient production of ethanol from hexoses and pentoses. Applied and Environmental Microbiology. 74(12): 3634-3643.*

Altaras et al., "Metabolic Engineering of a 1,2-Propanediol Pathway in *Escherichia coli*," Applied and Environmental Microbiology, vol. 65, No. 3, Mar. 1999, pp. 1180-1185.

Altschul et al., "Basic Local Alignment Search Tool," J. Mol. Biol., vol. 215, 1990, pp. 403-410.

Anderson, "Growth Requirements of Virus-Resistant Mutants of *Escherichia coli* Strain "B"," Proc. N.A.S., vol. 32, 1946, pp. 120-128.

Antonovsky et al., "Sugar Synthesis from $CO_2$ in *Escherichia coli*," Cell, vol. 166, Jun. 30, 2016, pp. 115-125 (12 pages total).

Burnell et al., "Cloning and Characterization of *Escherichia coli* DUF299: A Bifunctional ADP-dependent Kinase—$P_i$-dependent Pyrophosphorylase from Bacteria," BMC Biochemistry, vol. 11, No. 1, 2010 (Published Jan. 3, 2010), pp. 1-8.

Canovas et al., "Fine Control of Phosphopyruvate Carboxylase Activity in *Escherichia coli*," Biochim Biophys Acta, vol. 96, 1965, pp. 169-172.

(Continued)

*Primary Examiner* — Karen Cochrane Carlson

(74) *Attorney, Agent, or Firm* — Birch, Stewart, Kolasch & Birch, LLP

(57) ABSTRACT

The present invention relates to a new method for the production of a molecule of interest by conversion of a source of carbon in a fermentative process comprising culturing a microorganism genetically modified for the production of molecule of interest, wherein said microorganism comprises functional genes coding PTS carbohydrate utilization system and wherein the expression of proteins regulated the expression of phosphoenolpyruvate synthase (PPS) is down-regulated. The present invention also relates to the genetically modified microorganism used in the method of the invention.

11 Claims, No Drawings

Specification includes a Sequence Listing.

(56) References Cited

OTHER PUBLICATIONS

Cooper et al., "Net Formation of Phosphoenolpyruvate from Pyruvate by *Escherichia coli*," Biochim Biophys Acta, vol. 104, 1965, pp. 618-620.

Datsenko et al., "One-step Inactivation of Chromosomal Genes in *Escherichia coli* K-12 Using PCR Products," PNAS, vol. 97, No. 12, Jun. 6, 2000, pp. 6640-6645.

Davis et al., "Characterizing the Native Codon Usages of a Genome: An Axis Projection Approach," Mol. Biol. Evol., vol. 28, No. 1, 2011 (Advance Access publication, Aug. 2, 2010), pp. 211-221.

Deml et al., "Multiple Effects of Codon Usage Optimization on Expression and Immunogenicity of DNA Candidate Vaccines Encoding the Human Immunodeficiency Virus Type 1 Gag Protein," Journal of Virology, vol. 75, No. 22, Nov. 2001, pp. 10991-11001.

Gabor et al., "The Phosphoenolpyruvate-dependent Glucose-phosphotransferase System from *Escherichia coli* K-12 as the Center of a Network Regulating Carbohydrate Flux in the Cell," European Journal of Cell Biology, vol. 90, 2011, pp. 711-720.

Gosset et al., "A Direct Comparison of Approaches for Increasing Carbon Flow to Aromatic Biosynthesis in *Escherichia coli*," Journal of Industrial Microbiology, vol. 17, 1996, pp. 47-52.

Graf et al., "Concerted Action of Multiple cis-Acting Sequences Is Required for Rev Dependence of Late Human Immunodeficiency Virus Type 1 Gene Expression," Journal of Virology, vol. 74, No. 22, Nov. 2000, pp. 10822-10826.

Hanai et al., "Engineered Synthetic Pathway for Isopropanol Production in *Escherichia coli*," Applied and Environmental Microbiology, vol. 73, No. 24, Dec. 2007 (Published ahead of print on Oct. 12, 2007), pp. 7814-7818.

Jung et al., "Enhanced Production of 1,2-Propanediol by tpi1 Deletion in *Saccharomyces cerevisiae*," J. Microbiol. Biotechnol., vol. 18, No. 11, 2008 (First published online Aug. 4, 2008), pp. 1797-1802.

Kim et al., "Effect of Overexpression of Actinobacillus succinogenes Phosphoenolpyruvate Carboxykinase on Succinate Production in *Escherichia coli*," Applied and Environmental Microbiology, vol. 70, No. 2, Feb. 2004, pp. 1238-1241.

Kornberg et al., "Control In Situ of the Pyruvate kinase Activity of *Escherichia coli*," FEBS Letters, vol. 32, No. 2, Jun. 1973, pp. 257-259.

Kotrba et al., "Bacterial Phosphotransferase System (PTS) in Carbohydrate Uptake and Control of Carbon Metabolism," Journal of Bioscience and Bioengineering, vol. 92, No. 6, 2001, pp. 502-517.

Meza et al., "Consequences of Phosphoenolpyruvate:Sugar Phosphotranferase System and Pyruvate Kinase Isozymes Inactivation in Central Carbon Metabolism Flux Distribution in *Escherichia coli*," Microbial Cell Factories, vol. 11, No. 127, 2012, pp. 1-13.

Patnaik et al. "Stimulation of Glucose Catabolism in *Escherichia coli* by a Potential Futile Cycle," Journal of Bacteriology, vol. 174, No. 23, Dec. 1992, pp. 7527-7532.

Pittard et al., "Distribution and Function of Genes Concerned with Aromatic Biosynthesis in *Escherichia coli*," Journal of Bacteriology, vol. 91, No. 4, Apr. 1966, pp. 1494-1508.

Postma et al., "The Bacterial Phosphoenolpyruvate:Sugar Phosphotransferase System," Biochimica et Biophysica Acta, vol. 457, 1976, pp. 213-257.

Schaefer et al., "Automated Sampling Device for Monitoring Intracellular Metabolite Dynamics," Analytical Biochemistry, vol. 270, 1999, pp. 88-96.

Schmid et al., "Plasmid-Mediated Uptake and Metabolism of Sucrose by *Escherichia coli* K-12," Journal of Bacteriology, vol. 151, No. 1, Jul. 1982, pp. 68-76.

Tatarko et al., "Disruption of a Global Regulatory Gene to Enhance Central Carbon Flux into Phenylalanine Biosynthesis in *Escherichia coli*," Current Microbiology, vol. 43, 2001, pp. 26-32.

Tolentino et al., "Identification of the Amino Acid Involved in the Regulation of Bacterial Pyruvate, Orthophosphate Dikinase and Phosphoenolpyruvate Synthetase," Advances in Biological Chemistry, vol. 3, 2013 (Published Online Jun. 2013), pp. 12-21.

* cited by examiner

SEQUENCE LISTING

```
<160> NUMBER OF SEQ ID NOS: 132

<210> SEQ ID NO 1
<211> LENGTH: 834
<212> TYPE: DNA
<213> ORGANISM: Escherichia coli

<400> SEQUENCE: 1

atggataatg ctgttgatcg ccacgttttt tatatttctg atggtacggc aataactgcg      60

gaggtattag gacacgcagt aatgtcacaa tttcccgtca ctatcagcag catcacgctg     120

ccgtttgtcg aaaatgagag ccgtgcacgg gcagtgaagg atcagattga cgcaatttat     180

caccagacag gcgtgcgccc gctggtcttc tactccatcg tgttgccgga gattcgcgcc     240

atcatcttgc aaagtgaagg ctttttgccag gatatcgttc aggcgctggt tgccccgcta     300

caacaagaga tgaaactgga tccaacgccg attgctcatc gtacccatgg ccttaaccct     360

aataatctca ataaatatga tgcgcgcatt gcggcgattg attacaccct cgcccacgat     420

gacggcattt cgttgcgcaa tctggaccag gctcaggtga tcctgctcgg tgtttctcgc     480

tgtggtaaaa cccccaccag tctgtatctg gcaatgcagt ttggtatccg cgcggcaaac     540

taccccttta ttgccgacga tatggataat ctggtgctac ccgcgtcgct caaaccgctt     600

cagcataaat tgttcggcct gactatcgac ccggaacgtc tggcggcgat tcgcgaggaa     660

cgtcgggaga acagtcgcta tgcctcgctt cgtcagtgca ggatggaagt cgcggaagtg     720
```

-continued

```
gaagccttgt accgtaaaaa tcagatcccg tggattaaca gtaccaatta ttcggtagaa    780

gagattgcca ccaagatcct cgatatcatg ggccttagtc gccgaatgta ctag          834


<210> SEQ ID NO 2
<211> LENGTH: 277
<212> TYPE: PRT
<213> ORGANISM: Escherichia coli

<400> SEQUENCE: 2

Met Asp Asn Ala Val Asp Arg His Val Phe Tyr Ile Ser Asp Gly Thr
1               5                   10                  15

Ala Ile Thr Ala Glu Val Leu Gly His Ala Val Met Ser Gln Phe Pro
            20                  25                  30

Val Thr Ile Ser Ser Ile Thr Leu Pro Phe Val Glu Asn Glu Ser Arg
        35                  40                  45

Ala Arg Ala Val Lys Asp Gln Ile Asp Ala Ile Tyr His Gln Thr Gly
    50                  55                  60

Val Arg Pro Leu Val Phe Tyr Ser Ile Val Leu Pro Glu Ile Arg Ala
65                  70                  75                  80

Ile Ile Leu Gln Ser Glu Gly Phe Cys Gln Asp Ile Val Gln Ala Leu
                85                  90                  95

Val Ala Pro Leu Gln Gln Glu Met Lys Leu Asp Pro Thr Pro Ile Ala
            100                 105                 110

His Arg Thr His Gly Leu Asn Pro Asn Asn Leu Asn Lys Tyr Asp Ala
        115                 120                 125

Arg Ile Ala Ala Ile Asp Tyr Thr Leu Ala His Asp Asp Gly Ile Ser
    130                 135                 140

Leu Arg Asn Leu Asp Gln Ala Gln Val Ile Leu Leu Gly Val Ser Arg
145                 150                 155                 160

Cys Gly Lys Thr Pro Thr Ser Leu Tyr Leu Ala Met Gln Phe Gly Ile
                165                 170                 175

Arg Ala Ala Asn Tyr Pro Phe Ile Ala Asp Asp Met Asp Asn Leu Val
            180                 185                 190

Leu Pro Ala Ser Leu Lys Pro Leu Gln His Lys Leu Phe Gly Leu Thr
        195                 200                 205

Ile Asp Pro Glu Arg Leu Ala Ala Ile Arg Glu Glu Arg Arg Glu Asn
    210                 215                 220

Ser Arg Tyr Ala Ser Leu Arg Gln Cys Arg Met Glu Val Ala Glu Val
225                 230                 235                 240

Glu Ala Leu Tyr Arg Lys Asn Gln Ile Pro Trp Ile Asn Ser Thr Asn
                245                 250                 255

Tyr Ser Val Glu Glu Ile Ala Thr Lys Ile Leu Asp Ile Met Gly Leu
            260                 265                 270

Ser Arg Arg Met Tyr
        275


<210> SEQ ID NO 3
<211> LENGTH: 459
<212> TYPE: DNA
<213> ORGANISM: Escherichia coli

<400> SEQUENCE: 3

atggaactga cgactcgcac tttacctgcg cggaaacata ttgcgctggt ggcacacgat     60

cactgcaaac aaatgctgat gagctgggtg gaacggcatc aaccgttact ggaacaacac    120

gtactgtatg caacaggcac taccggtaac ttaatttccc gcgcgaccgg catgaacgtc    180
```

-continued aacgcgatgt tgagtggccc aatggggggt gaccagcagg ttggcgcatt gatctcagaa 240
gggaaaattg atgtattgat ttcttctgg gatccactaa atgccgtgcc gcacgatcct 300
gacgtgaaag ccttgctgcg tctggcgacg gtatggaaca ttccggtcgc caccaacgtg 360
gcaacggcag acttcataat ccagtcgccg catttcaacg acgcggtcga tattctgatc 420
cccgattatc agcgttatct cgcggaccgt ctgaagtaa 459

<210> SEQ ID NO 4
<211> LENGTH: 152
<212> TYPE: PRT
<213> ORGANISM: Escherichia coli

<400> SEQUENCE: 4

Met Glu Leu Thr Thr Arg Thr Leu Pro Ala Arg Lys His Ile Ala Leu
1 5 10 15

Val Ala His Asp His Cys Lys Gln Met Leu Met Ser Trp Val Glu Arg
20 25 30

His Gln Pro Leu Leu Glu Gln His Val Leu Tyr Ala Thr Gly Thr Thr
35 40 45

Gly Asn Leu Ile Ser Arg Ala Thr Gly Met Asn Val Asn Ala Met Leu
50 55 60

Ser Gly Pro Met Gly Gly Asp Gln Gln Val Gly Ala Leu Ile Ser Glu
65 70 75 80

Gly Lys Ile Asp Val Leu Ile Phe Phe Trp Asp Pro Leu Asn Ala Val
85 90 95

Pro His Asp Pro Asp Val Lys Ala Leu Leu Arg Leu Ala Thr Val Trp
100 105 110

Asn Ile Pro Val Ala Thr Asn Val Ala Thr Ala Asp Phe Ile Ile Gln
115 120 125

Ser Pro His Phe Asn Asp Ala Val Asp Ile Leu Ile Pro Asp Tyr Gln
130 135 140

Arg Tyr Leu Ala Asp Arg Leu Lys
145 150

<210> SEQ ID NO 5
<211> LENGTH: 459
<212> TYPE: DNA
<213> ORGANISM: artificial
<220> FEATURE:
<223> OTHER INFORMATION: mgsA* gene

<400> SEQUENCE: 5
atggaactga cgactcgcac tttacctgcg cggaaacata ttgcgctggt ggcacacgat 60
caatgcaaac agatgctgat gagctgggtg gaacggcatc aaccgttact ggaacaacac 120
gtactgtatg caacaggcac taccggtaac ttaatttccc gcgcgaccgg catgaacgtc 180
aacgcgatgt tgagtggccc aatggggggt gaccagcagg ttggcgcatt gatctcagaa 240
gggaaaattg atgtattgat ttcttctgg gatccactaa atgccgtgcc gcacgatcct 300
gacgtgaaag ccttgctgcg tctggcgacg gtatggaaca ttccggtcgc caccaacgtg 360
gcaacggcag acttcataat ccagtcgccg catttcaacg acgcggtcga tattctgatc 420
cccgattatc agcgttatct cgcggaccgt ctgaagtaa 459

<210> SEQ ID NO 6
<211> LENGTH: 152
<212> TYPE: PRT

<213> ORGANISM: artificial
<220> FEATURE:
<223> OTHER INFORMATION: mgsA* prot

<400> SEQUENCE: 6

Met Glu Leu Thr Thr Arg Thr Leu Pro Ala Arg Lys His Ile Ala Leu
1 5 10 15

Val Ala His Asp Gln Cys Lys Gln Met Leu Met Ser Trp Val Glu Arg
20 25 30

His Gln Pro Leu Leu Glu Gln His Val Leu Tyr Ala Thr Gly Thr Thr
35 40 45

Gly Asn Leu Ile Ser Arg Ala Thr Gly Met Asn Val Asn Ala Met Leu
50 55 60

Ser Gly Pro Met Gly Gly Asp Gln Gln Val Gly Ala Leu Ile Ser Glu
65 70 75 80

Gly Lys Ile Asp Val Leu Ile Phe Phe Trp Asp Pro Leu Asn Ala Val
85 90 95

Pro His Asp Pro Asp Val Lys Ala Leu Leu Arg Leu Ala Thr Val Trp
100 105 110

Asn Ile Pro Val Ala Thr Asn Val Ala Thr Ala Asp Phe Ile Ile Gln
115 120 125

Ser Pro His Phe Asn Asp Ala Val Asp Ile Leu Ile Pro Asp Tyr Gln
130 135 140

Arg Tyr Leu Ala Asp Arg Leu Lys
145 150

<210> SEQ ID NO 7
<211> LENGTH: 1164
<212> TYPE: DNA
<213> ORGANISM: Escherichia coli

<400> SEQUENCE: 7
atgaacaact ttaatctgca caccccaacc cgcattctgt ttggtaaagg cgcaatcgct 60
ggtttacgcg aacaaattcc tcacgatgct cgcgtattga ttacctacgg cggcggcagc 120
gtgaaaaaaa ccggcgttct cgatcaagtt ctggatgccc tgaaaggcat ggacgtgctg 180
gaatttggcg gtattgagcc aaacccggct tatgaaacgc tgatgaacgc cgtgaaactg 240
gttcgcgaac agaaagtgac tttcctgctg gcggttggcg gcggttctgt actggacggc 300
accaaattta tcgccgcagc ggctaactat ccggaaaata tcgatccgtg gcacattctg 360
caaacgggcg gtaaagagat taaaagcgcc atcccgatgg gctgtgtgct gacgctgcca 420
gcaaccggtt cagaatccaa cgcaggcgcg gtgatctccc gtaaaaccac aggcgacaag 480
caggcgttcc attctgccca tgttcagccg gtatttgccg tgctcgatcc ggtttatacc 540
tacaccctgc cgccgcgtca ggtggctaac ggcgtagtgg acgcctttgt acacaccgtg 600
gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080

-continued gaagagcacg gcatgaccca actgggcgaa aatcatgaca ttacgttgga tgtcagccgc 1140
cgtatatacg aagccgcccg ctaa 1164

<210> SEQ ID NO 8
<211> LENGTH: 387
<212> TYPE: PRT
<213> ORGANISM: Escherichia coli

<400> SEQUENCE: 8

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350
```

-continued

```
Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 9
<211> LENGTH: 804
<212> TYPE: DNA
<213> ORGANISM: Escherichia coli

<400> SEQUENCE: 9

atggctatcc ctgcatttgg tttaggtact ttccgtctga aagacgacgt tgttatttca      60

tctgtgataa cggcgcttga acttggttat cgcgcaattg ataccgcaca aatctatgat     120

aacgaagccg cagtaggtca ggcgattgca gaaagtggcg tgccacgtca tgaactctac     180

atcaccacta aaatctggat tgaaaatctc agcaaagaca aattgatccc aagtctgaaa     240

gagagcctgc aaaaattgcg taccgattat gttgatctga cgctaatcca ctggccgtca     300

ccaaacgatg aagtctctgt tgaagagttt atgcaggcgc tgctggaagc caaaaaacaa     360

gggctgacgc gtgagatcgg tatttccaac ttcacgatcc cgttgatgga aaaagcgatt     420

gctgctgttg gtgctgaaaa catcgctact aaccagattg aactctctcc ttatctgcaa     480

aaccgtaaag tggttgcctg ggctaaacag cacggcatcc atattacttc ctatatgacg     540

ctggcgtatg gtaaggccct gaaagatgag gttattgctc gtatcgcagc taaacacaat     600

gcgactccgg cacaagtgat tctggcgtgg gctatggggg aaggttactc agtaattcct     660

tcttctacta aacgtaaaaa cctggaaagt aatcttaagg cacaaaattt acagcttgat     720

gccgaagata aaaaagcgat cgccgcactg gattgcaacg accgcctggt tagcccggaa     780

ggtctggctc ctgaatggga ttaa                                            804


<210> SEQ ID NO 10
<211> LENGTH: 267
<212> TYPE: PRT
<213> ORGANISM: Escherichia coli

<400> SEQUENCE: 10

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45

Ile Ala Glu Ser Gly Val Pro Arg His Glu Leu Tyr Ile Thr Thr Lys
    50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140
```

-continued

```
Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265
```

<210> SEQ ID NO 11
<211> LENGTH: 1050
<212> TYPE: DNA
<213> ORGANISM: Escherichia coli

<400> SEQUENCE: 11

```
atgaagatca aagctgttgg tgcatattcc gctaaacaac cacttgaacc gatggatatc     60

acccggcgtg aaccgggacc gaatgatgtc aaaatcgaaa tcgcttactg tggcgtttgc    120

cattccgatc tccaccaggt ccgttccgag tgggcgggga cggtttaccc ctgcgtgccg    180

ggtcatgaaa ttgtggggcg tgtggtagcc gttggtgatc aggtagaaaa atatgcgccg    240

ggcgatctgg tcggtgtcgg ctgcattgtc gacagttgta aacattgcga agagtgtgaa    300

gacgggttgg aaaactactg tgatcacatg accggcacct ataactcgcc gacgccggac    360

gaaccgggcc atactctggg cggctactca caacagatcg tcgttcatga gcgatatgtt    420

ctgcgtattc gtcacccgca agagcagctg gcggcggtgg ctcctttgtt gtgtgcaggg    480

atcaccacgt attcgccgct acgtcactgg caggccgggc cgggtaaaaa agtgggcgtg    540

gtcggcatcg gcggtctggg acatatgggg attaagctgg cccacgcgat gggggcacat    600

gtggtggcat ttaccacttc tgaggcaaaa cgcgaagcgg caaaagccct gggggccgat    660

gaagttgtta actcacgcaa tgccgatgag atggcggctc atctgaagag tttcgatttc    720

attttgaata cagtagctgc gccacataat ctcgacgatt ttaccacctt gctgaagcgt    780

gatggcacca tgacgctggt tggtgcgcct gcgacaccgc ataaatcgcc ggaagttttc    840

aacctgatca tgaaacgccg tgcgatagcc ggttctatga ttggcggcat tccagaaact    900

caggagatgc tcgatttttg cgccgaacat ggcatcgtgg ctgatataga gatgattcgg    960

gccgatcaaa ttaatgaagc ctatgagcga atgctgcgcg gtgatgtgaa atatcgtttt   1020

gttatcgata atcgcacact aacagactga                                    1050
```

<210> SEQ ID NO 12
<211> LENGTH: 349
<212> TYPE: PRT
<213> ORGANISM: Escherichia coli

<400> SEQUENCE: 12

```
Met Lys Ile Lys Ala Val Gly Ala Tyr Ser Ala Lys Gln Pro Leu Glu
1               5                   10                  15
```

-continued

```
Pro Met Asp Ile Thr Arg Arg Glu Pro Gly Pro Asn Asp Val Lys Ile
            20                  25                  30

Glu Ile Ala Tyr Cys Gly Val Cys His Ser Asp Leu His Gln Val Arg
        35                  40                  45

Ser Glu Trp Ala Gly Thr Val Tyr Pro Cys Val Pro Gly His Glu Ile
    50                  55                  60

Val Gly Arg Val Val Ala Val Gly Asp Gln Val Glu Lys Tyr Ala Pro
65                  70                  75                  80

Gly Asp Leu Val Gly Val Gly Cys Ile Val Asp Ser Cys Lys His Cys
                85                  90                  95

Glu Glu Cys Glu Asp Gly Leu Glu Asn Tyr Cys Asp His Met Thr Gly
            100                 105                 110

Thr Tyr Asn Ser Pro Thr Pro Asp Glu Pro Gly His Thr Leu Gly Gly
        115                 120                 125

Tyr Ser Gln Gln Ile Val Val His Glu Arg Tyr Val Leu Arg Ile Arg
    130                 135                 140

His Pro Gln Glu Gln Leu Ala Ala Val Ala Pro Leu Leu Cys Ala Gly
145                 150                 155                 160

Ile Thr Thr Tyr Ser Pro Leu Arg His Trp Gln Ala Gly Pro Gly Lys
                165                 170                 175

Lys Val Gly Val Val Gly Ile Gly Gly Leu Gly His Met Gly Ile Lys
            180                 185                 190

Leu Ala His Ala Met Gly Ala His Val Val Ala Phe Thr Thr Ser Glu
        195                 200                 205

Ala Lys Arg Glu Ala Ala Lys Ala Leu Gly Ala Asp Glu Val Val Asn
    210                 215                 220

Ser Arg Asn Ala Asp Glu Met Ala Ala His Leu Lys Ser Phe Asp Phe
225                 230                 235                 240

Ile Leu Asn Thr Val Ala Ala Pro His Asn Leu Asp Asp Phe Thr Thr
                245                 250                 255

Leu Leu Lys Arg Asp Gly Thr Met Thr Leu Val Gly Ala Pro Ala Thr
            260                 265                 270

Pro His Lys Ser Pro Glu Val Phe Asn Leu Ile Met Lys Arg Arg Ala
        275                 280                 285

Ile Ala Gly Ser Met Ile Gly Gly Ile Pro Glu Thr Gln Glu Met Leu
    290                 295                 300

Asp Phe Cys Ala Glu His Gly Ile Val Ala Asp Ile Glu Met Ile Arg
305                 310                 315                 320

Ala Asp Gln Ile Asn Glu Ala Tyr Glu Arg Met Leu Arg Gly Asp Val
                325                 330                 335

Lys Tyr Arg Phe Val Ile Asp Asn Arg Thr Leu Thr Asp
            340                 345
```

```
<210> SEQ ID NO 13
<211> LENGTH: 1056
<212> TYPE: DNA
<213> ORGANISM: Clostridium beijerinckii

<400> SEQUENCE: 13

atgaaaggtt ttgcaatgct aggtattaat aagttaggat ggatcgaaaa agaaaggcca      60

gttgcgggtt catatgatgc tattgtacgc ccattagcag tatctccgtg tacatcagat     120

atacatactg tttttgaggg agctcttgga gataggaaga atatgatttt agggcatgaa     180

gctgtaggtg aagttgttga agtaggaagt gaagtgaagg attttaaacc tggtgacaga     240
```

gttatagttc cttgtacaac tccagattgg agatctttgg aagttcaagc tggttttcaa 300
cagcactcaa acggtatgct cgcaggatgg aaattttcaa atttcaagga tggagttttt 360
ggtgaatatt ttcatgtaaa tgatgcggat atgaatcttg cgattctacc taaagacatg 420
ccattagaaa atgctgttat gataacagat atgatgacta ctggatttca tggagcagaa 480
cttgcagata ttcaaatggg ttcaagtgtt gtggtaattg gcattggagc tgttggctta 540
atgggaatag caggtgctaa attacgtgga gcaggtagaa taattggagt ggggagcagg 600
ccgatttgtg ttgaggctgc aaaattttat ggagcaacag atattctaaa ttataaaaat 660
ggtcatatag ttgatcaagt tatgaaatta acgaatggaa aaggcgttga ccgcgtaatt 720
atggcaggcg gtggttctga aacattatcc caagcagtat ctatggttaa accaggagga 780
ataatttcta atataaatta tcatggaagt ggagatgctt tactaatacc acgtgtagaa 840
tggggatgtg gaatggctca caagactata aaaggaggtc tttgtcctgg gggacgtttg 900
agagcagaaa tgttaagaga tatggtagta tataatcgtg ttgatctaag taaattagtt 960
acacatgtat atcatggatt tgatcacata gaagaagcac tgttattaat gaaagacaag 1020
ccaaaagact taattaaagc agtagttata ttataa 1056

<210> SEQ ID NO 14
<211> LENGTH: 351
<212> TYPE: PRT
<213> ORGANISM: Clostridium beijerinckii

<400> SEQUENCE: 14

Met Lys Gly Phe Ala Met Leu Gly Ile Asn Lys Leu Gly Trp Ile Glu
1 5 10 15

Lys Glu Arg Pro Val Ala Gly Ser Tyr Asp Ala Ile Val Arg Pro Leu
20 25 30

Ala Val Ser Pro Cys Thr Ser Asp Ile His Thr Val Phe Glu Gly Ala
35 40 45

Leu Gly Asp Arg Lys Asn Met Ile Leu Gly His Glu Ala Val Gly Glu
50 55 60

Val Val Glu Val Gly Ser Glu Val Lys Asp Phe Lys Pro Gly Asp Arg
65 70 75 80

Val Ile Val Pro Cys Thr Thr Pro Asp Trp Arg Ser Leu Glu Val Gln
85 90 95

Ala Gly Phe Gln Gln His Ser Asn Gly Met Leu Ala Gly Trp Lys Phe
100 105 110

Ser Asn Phe Lys Asp Gly Val Phe Gly Glu Tyr Phe His Val Asn Asp
115 120 125

Ala Asp Met Asn Leu Ala Ile Leu Pro Lys Asp Met Pro Leu Glu Asn
130 135 140

Ala Val Met Ile Thr Asp Met Met Thr Thr Gly Phe His Gly Ala Glu
145 150 155 160

Leu Ala Asp Ile Gln Met Gly Ser Ser Val Val Val Ile Gly Ile Gly
165 170 175

Ala Val Gly Leu Met Gly Ile Ala Gly Ala Lys Leu Arg Gly Ala Gly
180 185 190

Arg Ile Ile Gly Val Gly Ser Arg Pro Ile Cys Val Glu Ala Ala Lys
195 200 205

Phe Tyr Gly Ala Thr Asp Ile Leu Asn Tyr Lys Asn Gly His Ile Val
210 215 220

-continued

```
Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350


<210> SEQ ID NO 15
<211> LENGTH: 1104
<212> TYPE: DNA
<213> ORGANISM: Escherichia coli

<400> SEQUENCE: 15

atggaccgca ttattcaatc accgggtaaa tacatccagg gcgctgatgt gattaatcgt      60

ctgggcgaat acctgaagcc gctggcagaa cgctggttag tggtgggtga caaatttgtt     120

ttaggttttg ctcaatccac tgtcgagaaa agctttaaag atgctggact ggtagtagaa     180

attgcgccgt ttggcggtga atgttcgcaa aatgagatcg accgtctgcg tggcatcgcg     240

gagactgcgc agtgtggcgc aattctcggt atcggtggcg gaaaaaccct cgatactgcc     300

aaagcactgg cacatttcat gggtgttccg gtagcgatcg caccgactat cgcctctacc     360

gatgcaccgt gcagcgcatt gtctgttatc tacaccgatg agggtgagtt tgaccgctat     420

ctgctgttgc caaataaccc gaatatggtc attgtcgaca ccaaaatcgt cgctggcgca     480

cctgcacgtc tgttagcggc gggtatcggc gatgcgctgg caacctggtt tgaagcgcgt     540

gcctgctctc gtagcggcgc gaccaccatg gcgggcggca agtgcaccca ggctgcgctg     600

gcactggctg aactgtgcta caacaccctg ctggaagaag gcgaaaaagc gatgcttgct     660

gccgaacagc atgtagtgac tccggcgctg gagcgcgtga ttgaagcgaa cacctatttg     720

agcggtgttg gttttgaaag tggtggtctg gctgcggcgc acgcagtgca taacggcctg     780

accgctatcc cggacgcgca tcactattat cacggtgaaa aagtggcatt cggtacgctg     840

acgcagctgg ttctggaaaa tgcgccggtg gaggaaatcg aaaccgtagc tgcccttagc     900

catgcggtag gtttgccaat aactctcgct caactggata ttaaagaaga tgtcccggcg     960

aaaatgcgaa ttgtggcaga agcggcatgt gcagaaggtg aaaccattca caacatgcct    1020

ggcggcgcga cgccagatca ggtttacgcc gctctgctgg tagccgacca gtacggtcag    1080

cgtttcctgc aagagtggga ataa                                           1104


<210> SEQ ID NO 16
<211> LENGTH: 367
<212> TYPE: PRT
<213> ORGANISM: Escherichia coli

<400> SEQUENCE: 16

Met Asp Arg Ile Ile Gln Ser Pro Gly Lys Tyr Ile Gln Gly Ala Asp
```

-continued

```
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365


<210> SEQ ID NO 17
<211> LENGTH: 408
<212> TYPE: DNA
<213> ORGANISM: Escherichia coli

<400> SEQUENCE: 17

atgcgtcttc ttcataccat gctgcgcgtt ggcgatttgc aacgctccat cgatttttat      60

accaaagtgc tgggcatgaa actgctgcgt accagcgaaa acccggaata caaatactca     120
```

-continued

```
ctggcgtttg ttggctacgg cccggaaacc gaagaagcgg tgattgaact gacctacaac    180

tggggcgtgg ataaatacga actcggcact gcttatggtc acatcgcgct tagcgtagat    240

aacgccgctg aagcgtgcga aaaaatccgt caaaacgggg gtaacgtgac ccgtgaagcg    300

ggtccggtaa aaggcggtac tacggttatc gcgtttgtgg aagatccgga cggttacaaa    360

attgagttaa tcgaagagaa agacgccggt cgcggtctgg gcaactaa                408
```

<210> SEQ ID NO 18
<211> LENGTH: 135
<212> TYPE: PRT
<213> ORGANISM: Escherichia coli

<400> SEQUENCE: 18

```
Met Arg Leu Leu His Thr Met Leu Arg Val Gly Asp Leu Gln Arg Ser
1               5                   10                  15

Ile Asp Phe Tyr Thr Lys Val Leu Gly Met Lys Leu Leu Arg Thr Ser
            20                  25                  30

Glu Asn Pro Glu Tyr Lys Tyr Ser Leu Ala Phe Val Gly Tyr Gly Pro
        35                  40                  45

Glu Thr Glu Glu Ala Val Ile Glu Leu Thr Tyr Asn Trp Gly Val Asp
    50                  55                  60

Lys Tyr Glu Leu Gly Thr Ala Tyr Gly His Ile Ala Leu Ser Val Asp
65                  70                  75                  80

Asn Ala Ala Glu Ala Cys Glu Lys Ile Arg Gln Asn Gly Gly Asn Val
                85                  90                  95

Thr Arg Glu Ala Gly Pro Val Lys Gly Gly Thr Thr Val Ile Ala Phe
            100                 105                 110

Val Glu Asp Pro Asp Gly Tyr Lys Ile Glu Leu Ile Glu Glu Lys Asp
        115                 120                 125

Ala Gly Arg Gly Leu Gly Asn
    130                 135
```

<210> SEQ ID NO 19
<211> LENGTH: 741
<212> TYPE: DNA
<213> ORGANISM: Escherichia coli

<400> SEQUENCE: 19

```
atgtcagtta ttggtcgcat tcactccttt gaatcctgtg gaaccgtaga cggcccaggt     60

attcgcttta tcaccttttt ccagggctgc ctgatgcgct gcctgtattg tcataaccgc    120

gacacctggg acacgcatgg cggtaaagaa gttaccgttg aagatttgat gaaggaagtg    180

gtgacctatc gccactttat gaacgcttcc ggcggcggcg ttaccgcatc cggcggtgaa    240

gcaatcctgc aagctgagtt tgttcgtgac tggttccgcg cctgcaaaaa agaaggcatt    300

catacctgtc tggacaccaa cggttttgtt cgtcgttacg atccggtgat tgatgaactg    360

ctggaagtaa ccgacctggt aatgctcgat ctcaaacaga tgaacgacga gatccaccaa    420

aatctggttg gagtttccaa ccaccgcacg ctggagttcg ctaaatatct ggcgaacaaa    480

aatgtgaagg tgtggatccg ctacgttgtt gtcccaggct ggtctgacga tgacgattca    540

gcgcatcgcc tcggtgaatt tacccgtgat atgggcaacg ttgagaaaat cgagcttctc    600

ccctaccacg agctgggcaa acacaaatgg gtggcaatgg gtgaagagta caaactcgac    660

ggtgttaaac caccgaagaa agagaccatg gaacgcgtga aaggcattct tgagcagtac    720

ggtcataagg taatgttcta a                                              741
```

<210> SEQ ID NO 20
<211> LENGTH: 246
<212> TYPE: PRT
<213> ORGANISM: Escherichia coli

<400> SEQUENCE: 20

```
Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30

Arg Cys Leu Tyr Cys His Asn Arg Asp Thr Trp Asp Thr His Gly Gly
        35                  40                  45

Lys Glu Val Thr Val Glu Asp Leu Met Lys Glu Val Val Thr Tyr Arg
    50                  55                  60

His Phe Met Asn Ala Ser Gly Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220

Pro Lys Lys Glu Thr Met Glu Arg Val Lys Gly Ile Leu Glu Gln Tyr
225                 230                 235                 240

Gly His Lys Val Met Phe
                245
```

<210> SEQ ID NO 21
<211> LENGTH: 2283
<212> TYPE: DNA
<213> ORGANISM: Escherichia coli

<400> SEQUENCE: 21

```
atgtccgagc ttaatgaaaa gttagccaca gcctgggaag gttttaccaa aggtgactgg      60

cagaatgaag taaacgtccg tgacttcatt cagaaaaact acactccgta cgagggtgac     120

gagtccttcc tggctggcgc tactgaagcg accaccaccc tgtgggacaa agtaatggaa     180

ggcgttaaac tggaaaaccg cactcacgcg ccagttgact ttgacaccgc tgttgcttcc     240

accatcacct ctcacgacgc tggctacatc aacaagcagc ttgagaaaat cgttggtctg     300

cagactgaag ctccgctgaa acgtgctctt atcccgttcg gtggtatcaa aatgatcgaa     360

ggttcctgca aagcgtacaa ccgcgaactg gatccgatga tcaaaaaaat cttcactgaa     420
```

-continued

```
taccgtaaaa ctcacaacca gggcgtgttc gacgtttaca ctccggacat cctgcgttgc    480

cgtaaatctg gtgttctgac cggtctgcca gatgcatatg gccgtggccg tatcatcggt    540

gactaccgtc gcgttgcgct gtacggtatc gactacctga tgaaagacaa actggcacag    600

ttcacttctc tgcaggctga tctggaaaac ggcgtaaacc tggaacagac tatccgtctg    660

cgcgaagaaa tcgctgaaca gcaccgcgct ctgggtcaga tgaaagaaat ggctgcgaaa    720

tacggctacg acatctctgg tccggctacc aacgctcagg aagctatcca gtggacttac    780

ttcggctacc tggctgctgt taagtctcag aacggtgctg caatgtcctt cggtcgtacc    840

tccaccttcc tggatgtgta catcgaacgt gacctgaaag ctggcaagat caccgaacaa    900

gaagcgcagg aaatggttga ccacctggtc atgaaactgc gtatggttcg cttcctgcgt    960

actccggaat acgatgaact gttctctggc gacccgatct gggcaaccga atctatcggt   1020

ggtatgggcc tcgacggtcg taccctggtt accaaaaaca gcttccgttt cctgaacacc   1080

ctgtacacca tgggtccgtc tccggaaccg aacatgacca ttctgtggtc tgaaaaactg   1140

ccgctgaact tcaagaaatt cgccgctaaa gtgtccatcg acacctcttc tctgcagtat   1200

gagaacgatg acctgatgcg tccggacttc aacaacgatg actacgctat tgcttgctgc   1260

gtaagcccga tgatcgttgg taaacaaatg cagttcttcg gtgcgcgtgc aaacctggcg   1320

aaaaccatgc tgtacgcaat caacggcggc gttgacgaaa aactgaaaat gcaggttggt   1380

ccgaagtctg aaccgatcaa aggcgatgtc ctgaactatg atgaagtgat ggagcgcatg   1440

gatcacttca tggactggct ggctaaacag tacatcactg cactgaacat catccactac   1500

atgcacgaca agtacagcta cgaagcctct ctgatggcgc tgcacgaccg tgacgttatc   1560

cgcaccatgg cgtgtggtat cgctggtctg tccgttgctg ctgactccct gtctgcaatc   1620

aaatatgcga aagttaaacc gattcgtgac gaagacggtc tggctatcga cttcgaaatc   1680

gaaggcgaat acccgcagtt tggtaacaat gatccgcgtg tagatgacct ggctgttgac   1740

ctggtagaac gtttcatgaa gaaaattcag aaactgcaca cctaccgtga cgctatcccg   1800

actcagtctg ttctgaccat cacttctaac gttgtgtatg gtaagaaaac gggtaacacc   1860

ccagacggtc gtcgtgctgg cgcgccgttc ggaccgggtg ctaacccgat gcacggtcgt   1920

gaccagaaag gtgcagtagc ctctctgact tccgttgcta aactgccgtt tgcttacgct   1980

aaagatggta tctcctacac cttctctatc gttccgaacg cactgggtaa agacgacgaa   2040

gttcgtaaga ccaacctggc tggtctgatg gatggttact tccaccacga agcatccatc   2100

gaaggtggtc agcacctgaa cgttaacgtg atgaaccgtg aaatgctgct cgacgcgatg   2160

gaaaacccgg aaaaatatcc gcagctgacc atccgtgtat ctggctacgc agtacgtttc   2220

aactcgctga ctaaagaaca gcagcaggac gttattactc gtaccttcac tcaatctatg   2280

taa                                                                 2283
```

<210> SEQ ID NO 22
<211> LENGTH: 760
<212> TYPE: PRT
<213> ORGANISM: Escherichia coli

<400> SEQUENCE: 22

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
```

```
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
            340                 345                 350

Asn Ser Phe Arg Phe Leu Asn Thr Leu Tyr Thr Met Gly Pro Ser Pro
        355                 360                 365

Glu Pro Asn Met Thr Ile Leu Trp Ser Glu Lys Leu Pro Leu Asn Phe
    370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460
```

```
Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
            500                 505                 510

Ala Leu His Asp Arg Asp Val Ile Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
            580                 585                 590

His Thr Tyr Arg Asp Ala Ile Pro Thr Gln Ser Val Leu Thr Ile Thr
        595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
                645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760
```

<210> SEQ ID NO 23
<211> LENGTH: 2676
<212> TYPE: DNA
<213> ORGANISM: Escherichia coli

<400> SEQUENCE: 23

```
atggctgtta ctaatgtcgc tgaacttaac gcactcgtag agcgtgtaaa aaaagcccag     60

cgtgaatatg ccagtttcac tcaagagcaa gtagacaaaa tcttccgcgc cgccgctctg    120

gctgctgcag atgctcgaat cccactcgcg aaaatggccg ttgccgaatc cggcatgggt    180

atcgtcgaag ataaagtgat caaaaaccac tttgcttctg aatatatcta caacgcctat    240

aaagatgaaa aaacctgtgg tgttctgtct gaagacgaca cttttggtac catcactatc    300

gctgaaccaa tcggtattat ttgcggtatc gttccgacca ctaacccgac ttcaactgct    360

atcttcaaat cgctgatcag tctgaagacc cgtaacgcca ttatcttctc cccgcacccg    420
```

```
cgtgcaaaag atgccaccaa caaagcggct gatatcgttc tgcaggctgc tatcgctgcc    480
ggtgctccga aagatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140
cgcgtttctt acttcggtca gaaaatgaaa acggcgcgta tcctgattaa caccccagcg   1200
tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg gttatgctga tcagatcact   1500
tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taaacgtatc   1740
tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg gtcgtgatta tgtagaaggt gaaactgcag cgaagaaaga agctgctccg   2640
gctaaagctg agaaaaaagc gaaaaaatcc gcttaa                             2676
```

<210> SEQ ID NO 24

<211> LENGTH: 891
<212> TYPE: PRT
<213> ORGANISM: Escherichia coli

<400> SEQUENCE: 24

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
```

-continued

```
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
            660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
    690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815
```

```
Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
    850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890


<210> SEQ ID NO 25
<211> LENGTH: 990
<212> TYPE: DNA
<213> ORGANISM: Escherichia coli

<400> SEQUENCE: 25

atgaaactcg ccgtttatag cacaaaacag tacgacaaga agtacctgca acaggtgaac      60

gagtcctttg gctttgagct ggaatttttt gactttctgc tgacggaaaa aaccgctaaa     120

actgccaatg gctgcgaagc ggtatgtatt ttcgtaaacg atgacggcag ccgcccggtg     180

ctggaagagc tgaaaaagca cggcgttaaa tatatcgccc tgcgctgtgc cggtttcaat     240

aacgtcgacc ttgacgcggc aaaagaactg gggctgaaag tagtccgtgt tccagcctat     300

gatccagagg ccgttgctga acacgccatc ggtatgatga tgacgctgaa ccgccgtatt     360

caccgcgcgt atcagcgtac ccgtgatgct aacttctctc tggaaggtct gaccggcttt     420

actatgtatg gcaaaacggc aggcgttatc ggtaccggta aaatcggtgt ggcgatgctg     480

cgcattctga aaggttttgg tatgcgtctg ctggcgttcg atccgtatcc aagtgcagcg     540

gcgctggaac tcggtgtgga gtatgtcgat ctgccaaccc tgttctctga atcagacgtt     600

atctctctgc actgcccgct gacaccggaa aactatcatc tgttgaacga agccgccttc     660

gaacagatga aaaatggcgt gatgatcgtc aataccagtc gcggtgcatt gattgattct     720

caggcagcaa ttgaagcgct gaaaaatcag aaaattggtt cgttgggtat ggacgtgtat     780

gagaacgaac gcgatctatt ctttgaagat aaatccaacg acgtgatcca ggatgacgta     840

ttccgtcgcc tgtctgcctg ccacaacgtg ctgtttaccg ggcaccaggc attcctgaca     900

gcagaagctc tgaccagtat ttctcagact acgctgcaaa acttaagcaa tctggaaaaa     960

ggcgaaacct gcccgaacga actggtttaa                                      990


<210> SEQ ID NO 26
<211> LENGTH: 329
<212> TYPE: PRT
<213> ORGANISM: Escherichia coli

<400> SEQUENCE: 26

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
            20                  25                  30

Leu Leu Thr Glu Lys Thr Ala Lys Thr Ala Asn Gly Cys Glu Ala Val
        35                  40                  45

Cys Ile Phe Val Asn Asp Asp Gly Ser Arg Pro Val Leu Glu Glu Leu
    50                  55                  60

Lys Lys His Gly Val Lys Tyr Ile Ala Leu Arg Cys Ala Gly Phe Asn
```

-continued

```
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
            100                 105                 110

Met Met Thr Leu Asn Arg Arg Ile His Arg Ala Tyr Gln Arg Thr Arg
        115                 120                 125

Asp Ala Asn Phe Ser Leu Glu Gly Leu Thr Gly Phe Thr Met Tyr Gly
    130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Glu Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325


<210> SEQ ID NO 27
<211> LENGTH: 1440
<212> TYPE: DNA
<213> ORGANISM: Escherichia coli

<400> SEQUENCE: 27

atgtcagtac ccgttcaaca tcctatgtat atcgatggac agtttgttac ctggcgtgga      60

gacgcatgga ttgatgtggt aaaccctgct acagaggctg tcatttcccg catacccgat     120

ggtcaggccg aggatgcccg taaggcaatc gatgcagcag aacgtgcaca accagaatgg     180

gaagcgttgc ctgctattga acgcgccagt tggttgcgca aaatctccgc cgggatccgc     240

gaacgcgcca gtgaaatcag tgcgctgatt gttgaagaag gggcaagat ccagcagctg     300

gctgaagtcg aagtggcttt tactgccgac tatatcgatt acatggcgga gtgggcacgg     360

cgttacgagg gcgagattat tcaaagcgat cgtccaggag aaaatattct tttgtttaaa     420

cgtgcgcttg gtgtgactac cggcattctg ccgtggaact tcccgttctt cctcattgcc     480

cgcaaaatgg ctcccgctct tttgaccggt aataccatcg tcattaaacc tagtgaattt     540

acgccaaaca atgcgattgc attcgccaaa atcgtcgatg aaataggcct tccgcgcggc     600

gtgtttaacc ttgtactggg gcgtggtgaa accgttgggc aagaactggc gggtaaccca     660
```

-continued

```
aaggtcgcaa tggtcagtat gacaggcagc gtctctgcag gtgagaagat catggcgact    720

gcggcgaaaa acatcaccaa agtgtgtctg gaattggggg gtaaagcacc agctatcgta    780

atggacgatg ccgatcttga actggcagtc aaagccatcg ttgattcacg cgtcattaat    840

agtgggcaag tgtgtaactg tgcagaacgt gtttatgtac agaaaggcat ttatgatcag    900

ttcgtcaatc ggctgggtga agcgatgcag gcggttcaat ttggtaaccc cgctgaacgc    960

aacgacattg cgatggggcc gttgattaac gccgcggcgc tggaaagggt cgagcaaaaa   1020

gtggcgcgcg cagtagaaga aggggcgaga gtggcgttcg gtggcaaagc ggtagagggg   1080

aaaggatatt attatccgcc gacattgctg ctggatgttc gccaggaaat gtcgattatg   1140

catgaggaaa cctttggccc ggtgctgcca gttgtcgcat ttgacacgct ggaagatgct   1200

atctcaatgg ctaatgacag tgattacggc ctgacctcat caatctatac ccaaaatctg   1260

aacgtcgcga tgaaagccat taaagggctg aagtttggtg aaacttacat caaccgtgaa   1320

aacttcgaag ctatgcaagg cttccacgcc ggatggcgta aatccggtat tggcggcgca   1380

gatggtaaac atggcttgca tgaatatctg cagacccagg tggtttattt acagtcttaa   1440
```

<210> SEQ ID NO 28
<211> LENGTH: 479
<212> TYPE: PRT
<213> ORGANISM: Escherichia coli

<400> SEQUENCE: 28

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
    130                 135                 140

Val Thr Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
    210                 215                 220

Val Ser Met Thr Gly Ser Val Ser Ala Gly Glu Lys Ile Met Ala Thr
225                 230                 235                 240
```

```
Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
    290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Ala Leu Glu Arg
                325                 330                 335

Val Glu Gln Lys Val Ala Arg Ala Val Glu Glu Gly Ala Arg Val Ala
            340                 345                 350

Phe Gly Gly Lys Ala Val Glu Gly Lys Gly Tyr Tyr Tyr Pro Pro Thr
        355                 360                 365

Leu Leu Leu Asp Val Arg Gln Glu Met Ser Ile Met His Glu Glu Thr
    370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
    450                 455                 460

Gly Leu His Glu Tyr Leu Gln Thr Gln Val Val Tyr Leu Gln Ser
465                 470                 475
```

```
<210> SEQ ID NO 29
<211> LENGTH: 1539
<212> TYPE: DNA
<213> ORGANISM: Escherichia coli

<400> SEQUENCE: 29

atgaccaata atcccccttc agcacagatt aagcccggcg agtatggttt ccccctcaag     60

ttaaaagccc gctatgacaa ctttattggc ggcgaatggg tagcccctgc cgacggcgag    120

tattaccaga atctgacgcc ggtgaccggg cagctgctgt gcgaagtggc gtcttcgggc    180

aaacgagaca tcgatctggc gctggatgct gcgcacaaag tgaaagataa atgggcgcac    240

acctcggtgc aggatcgtgc ggcgattctg tttaagattg ccgatcgaat ggaacaaaac    300

ctcgagctgt tagcgacagc tgaaacctgg gataacggca aacccattcg cgaaaccagt    360

gctgcggatg taccgctggc gattgaccat ttccgctatt tcgcctcgtg tattcgggcg    420

caggaaggtg ggatcagtga agttgatagc gaaaccgtgg cctatcattt ccatgaaccg    480

ttaggcgtgg tggggcagat tatcccgtgg aacttcccgc tgctgatggc gagctggaaa    540

atggctcccg cgctggcggc gggcaactgt gtggtgctga aacccgcacg tcttaccccg    600

ctttctgtac tgctgctaat ggaaattgtc ggtgatttac tgccgccggg cgtggtgaac    660

gtggtcaatg gcgcaggtgg ggtaattggc gaatatctgg cgacctcgaa acgcatcgcc    720

aaagtggcgt ttaccggctc aacggaagtg ggccaacaaa ttatgcaata cgcaacgcaa    780
```

-continued

```
aacattattc cggtgacgct ggagttgggc ggtaagtcgc caaatatctt ctttgctgat     840

gtgatggatg aagaagatgc ctttttcgat aaagcgctgg aaggctttgc actgtttgcc     900

tttaaccagg gcgaagtttg cacctgtccg agtcgtgctt tagtgcagga atctatctac     960

gaacgcttta tggaacgcgc catccgccgt gtcgaaagca ttcgtagcgg taacccgctc    1020

gacagcgtga cgcaaatggg cgcgcaggtt tctcacgggc aactggaaac catcctcaac    1080

tacattgata tcggtaaaaa agagggcgct gacgtgctca caggcgggcg gcgcaagctg    1140

ctggaaggtg aactgaaaga cggctactac ctcgaaccga cgattctgtt tggtcagaac    1200

aatatgcggg tgttccagga ggagattttt ggcccggtgc tggcggtgac caccttcaaa    1260

acgatggaag aagcgctgga gctggcgaac gatacgcaat atggcctggg cgcgggcgtc    1320

tggagccgca acggtaatct ggcctataag atggggcgcg gcatacaggc tgggcgcgtg    1380

tggaccaact gttatcacgc ttacccggca catgcggcgt ttggtggcta caaacaatca    1440

ggtatcggtc gcgaaaccca caagatgatg ctggagcatt accagcaaac caagtgcctg    1500

ctggtgagct actcggataa accgttgggg ctgttctga                           1539
```

<210> SEQ ID NO 30
<211> LENGTH: 512
<212> TYPE: PRT
<213> ORGANISM: Escherichia coli

<400> SEQUENCE: 30

```
Met Thr Asn Asn Pro Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
            20                  25                  30

Trp Val Ala Pro Ala Asp Gly Glu Tyr Tyr Gln Asn Leu Thr Pro Val
        35                  40                  45

Thr Gly Gln Leu Leu Cys Glu Val Ala Ser Ser Gly Lys Arg Asp Ile
    50                  55                  60

Asp Leu Ala Leu Asp Ala Ala His Lys Val Lys Asp Lys Trp Ala His
65                  70                  75                  80

Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
    130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240
```

-continued

Lys Val Ala Phe Thr Gly Ser Thr Glu Val Gly Gln Gln Ile Met Gln
245 250 255

Tyr Ala Thr Gln Asn Ile Ile Pro Val Thr Leu Glu Leu Gly Gly Lys
260 265 270

Ser Pro Asn Ile Phe Phe Ala Asp Val Met Asp Glu Glu Asp Ala Phe
275 280 285

Phe Asp Lys Ala Leu Glu Gly Phe Ala Leu Phe Ala Phe Asn Gln Gly
290 295 300

Glu Val Cys Thr Cys Pro Ser Arg Ala Leu Val Gln Glu Ser Ile Tyr
305 310 315 320

Glu Arg Phe Met Glu Arg Ala Ile Arg Arg Val Glu Ser Ile Arg Ser
325 330 335

Gly Asn Pro Leu Asp Ser Val Thr Gln Met Gly Ala Gln Val Ser His
340 345 350

Gly Gln Leu Glu Thr Ile Leu Asn Tyr Ile Asp Ile Gly Lys Lys Glu
355 360 365

Gly Ala Asp Val Leu Thr Gly Gly Arg Arg Lys Leu Leu Glu Gly Glu
370 375 380

Leu Lys Asp Gly Tyr Tyr Leu Glu Pro Thr Ile Leu Phe Gly Gln Asn
385 390 395 400

Asn Met Arg Val Phe Gln Glu Glu Ile Phe Gly Pro Val Leu Ala Val
405 410 415

Thr Thr Phe Lys Thr Met Glu Glu Ala Leu Glu Leu Ala Asn Asp Thr
420 425 430

Gln Tyr Gly Leu Gly Ala Gly Val Trp Ser Arg Asn Gly Asn Leu Ala
435 440 445

Tyr Lys Met Gly Arg Gly Ile Gln Ala Gly Arg Val Trp Thr Asn Cys
450 455 460

Tyr His Ala Tyr Pro Ala His Ala Ala Phe Gly Gly Tyr Lys Gln Ser
465 470 475 480

Gly Ile Gly Arg Glu Thr His Lys Met Met Leu Glu His Tyr Gln Gln
485 490 495

Thr Lys Cys Leu Leu Val Ser Tyr Ser Asp Lys Pro Leu Gly Leu Phe
500 505 510

<210> SEQ ID NO 31
<211> LENGTH: 1812
<212> TYPE: DNA
<213> ORGANISM: Escherichia coli

<400> SEQUENCE: 31
atgaatccac aattgttacg cgtaacaaat cgaatcattg aacgttcgcg cgagactcgc 60
tctgcttatc tcgcccggat agaacaagcg aaaacttcga ccgttcatcg ttcgcagttg 120
gcatgcggta acctggcaca cggtttcgct gcctgccagc cagaagacaa agcctctttg 180
aaaagcatgt tgcgtaacaa tatcgccatc atcacctcct ataacgacat gctctccgcg 240
caccagcctt atgaacacta tccagaaatc attcgtaaag ccctgcatga agcgaatgcg 300
gttggtcagg ttgcgggcgg tgttccggcg atgtgtgatg gtgtcaccca ggggcaggat 360
ggaatggaat tgtcgctgct aagccgcgaa gtgatagcga tgtctgcggc ggtggggctg 420
tcccataaca tgtttgatgg tgctctgttc ctcggtgtgt gcgacaagat tgtcccgggt 480
ctgacgatgg cagccctgtc gtttggtcat ttgcctgcgg tgtttgtgcc gtctggaccg 540
atggcaagcg gtttgccaaa taaagaaaaa gtgcgtattc gccagcttta tgccgaaggt 600

-continued

```
aaagtggacc gcatggcctt actggagtca gaagccgcgt cttaccatgc gccgggaaca    660

tgtactttct acggtactgc caacaccaac cagatggtgg tggagtttat ggggatgcag    720

ttgccaggct cttcttttgt tcatccggat tctccgctgc gcgatgcttt gaccgccgca    780

gctgcgcgtc aggttacacg catgaccggt aatggtaatg aatggatgcc gatcggtaag    840

atgatcgatg agaaagtggt ggtgaacggt atcgttgcac tgctggcgac cggtggttcc    900

actaaccaca ccatgcacct ggtggcgatg gcgcgcgcgg ccggtattca gattaactgg    960

gatgacttct ctgacctttc tgatgttgta ccgctgatgg cacgtctcta cccgaacggt   1020

ccggccgata ttaaccactt ccaggcggca ggtggcgtac cggttctggt gcgtgaactg   1080

ctcaaagcag gcctgctgca tgaagatgtc aatacggtgg caggttttgg tctgtctcgt   1140

tataccottg aaccatggct gaataatggt gaactggact ggcgggaagg ggcggaaaaa   1200

tcactcgaca gcaatgtgat cgcttccttc gaacaacctt tctctcatca tggtgggaca   1260

aaagtgttaa gcggtaacct gggccgtgcg gttatgaaaa cctctgccgt gccggttgag   1320

aaccaggtga ttgaagcgcc agcggttgtt tttgaaagcc agcatgacgt tatgccggcc   1380

tttgaagcgg gtttgctgga ccgcgattgt gtcgttgttg tccgtcatca ggggccaaaa   1440

gcgaacggaa tgccagaatt acataaactc atgccgccac ttggtgtatt attggaccgg   1500

tgtttcaaaa ttgcgttagt taccgatgga cgactctccg gcgcttcagg taaagtgccg   1560

tcagctatcc acgtaacacc agaagcctac gatggcgggc tgctggcaaa agtgcgcgac   1620

ggggacatca ttcgtgtgaa tggacagaca ggcgaactga cgctgctggt agacgaagcg   1680

gaactggctg ctcgcgaacc gcacattcct gacctgagcg cgtcacgcgt gggaacagga   1740

cgtgaattat tcagcgcctt gcgtgaaaaa ctgtccggtg ccgaacaggg cgcaacctgt   1800

atcacttttt aa                                                       1812
```

```
<210> SEQ ID NO 32
<211> LENGTH: 603
<212> TYPE: PRT
<213> ORGANISM: Escherichia coli

<400> SEQUENCE: 32

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60

Arg Asn Asn Ile Ala Ile Ile Thr Ser Tyr Asn Asp Met Leu Ser Ala
65                  70                  75                  80

His Gln Pro Tyr Glu His Tyr Pro Glu Ile Ile Arg Lys Ala Leu His
                85                  90                  95

Glu Ala Asn Ala Val Gly Gln Val Ala Gly Gly Val Pro Ala Met Cys
            100                 105                 110

Asp Gly Val Thr Gln Gly Gln Asp Gly Met Glu Leu Ser Leu Leu Ser
        115                 120                 125

Arg Glu Val Ile Ala Met Ser Ala Ala Val Gly Leu Ser His Asn Met
    130                 135                 140

Phe Asp Gly Ala Leu Phe Leu Gly Val Cys Asp Lys Ile Val Pro Gly
```

-continued

```
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190

Ile Arg Gln Leu Tyr Ala Glu Gly Lys Val Asp Arg Met Ala Leu Leu
        195                 200                 205

Glu Ser Glu Ala Ala Ser Tyr His Ala Pro Gly Thr Cys Thr Phe Tyr
    210                 215                 220

Gly Thr Ala Asn Thr Asn Gln Met Val Val Glu Phe Met Gly Met Gln
225                 230                 235                 240

Leu Pro Gly Ser Ser Phe Val His Pro Asp Ser Pro Leu Arg Asp Ala
                245                 250                 255

Leu Thr Ala Ala Ala Ala Arg Gln Val Thr Arg Met Thr Gly Asn Gly
            260                 265                 270

Asn Glu Trp Met Pro Ile Gly Lys Met Ile Asp Glu Lys Val Val Val
        275                 280                 285

Asn Gly Ile Val Ala Leu Leu Ala Thr Gly Gly Ser Thr Asn His Thr
    290                 295                 300

Met His Leu Val Ala Met Ala Arg Ala Ala Gly Ile Gln Ile Asn Trp
305                 310                 315                 320

Asp Asp Phe Ser Asp Leu Ser Asp Val Val Pro Leu Met Ala Arg Leu
                325                 330                 335

Tyr Pro Asn Gly Pro Ala Asp Ile Asn His Phe Gln Ala Ala Gly Gly
            340                 345                 350

Val Pro Val Leu Val Arg Glu Leu Leu Lys Ala Gly Leu Leu His Glu
        355                 360                 365

Asp Val Asn Thr Val Ala Gly Phe Gly Leu Ser Arg Tyr Thr Leu Glu
    370                 375                 380

Pro Trp Leu Asn Asn Gly Glu Leu Asp Trp Arg Glu Gly Ala Glu Lys
385                 390                 395                 400

Ser Leu Asp Ser Asn Val Ile Ala Ser Phe Glu Gln Pro Phe Ser His
                405                 410                 415

His Gly Gly Thr Lys Val Leu Ser Gly Asn Leu Gly Arg Ala Val Met
            420                 425                 430

Lys Thr Ser Ala Val Pro Val Glu Asn Gln Val Ile Glu Ala Pro Ala
        435                 440                 445

Val Val Phe Glu Ser Gln His Asp Val Met Pro Ala Phe Glu Ala Gly
    450                 455                 460

Leu Leu Asp Arg Asp Cys Val Val Val Val Arg His Gln Gly Pro Lys
465                 470                 475                 480

Ala Asn Gly Met Pro Glu Leu His Lys Leu Met Pro Pro Leu Gly Val
                485                 490                 495

Leu Leu Asp Arg Cys Phe Lys Ile Ala Leu Val Thr Asp Gly Arg Leu
            500                 505                 510

Ser Gly Ala Ser Gly Lys Val Pro Ser Ala Ile His Val Thr Pro Glu
        515                 520                 525

Ala Tyr Asp Gly Gly Leu Leu Ala Lys Val Arg Asp Gly Asp Ile Ile
    530                 535                 540

Arg Val Asn Gly Gln Thr Gly Glu Leu Thr Leu Leu Val Asp Glu Ala
545                 550                 555                 560

Glu Leu Ala Ala Arg Glu Pro His Ile Pro Asp Leu Ser Ala Ser Arg
                565                 570                 575
```

Val Gly Thr Gly Arg Glu Leu Phe Ser Ala Leu Arg Glu Lys Leu Ser
580 585 590

Gly Ala Glu Gln Gly Ala Thr Cys Ile Thr Phe
595 600

<210> SEQ ID NO 33
<211> LENGTH: 717
<212> TYPE: DNA
<213> ORGANISM: Escherichia coli

<400> SEQUENCE: 33
atgcagaccc cgcacattct tatcgttgaa gacgagttgg taacacgcaa cacgttgaaa 60
agtattttcg aagcggaagg ctatgatgtt ttcgaagcga cagatggcgc ggaaatgcat 120
cagatcctct ctgaatatga catcaacctg gtgatcatgg atatcaatct gccgggtaag 180
aacggtcttc tgttagcgcg tgaactgcgc gagcaggcga atgttgcgtt gatgttcctg 240
actggccgtg acaacgaagt cgataaaatt ctcggcctcg aaatcggtgc agatgactac 300
atcaccaaac cgttcaaccc gcgtgaactg acgattcgtg cacgcaacct actgtcccgt 360
accatgaatc tgggtactgt cagcgaagaa cgtcgtagcg ttgaaagcta caagttcaat 420
ggttgggaac tggacatcaa cagccgttcg ttgatcggcc ctgatggcga gcagtacaag 480
ctgccgcgca gcgagttccg cgccatgctt cacttctgtg aaaacccagg caaaattcag 540
tcccgtgctg aactgctgaa gaaaatgacc ggccgtgagc tgaaaccgca cgaccgtact 600
gtagacgtga cgatccgccg tattcgtaaa catttcgaat ctacgccgga tacgccggaa 660
atcatcgcca ccattcacgg tgaaggttat cgcttctgcg gtgatctgga agattaa 717

<210> SEQ ID NO 34
<211> LENGTH: 238
<212> TYPE: PRT
<213> ORGANISM: Escherichia coli

<400> SEQUENCE: 34

Met Gln Thr Pro His Ile Leu Ile Val Glu Asp Glu Leu Val Thr Arg
1 5 10 15

Asn Thr Leu Lys Ser Ile Phe Glu Ala Glu Gly Tyr Asp Val Phe Glu
20 25 30

Ala Thr Asp Gly Ala Glu Met His Gln Ile Leu Ser Glu Tyr Asp Ile
35 40 45

Asn Leu Val Ile Met Asp Ile Asn Leu Pro Gly Lys Asn Gly Leu Leu
50 55 60

Leu Ala Arg Glu Leu Arg Glu Gln Ala Asn Val Ala Leu Met Phe Leu
65 70 75 80

Thr Gly Arg Asp Asn Glu Val Asp Lys Ile Leu Gly Leu Glu Ile Gly
85 90 95

Ala Asp Asp Tyr Ile Thr Lys Pro Phe Asn Pro Arg Glu Leu Thr Ile
100 105 110

Arg Ala Arg Asn Leu Leu Ser Arg Thr Met Asn Leu Gly Thr Val Ser
115 120 125

Glu Glu Arg Arg Ser Val Glu Ser Tyr Lys Phe Asn Gly Trp Glu Leu
130 135 140

Asp Ile Asn Ser Arg Ser Leu Ile Gly Pro Asp Gly Glu Gln Tyr Lys
145 150 155 160

Leu Pro Arg Ser Glu Phe Arg Ala Met Leu His Phe Cys Glu Asn Pro
165 170 175

```
Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Glu Asp
225                 230                 235


<210> SEQ ID NO 35
<211> LENGTH: 1305
<212> TYPE: DNA
<213> ORGANISM: Escherichia coli

<400> SEQUENCE: 35

ttgactacgc cattgaaaaa gattgtgatt gtcggcggcg gtgctggtgg gctggaaatg      60

gcaacacagc tggggcataa gctgggacgc aagaaaaaag ccaaaattac gctggtcgat     120

cgtaaccaca gccacctgtg gaaaccgctg ctgcacgaag tggcgactgg ctcgcttgat     180

gaaggcgtcg atgcgttgag ctatctggcc catgcgcgca atcatggttt ccagttccag     240

ctgggttccg tcattgatat tgatcgtgaa gcgaaaacaa tcactattgc agaactgcgc     300

gacgagaaag gtgaactgct ggttccggaa cgtaaaatcg cctatgacac cctggtaatg     360

gcgctgggta gcacctctaa cgatttcaat acgccaggtg tcaaagagaa ctgcattttc     420

ctcgataacc cgcaccaggc gcgtcgcttc caccaggaga tgctgaattt gttcctgaaa     480

tactccgcca acctgggcgc gaatggcaaa gtgaacattg cgattgtcgg cggcggcgcg     540

acgggtgtag aactctccgc tgaattgcac aacgcggtca agcaactgca cagctacggt     600

tacaaaggcc tgaccaacga agccctgaac gtaacgctgg tagaagcggg agaacgtatt     660

ttgcctgcgt taccgccacg tatctctgct gcggcccaca acgagctaac gaaacttggc     720

gttcgcgtgc tgacgcaaac catggtcacc agtgctgatg aaggcggcct gcacactaaa     780

gatggcgaat atattgaggc tgatctgatg gtatgggcag ccgggatcaa agcgccagac     840

ttcctgaaag atatcggtgg tcttgaaact aaccgtatca accagctggt ggtggaaccg     900

acgctgcaaa ccacccgcga tccagacatt tacgctattg gcgactgcgc gtcatgcccg     960

cgtccggaag gggctttgt tccgccgcgt gctcaggctg cacaccagat ggcgacttgc    1020

gcaatgaaca acattctggc gcagatgaac ggtaagccgc tgaaaaatta tcagtataaa    1080

gatcatggtt cgctggtatc gctgtcgaac ttctccaccg tcggtagcct gatgggtaac    1140

ctgacgcgcg gctcaatgat gattgaagga cgaattgcgc gctttgtata tatctcgcta    1200

taccgaatgc atcagattgc gctgcatggt tactttaaaa ccggattaat gatgctggtg    1260

gggagtatta accgcgttat ccgtccgcgt ttgaagttgc attaa                   1305


<210> SEQ ID NO 36
<211> LENGTH: 434
<212> TYPE: PRT
<213> ORGANISM: Escherichia coli

<400> SEQUENCE: 36

Met Thr Thr Pro Leu Lys Lys Ile Val Ile Val Gly Gly Gly Ala Gly
1               5                   10                  15

Gly Leu Glu Met Ala Thr Gln Leu Gly His Lys Leu Gly Arg Lys Lys
            20                  25                  30
```

```
Lys Ala Lys Ile Thr Leu Val Asp Arg Asn His Ser His Leu Trp Lys
        35                  40                  45

Pro Leu Leu His Glu Val Ala Thr Gly Ser Leu Asp Glu Gly Val Asp
    50                  55                  60

Ala Leu Ser Tyr Leu Ala His Ala Arg Asn His Gly Phe Gln Phe Gln
65                  70                  75                  80

Leu Gly Ser Val Ile Asp Ile Asp Arg Glu Ala Lys Thr Ile Thr Ile
                85                  90                  95

Ala Glu Leu Arg Asp Glu Lys Gly Glu Leu Leu Val Pro Glu Arg Lys
            100                 105                 110

Ile Ala Tyr Asp Thr Leu Val Met Ala Leu Gly Ser Thr Ser Asn Asp
        115                 120                 125

Phe Asn Thr Pro Gly Val Lys Glu Asn Cys Ile Phe Leu Asp Asn Pro
    130                 135                 140

His Gln Ala Arg Arg Phe His Gln Glu Met Leu Asn Leu Phe Leu Lys
145                 150                 155                 160

Tyr Ser Ala Asn Leu Gly Ala Asn Gly Lys Val Asn Ile Ala Ile Val
                165                 170                 175

Gly Gly Gly Ala Thr Gly Val Glu Leu Ser Ala Glu Leu His Asn Ala
            180                 185                 190

Val Lys Gln Leu His Ser Tyr Gly Tyr Lys Gly Leu Thr Asn Glu Ala
        195                 200                 205

Leu Asn Val Thr Leu Val Glu Ala Gly Glu Arg Ile Leu Pro Ala Leu
    210                 215                 220

Pro Pro Arg Ile Ser Ala Ala Ala His Asn Glu Leu Thr Lys Leu Gly
225                 230                 235                 240

Val Arg Val Leu Thr Gln Thr Met Val Thr Ser Ala Asp Glu Gly Gly
                245                 250                 255

Leu His Thr Lys Asp Gly Glu Tyr Ile Glu Ala Asp Leu Met Val Trp
            260                 265                 270

Ala Ala Gly Ile Lys Ala Pro Asp Phe Leu Lys Asp Ile Gly Gly Leu
        275                 280                 285

Glu Thr Asn Arg Ile Asn Gln Leu Val Val Glu Pro Thr Leu Gln Thr
    290                 295                 300

Thr Arg Asp Pro Asp Ile Tyr Ala Ile Gly Asp Cys Ala Ser Cys Pro
305                 310                 315                 320

Arg Pro Glu Gly Gly Phe Val Pro Pro Arg Ala Gln Ala Ala His Gln
                325                 330                 335

Met Ala Thr Cys Ala Met Asn Asn Ile Leu Ala Gln Met Asn Gly Lys
            340                 345                 350

Pro Leu Lys Asn Tyr Gln Tyr Lys Asp His Gly Ser Leu Val Ser Leu
        355                 360                 365

Ser Asn Phe Ser Thr Val Gly Ser Leu Met Gly Asn Leu Thr Arg Gly
    370                 375                 380

Ser Met Met Ile Glu Gly Arg Ile Ala Arg Phe Val Tyr Ile Ser Leu
385                 390                 395                 400

Tyr Arg Met His Gln Ile Ala Leu His Gly Tyr Phe Lys Thr Gly Leu
                405                 410                 415

Met Met Leu Val Gly Ser Ile Asn Arg Val Ile Arg Pro Arg Leu Lys
            420                 425                 430

Leu His
```

<210> SEQ ID NO 37

<211> LENGTH: 1809
<212> TYPE: DNA
<213> ORGANISM: Escherichia coli

<400> SEQUENCE: 37

```
tcagccattc gccttctcct tcttattggc tgcttccgcc ttatcggctg catccgcttc     60
gccaccgtaa acgcgtttag ctggcggcag cgtagtaatc ttcacgtcgc tgtactccag    120
gcgagtcgtg ccatcagcat cgcggaaggc gagggtgtgt ttgaggaagt tgacgtcgtc    180
acgctcggtg caaccttcgt ccagacgctg gtgcgcgccg cgggactctt tacgtgccat    240
tgcggagtgc gccatacatt cagcaacgtt cagaccgtgg cccagttcaa tggtgtagag    300
caggtcggtg ttgaacacgc tggaagtgtc ggtgatgcgc acgcgcttga agcgttcctg    360
cagctctgcc agcttgtcga tggttttctg catcagttcc ggcgtacggt agataccgca    420
gccttcttcc atagccaggc ccatttcgtc gcggatcttc gcccagtttt cgccgccatc    480
ctggttaacc agatctttca gacgttgttc aacgccagct gcctgcgctt caattgccgc    540
ttcgttgcca ttaccggcag ttgctgcacg ctctgtcgct tgttcaccgg ccagacggcc    600
gaagaccacc agttccgcca gggagttaga acccagacgg tttgcaccgt gcagaccaac    660
agaggaacat tcacccacgg cgaacagacc tttaatgcgg gtttcacagt tctgatcggt    720
ttcgataccg cccatggtgt agtgtgcggt cggacgtacc ggaatcggtt ctttaaccgg    780
atcgacgcca acgtacgctt tcgccagttc gcagatgaac ggcagacgtt catgcagttt    840
tttctcgccg aggtgacgca agtcgagata aaccacatcg ccacgcggcg tggagatggt    900
gttgccttta cgccattcgt gccagaaggc ctgagagact ttgtcgcgtg gacccagttc    960
catatatttg tttttcggct cgcccagcgg agtttccggg cccatgccgt aatcttgcag   1020
ataacggtag ccatttttgt tgaccagaat accgccttca ccgcggcaac cttcggtcat   1080
caggataccg gaacctggca gaccggttgg gtgatactga acgaattcca tgtcacgcag   1140
cggaacgccg tggcttagcg ccatacccat accgtcaccg gtaacgatgc cgccgttggt   1200
gttgtaacga taaacgcgac ccgcaccgcc agtagccata acgaccgcgt tagcacggat   1260
ctgcaccagc gtgccttcca tcatgttcat tgctaccagg ccgcgaacat gaccatcatc   1320
aaccagaata tccagcacga aatgttcgtc aaaacgctgg atctgcggga attgcagaga   1380
ggtctggaac agcgtgtgca gcatatggaa gccggtctta tcggcggcga accaggtgcg   1440
ctcgattttc atgccgccga agcgacgtac gttgacgcta ccatccgggc gacggctcca   1500
tgggcatccc cacagttcca gttgggtcat ttcggttggg cagtggtgga cgaaataatc   1560
cacgacatcc tgctcacaca accagtcgcc acccgctact gtatcgtgaa agtgatattc   1620
gaagctgtca tgatcctgcg cgacagcggc ggagcccccct tctgcagcaa cggtatggct   1680
acgcatcggg tatacttttg agattagtgc gatttttgca ttcggatttg cctgcgcggc   1740
agcaattgca gcacgtaatc ccgcgccacc ggcgcctaca atggcaagat cggcttgaaa   1800
ggtttgcac                                                           1809
```

<210> SEQ ID NO 38
<211> LENGTH: 602
<212> TYPE: PRT
<213> ORGANISM: Escherichia coli

<400> SEQUENCE: 38

```
Met Gln Thr Phe Gln Ala Asp Leu Ala Ile Val Gly Ala Gly Gly Ala
1               5                   10                  15
```

-continued

```
Gly Leu Arg Ala Ala Ile Ala Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
        275                 280                 285

Asp Lys Val Ser Gln Ala Phe Trp His Glu Trp Arg Lys Gly Asn Thr
    290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys
        355                 360                 365

Glu Thr Arg Ile Lys Gly Leu Phe Ala Val Gly Glu Cys Ser Ser Val
    370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
            420                 425                 430

Val Glu Gln Arg Leu Lys Asp Leu Val Asn Gln Asp Gly Gly Glu Asn
```

```
        435                 440                 445

Trp Ala Lys Ile Arg Asp Glu Met Gly Leu Ala Met Glu Glu Gly Cys
    450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
    530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600
```

<210> SEQ ID NO 39
<211> LENGTH: 735
<212> TYPE: DNA
<213> ORGANISM: Escherichia coli

<400> SEQUENCE: 39

```
ttagcgtggt ttcagggtcg cgataagaaa gtctttcgaa ctttctactt tgccctgctg      60

aatggccgca gccggatcga cgtgtttcgg gcagacttcg gagcagtagc ccacgaaagt     120

acagctccat acgccgttct ggctgttcaa ctgcgccata cgctccttct taccgtggtc     180

gcggctatct tcgttataac gatgcgccag cgtaatggca gccggaccga tgaactctgg     240

gttcaggcca aactgcgggc acgcggcgta gcacaaacca cagttgatgc aaccggagaa     300

ctggtgatac ttcgccatct gcgccggggt ctggatgtta gtaccctgat ccgcggtgcg     360

ggagttgccg atgatgtacg gtttgatcgc ttccagactt tcgatgaagt gggtcatatc     420

gaccaccaga tcgcgttcaa tcgggaagtt agctaacgct tcaaccttca taccgtcggt     480

gtaatcacgc aggaaggttt tacatgccag ttttggcacg ttgttaacca tcatgccgca     540

ggaaccacaa atcgccatac ggcaggacca gcggtagctc aggtccggtg ccaggttgtc     600

tttgatgtag cccagcgcat ccagtaatga ggtagttgcg tcataaggca cttcatagaa     660

tgcgctatgc ggtgcggtat cgacttccgg gttatagcgc accacctcaa ttttcaggtt     720

tttcatctca gccat                                                      735
```

<210> SEQ ID NO 40
<211> LENGTH: 244
<212> TYPE: PRT
<213> ORGANISM: Escherichia coli

<400> SEQUENCE: 40

```
Met Ala Glu Met Lys Asn Leu Lys Ile Glu Val Val Arg Tyr Asn Pro
1               5                   10                  15

Glu Val Asp Thr Ala Pro His Ser Ala Phe Tyr Glu Val Pro Tyr Asp
            20                  25                  30
```

```
Ala Thr Thr Ser Leu Leu Asp Ala Leu Gly Tyr Ile Lys Asp Asn Leu
        35                  40                  45

Ala Pro Asp Leu Ser Tyr Arg Trp Ser Cys Arg Met Ala Ile Cys Gly
    50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125

Asp Gln Gly Thr Asn Ile Gln Thr Pro Ala Gln Met Ala Lys Tyr His
    130                 135                 140

Gln Phe Ser Gly Cys Ile Asn Cys Gly Leu Cys Tyr Ala Ala Cys Pro
145                 150                 155                 160

Gln Phe Gly Leu Asn Pro Glu Phe Ile Gly Pro Ala Ala Ile Thr Leu
                165                 170                 175

Ala His Arg Tyr Asn Glu Asp Ser Arg Asp His Gly Lys Lys Glu Arg
            180                 185                 190

Met Ala Gln Leu Asn Ser Gln Asn Gly Val Trp Ser Cys Thr Phe Val
        195                 200                 205

Gly Tyr Cys Ser Glu Val Cys Pro Lys His Val Asp Pro Ala Ala Ala
    210                 215                 220

Ile Gln Gln Gly Lys Val Glu Ser Ser Lys Asp Phe Leu Ile Ala Thr
225                 230                 235                 240

Leu Lys Pro Arg
```

<210> SEQ ID NO 41
<211> LENGTH: 396
<212> TYPE: DNA
<213> ORGANISM: Escherichia coli

<400> SEQUENCE: 41

```
ttaccagtac agggcaacaa acaggattac gatggtggca accacagtta ccgcccagag     60

acttttgata attggctctg gtcccatttt ttcgtctttt acaatgatat tggccgcttt    120

cggtgccagt tcaaaccagg ttttggtgtg cagcagagct gccgccagag tgatcaggtt    180

aatgatcacg ataaccgggt tttgtaaaaa gtcgacgaat cccgcccagg cttccgggcc    240

atttttcagg gcaaacagcc cgaaaatcag ttcaatgctg aaccacacag ccggaaccgc    300

cgtgccttcg cgcagcatgt aaaagcgata aaacggcaat tttttccacc aggtggacgt    360

cattggccgt acatacggtt tacgtttagt cgtcat                              396
```

<210> SEQ ID NO 42
<211> LENGTH: 131
<212> TYPE: PRT
<213> ORGANISM: Escherichia coli

<400> SEQUENCE: 42

```
Met Thr Thr Lys Arg Lys Pro Tyr Val Arg Pro Met Thr Ser Thr Trp
1               5                   10                  15

Trp Lys Lys Leu Pro Phe Tyr Arg Phe Tyr Met Leu Arg Glu Gly Thr
            20                  25                  30

Ala Val Pro Ala Val Trp Phe Ser Ile Glu Leu Ile Phe Gly Leu Phe
```

```
        35                  40                  45

Ala Leu Lys Asn Gly Pro Glu Ala Trp Ala Gly Phe Val Asp Phe Leu
    50                  55                  60

Gln Asn Pro Val Ile Val Ile Ile Asn Leu Ile Thr Leu Ala Ala Ala
65                  70                  75                  80

Leu Leu His Thr Lys Thr Trp Phe Glu Leu Ala Pro Lys Ala Ala Asn
                85                  90                  95

Ile Ile Val Lys Asp Glu Lys Met Gly Pro Glu Pro Ile Ile Lys Ser
            100                 105                 110

Leu Trp Ala Val Thr Val Val Ala Thr Ile Val Ile Leu Phe Val Ala
        115                 120                 125

Leu Tyr Trp
    130


<210> SEQ ID NO 43
<211> LENGTH: 360
<212> TYPE: DNA
<213> ORGANISM: Escherichia coli

<400> SEQUENCE: 43

ttagattgta acgacaccaa tcagcgtgac aactgtcagg atagcagcca gaccgtagaa      60

aacccatttg cccgcaggta cgtggatttt cagatcgtgc atcgcgtggt gcatacggtg     120

taaaccacac cacagcggca gaacgatcat caggaacagg aatacgcgac caatgaagct     180

ctgcgcgaac gccagaacgc gctcgtagct cagcgcatca cccggaaaca accccagtgg     240

cagcagaata cccaccagca ggatcatcac cggcgcaatg atggcgctcc acataccacc     300

ggccccgaag aggccccaga ataccggttc gtcagaacgc tttggatttg gattaatcat     360


<210> SEQ ID NO 44
<211> LENGTH: 119
<212> TYPE: PRT
<213> ORGANISM: Escherichia coli

<400> SEQUENCE: 44

Met Ile Asn Pro Asn Pro Lys Arg Ser Asp Glu Pro Val Phe Trp Gly
1               5                   10                  15

Leu Phe Gly Ala Gly Gly Met Trp Ser Ala Ile Ile Ala Pro Val Met
            20                  25                  30

Ile Leu Leu Val Gly Ile Leu Leu Pro Leu Gly Leu Phe Pro Gly Asp
        35                  40                  45

Ala Leu Ser Tyr Glu Arg Val Leu Ala Phe Ala Gln Ser Phe Ile Gly
    50                  55                  60

Arg Val Phe Leu Phe Leu Met Ile Val Leu Pro Leu Trp Cys Gly Leu
65                  70                  75                  80

His Arg Met His His Ala Met His Asp Leu Lys Ile His Val Pro Ala
                85                  90                  95

Gly Lys Trp Val Phe Tyr Gly Leu Ala Ala Ile Leu Thr Val Val Thr
            100                 105                 110

Leu Ile Gly Val Val Thr Ile
        115


<210> SEQ ID NO 45
<211> LENGTH: 1602
<212> TYPE: DNA
<213> ORGANISM: Escherichia coli

<400> SEQUENCE: 45
```

-continued

```
atgactgaac aggcaacaac aaccgatgaa ctggctttca caaggccgta tggcgagcag     60
gagaagcaaa ttcttactgc cgaagcggta gaatttctga ctgagctggt gacgcatttt    120
acgccacaac gcaataaact tctggcagcg cgcattcagc agcagcaaga tattgataac    180
ggaacgttgc ctgattttat ttcggaaaca gcttccattc gcgatgctga ttggaaaatt    240
cgcgggattc ctgcggactt agaagaccgc cgcgtagaga taactggccc ggtagagcgc    300
aagatggtga tcaacgcgct caacgccaat gtgaaagtct ttatggccga tttcgaagat    360
tcactggcac cagactggaa caaagtgatc gacgggcaaa ttaacctgcg tgatgcggtt    420
aacggcacca tcagttacac caatgaagca ggcaaaattt accagctcaa gcccaatcca    480
gcggttttga tttgtcgggt acgcggtctg cacttgccgg aaaaacatgt cacctggcgt    540
ggtgaggcaa tccccggcag cctgtttgat tttgcgctct atttcttcca caactatcag    600
gcactgttgg caaagggcag tggtccctat ttctatctgc cgaaaaccca gtcctggcag    660
gaagcggcct ggtggagcga agtcttcagc tatgcagaag atcgctttaa tctgccgcgc    720
ggcaccatca aggcgacgtt gctgattgaa acgctgcccg ccgtgttcca gatggatgaa    780
atccttcacg cgctgcgtga ccatattgtt ggtctgaact gcggtcgttg ggattacatc    840
ttcagctata tcaaaacgtt gaaaaactat cccgatcgcg tcctgccaga cagacaggca    900
gtgacgatgg ataaaccatt cctgaatgct tactcacgcc tgttgattaa aacctgccat    960
aaacgcggtg cttttgcgat gggcggcatg gcggcgttta ttccgagcaa agatgaagag   1020
cacaataacc aggtgctcaa caaagtaaaa gcggataaat cgctggaagc caataacggt   1080
cacgatggca catggatcgc tcacccaggc cttgcggaca cggcaatggc ggtattcaac   1140
gacattctcg gctcccgtaa aaatcagctt gaagtgatgc gcgaacaaga cgcgccgatt   1200
actgccgatc agctgctggc accttgtgat ggtgaacgca ccgaagaagg tatgcgcgcc   1260
aacattcgcg tggctgtgca gtacatcgaa gcgtggatct ctggcaacgg ctgtgtgccg   1320
atttatggcc tgatggaaga tgcggcgacg gctgaaattt cccgtacctc gatctggcag   1380
tggatccatc atcaaaaaac gttgagcaat ggcaaaccgg tgaccaaagc cttgttccgc   1440
cagatgctgg gcgaagagat gaaagtcatt gccagcgaac tgggcgaaga acgtttctcc   1500
caggggcgtt ttgacgatgc cgcacgcttg atggaacaga tcaccacttc cgatgagtta   1560
attgatttcc tgaccctgcc aggctaccgc ctgttagcgt aa                      1602
```

<210> SEQ ID NO 46
<211> LENGTH: 533
<212> TYPE: PRT
<213> ORGANISM: Escherichia coli

<400> SEQUENCE: 46

```
Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Arg Val Glu Ile Thr Gly
```

```
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510
```

```
Gln Ile Thr Thr Ser Asp Glu Leu Ile Asp Phe Leu Thr Leu Pro Gly
        515                 520                 525

Tyr Arg Leu Leu Ala
    530


<210> SEQ ID NO 47
<211> LENGTH: 2172
<212> TYPE: DNA
<213> ORGANISM: Escherichia coli

<400> SEQUENCE: 47

atgagtcaaa ccataaccca gagccgttta cgcattgacg ccaattttaa acgttttgtg     60

gatgaagaag ttttaccggg aacagggctg gacgctgcgg cgttctggcg caattttgat    120

gagatcgttc atgatctggc accagaaaat cgtcagttgc tggcagaacg cgatcgcatt    180

caggcagcgc ttgatgagtg gcatcgcagc aatccggggc cggtaaaaga taaagcggcc    240

tataaatctt tcctgcgtga actgggctac ctggtgccgc aaccggagcg cgtgacggtg    300

gaaaccacgg gcattgacag cgaaatcacc agccaggcgg ggccgcagct ggtggttccg    360

gcaatgaacg cccgctacgc gctgaacgcg gcgaacgctc gctggggctc actgtacgat    420

gcgttatacg gcagcgacat catcccgcag gaaggggcga tggtcagcgg ctacgatccg    480

caacgcggtg agcaggttat cgcctgggtt cggcgtttcc tcgatgaatc tctaccgctg    540

gaaaacggca gctatcagga tgtggtggcg tttaaggtgg ttgataaaca attacgcatc    600

cagttgaaaa atggtaaaga aaccacgtta cgtactccag cacagtttgt cggttaccgt    660

ggcgatgccg ctgcgccgac ctgcattttg ctgaaaaata acggcctgca tattgagctg    720

caaatcgatg ccaatgggcg gattggcaaa gacgatccgg cgcacatcaa cgatgttatc    780

gtcgaagctg ctatcagtac cattctcgac tgcgaagatt cggtcgcggc ggttgatgcg    840

gaagataaaa tcctgctgta ccgcaacctg ctgggcctga tgcaggggac tctgcaagag    900

aaaatggaga aaaacggtcg gcaaatcgtg cgtaaactga atgacgatcg tcattacacc    960

gccgccgatg gctctgaaat ttctctgcac ggacgctcgc tgctgtttat ccgcaacgtg   1020

ggtcatttga tgaccattcc tgtgatttgg gacagcgaag gcaatgaaat cccggaaggc   1080

attcttgatg gcgtcatgac tggcgcgatt gccctctatg atttaaaagt gcagaaaaac   1140

tcgcgcactg gcagcgtcta tattgtgaaa ccgaaaatgc acggtccgca ggaagtggcg   1200

ttcgccaaca aactgtttac ccgcattgag acaatgctcg gtatggcacc gaataccctg   1260

aaaatgggca ttatggatga agaacgtcgg acctcgctga acttgcgtag ctgtatcgct   1320

caggcgcgca accgcgtggc gttcatcaat accggtttcc tcgaccgtac cggcgatgaa   1380

atgcattcgg tgatggaagc tggcccgatg ctgcgtaaaa atcagatgaa atcgacgcct   1440

tggatcaaag cctacgagcg taataacgtg ctttccggtc tgttctgtgg gctgcgcggt   1500

aaagcgcaaa ttggtaaagg catgtgggca atgccggacc tgatggcaga catgtacagc   1560

cagaagggcg accaactgcg tgccggggca aacacagcct gggttccgtc accaaccgct   1620

gctacgctcc atgcgctgca ctaccaccaa accaacgtac agagcgtaca agccaacatt   1680

gcccagaccg agttcaatgc tgaatttgaa ccgctgctgg acgatctgct gactattccg   1740

gttgctgaaa acgctaactg gtcggcgcaa gagatccaac aagagctgga taacaacgtg   1800

caggggattc tggggtacgt ggtgcgctgg gtggagcagg ggattggttg ttcaaaagtg   1860

ccggatattc acaatgtggc gttgatggaa gaccgcgcaa cgctgcgtat ctccagccag   1920
```

```
catatcgcca actggttacg tcacggtatt ctgaccaaag aacaggtgca ggcgtcgctg   1980

gagaatatgg cgaaagtggt tgatcagcaa aacgctggcg atccggctta tcgtccgatg   2040

gcggggaatt tcgctaactc gtgtgctttt aaagctgcca gcgatttaat cttcctcggc   2100

gtgaaacagc caaacggcta taccgaaccg ttattacacg cctggcgttt acgcgaaaaa   2160

gaaagtcatt aa                                                        2172


<210> SEQ ID NO 48
<211> LENGTH: 723
<212> TYPE: PRT
<213> ORGANISM: Escherichia coli

<400> SEQUENCE: 48

Met Ser Gln Thr Ile Thr Gln Ser Arg Leu Arg Ile Asp Ala Asn Phe
1               5                   10                  15

Lys Arg Phe Val Asp Glu Glu Val Leu Pro Gly Thr Gly Leu Asp Ala
            20                  25                  30

Ala Ala Phe Trp Arg Asn Phe Asp Glu Ile Val His Asp Leu Ala Pro
        35                  40                  45

Glu Asn Arg Gln Leu Leu Ala Glu Arg Asp Arg Ile Gln Ala Ala Leu
    50                  55                  60

Asp Glu Trp His Arg Ser Asn Pro Gly Pro Val Lys Asp Lys Ala Ala
65                  70                  75                  80

Tyr Lys Ser Phe Leu Arg Glu Leu Gly Tyr Leu Val Pro Gln Pro Glu
                85                  90                  95

Arg Val Thr Val Glu Thr Thr Gly Ile Asp Ser Glu Ile Thr Ser Gln
            100                 105                 110

Ala Gly Pro Gln Leu Val Val Pro Ala Met Asn Ala Arg Tyr Ala Leu
        115                 120                 125

Asn Ala Ala Asn Ala Arg Trp Gly Ser Leu Tyr Asp Ala Leu Tyr Gly
    130                 135                 140

Ser Asp Ile Ile Pro Gln Glu Gly Ala Met Val Ser Gly Tyr Asp Pro
145                 150                 155                 160

Gln Arg Gly Glu Gln Val Ile Ala Trp Val Arg Arg Phe Leu Asp Glu
                165                 170                 175

Ser Leu Pro Leu Glu Asn Gly Ser Tyr Gln Asp Val Val Ala Phe Lys
            180                 185                 190

Val Val Asp Lys Gln Leu Arg Ile Gln Leu Lys Asn Gly Lys Glu Thr
        195                 200                 205

Thr Leu Arg Thr Pro Ala Gln Phe Val Gly Tyr Arg Gly Asp Ala Ala
    210                 215                 220

Ala Pro Thr Cys Ile Leu Leu Lys Asn Asn Gly Leu His Ile Glu Leu
225                 230                 235                 240

Gln Ile Asp Ala Asn Gly Arg Ile Gly Lys Asp Asp Pro Ala His Ile
                245                 250                 255

Asn Asp Val Ile Val Glu Ala Ala Ile Ser Thr Ile Leu Asp Cys Glu
            260                 265                 270

Asp Ser Val Ala Ala Val Asp Ala Glu Asp Lys Ile Leu Leu Tyr Arg
        275                 280                 285

Asn Leu Leu Gly Leu Met Gln Gly Thr Leu Gln Glu Lys Met Glu Lys
    290                 295                 300

Asn Gly Arg Gln Ile Val Arg Lys Leu Asn Asp Asp Arg His Tyr Thr
305                 310                 315                 320

Ala Ala Asp Gly Ser Glu Ile Ser Leu His Gly Arg Ser Leu Leu Phe
```

-continued

```
                325                 330                 335

Ile Arg Asn Val Gly His Leu Met Thr Ile Pro Val Ile Trp Asp Ser
            340                 345                 350

Glu Gly Asn Glu Ile Pro Glu Gly Ile Leu Asp Gly Val Met Thr Gly
        355                 360                 365

Ala Ile Ala Leu Tyr Asp Leu Lys Val Gln Lys Asn Ser Arg Thr Gly
    370                 375                 380

Ser Val Tyr Ile Val Lys Pro Lys Met His Gly Pro Gln Glu Val Ala
385                 390                 395                 400

Phe Ala Asn Lys Leu Phe Thr Arg Ile Glu Thr Met Leu Gly Met Ala
                405                 410                 415

Pro Asn Thr Leu Lys Met Gly Ile Met Asp Glu Glu Arg Arg Thr Ser
            420                 425                 430

Leu Asn Leu Arg Ser Cys Ile Ala Gln Ala Arg Asn Arg Val Ala Phe
        435                 440                 445

Ile Asn Thr Gly Phe Leu Asp Arg Thr Gly Asp Glu Met His Ser Val
    450                 455                 460

Met Glu Ala Gly Pro Met Leu Arg Lys Asn Gln Met Lys Ser Thr Pro
465                 470                 475                 480

Trp Ile Lys Ala Tyr Glu Arg Asn Asn Val Leu Ser Gly Leu Phe Cys
                485                 490                 495

Gly Leu Arg Gly Lys Ala Gln Ile Gly Lys Gly Met Trp Ala Met Pro
            500                 505                 510

Asp Leu Met Ala Asp Met Tyr Ser Gln Lys Gly Asp Gln Leu Arg Ala
        515                 520                 525

Gly Ala Asn Thr Ala Trp Val Pro Ser Pro Thr Ala Ala Thr Leu His
    530                 535                 540

Ala Leu His Tyr His Gln Thr Asn Val Gln Ser Val Gln Ala Asn Ile
545                 550                 555                 560

Ala Gln Thr Glu Phe Asn Ala Glu Phe Glu Pro Leu Leu Asp Asp Leu
                565                 570                 575

Leu Thr Ile Pro Val Ala Glu Asn Ala Asn Trp Ser Ala Gln Glu Ile
            580                 585                 590

Gln Gln Glu Leu Asp Asn Asn Val Gln Gly Ile Leu Gly Tyr Val Val
        595                 600                 605

Arg Trp Val Glu Gln Gly Ile Gly Cys Ser Lys Val Pro Asp Ile His
    610                 615                 620

Asn Val Ala Leu Met Glu Asp Arg Ala Thr Leu Arg Ile Ser Ser Gln
625                 630                 635                 640

His Ile Ala Asn Trp Leu Arg His Gly Ile Leu Thr Lys Glu Gln Val
                645                 650                 655

Gln Ala Ser Leu Glu Asn Met Ala Lys Val Val Asp Gln Gln Asn Ala
            660                 665                 670

Gly Asp Pro Ala Tyr Arg Pro Met Ala Gly Asn Phe Ala Asn Ser Cys
        675                 680                 685

Ala Phe Lys Ala Ala Ser Asp Leu Ile Phe Leu Gly Val Lys Gln Pro
    690                 695                 700

Asn Gly Tyr Thr Glu Pro Leu Leu His Ala Trp Arg Leu Arg Glu Lys
705                 710                 715                 720

Glu Ser His
```

<210> SEQ ID NO 49
<211> LENGTH: 1782

<212> TYPE: DNA
<213> ORGANISM: Escherichia coli

<400> SEQUENCE: 49

```
atggcaaaaa tgagagccgt tgacgcggca atgtatgtgc tggagaaaga aggtatcact     60
accgccttcg gtgttccggg agctgcaatc aatccgttct actcagcgat gcgtaagcac    120
ggcggtattc gtcacattct ggcgcgtcat gtggaaggtg cttcgcacat ggcggaaggt    180
tatacccgcg caacggcagg gaatatcggc gtatgtctgg ggacttccgg tcctgcgggc    240
acggacatga tcaccgcgct ctattccgct tctgctgatt ccattcctat tctgtgcatt    300
accggccagg caccgcgcgc ccgtctgcat aaagaagatt ttcaggccgt agatattgaa    360
gcaattgcta aaccggtcag caaaatggcg gttacagttc gtgaagcggc gctggtgcct    420
cgcgtgctgc aacaggcatt tcacctgatg cgttctggtc gtccgggtcc ggtactggtg    480
gatttaccgt tcgacgttca ggttgcggaa atcgagtttg atcctgacat gtacgaaccg    540
ctgccggtct acaaacctgc tgccagccgt atgcagatcg aaaaagctgt agaaatgtta    600
atccaggccg aacgtccggt gattgttgcc gggggcgggg taattaatgc tgacgcagct    660
gcactgttac aacagtttgc tgaactgacc agcgttccgg tgatcccaac gctaatgggc    720
tggggctgta tcccggacga tcatgaactg atggccggga tggtgggtct gcaaaccgcg    780
catcgttacg gtaacgcaac gctgctggcg tctgacatgg tgtttggtat cggtaaccgt    840
tttgctaacc gtcataccgg ctcggtagag aaatacaccg aagggcgcaa aatcgttcat    900
attgatattg agccgacgca aattggtcgc gtgctgtgtc cggatctcgg tattgtctct    960
gatgctaaag cggcgctgac actgctggtt gaagtggcgc aggagatgca aaaagcgggt   1020
cgtctgccgt gtcgtaaaga atgggtcgcc gactgccagc agcgtaaacg cactttgctg   1080
cgcaaaaccc acttcgacaa cgtgccggtg aaaccgcagc gcgtgtatga agagatgaac   1140
aaagcctttg gtcgcgatgt ttgttatgtc accaccattg gtctgtcaca aatcgctgcg   1200
gcacaaatgc tgcatgtctt taaagaccgc cactggatca actgtggtca ggctggtccg   1260
ttaggctgga cgattccggc tgcgctaggg gtttgtgccg ctgatccgaa acgcaatgtg   1320
gtggcgattt ctggcgactt tgacttccag ttcctgattg aagagttagc tgttggcgcg   1380
cagttcaaca ttccgtacat ccatgtgctg gtcaacaacg cttatctggg gctgattcgt   1440
cagtcacaac gcgcttttga catggactac tgcgtgcaac tcgctttcga gaatatcaac   1500
tccagtgaag tgaatggcta cggtgttgac cacgtaaaag tagcggaagg tttaggttgt   1560
aaagctattc gggtcttcaa accggaagat attgcgccag cctttgaaca ggcgaaagcc   1620
ttaatggcgc aatatcgggt accggtagtc gtggaagtta ttctcgagcg tgtgaccaat   1680
atttcgatgg gcagcgaact ggataacgtc atggaatttg aagatatcgc cgataacgca   1740
gcggacgcac cgactgaaac ctgcttcatg cactatgaat aa                      1782
```

<210> SEQ ID NO 50
<211> LENGTH: 593
<212> TYPE: PRT
<213> ORGANISM: Escherichia coli

<400> SEQUENCE: 50

```
Met Ala Lys Met Arg Ala Val Asp Ala Ala Met Tyr Val Leu Glu Lys
1               5                   10                  15

Glu Gly Ile Thr Thr Ala Phe Gly Val Pro Gly Ala Ala Ile Asn Pro
            20                  25                  30
```

```
Phe Tyr Ser Ala Met Arg Lys His Gly Gly Ile Arg His Ile Leu Ala
        35                  40                  45

Arg His Val Glu Gly Ala Ser His Met Ala Glu Gly Tyr Thr Arg Ala
    50                  55                  60

Thr Ala Gly Asn Ile Gly Val Cys Leu Gly Thr Ser Gly Pro Ala Gly
65                  70                  75                  80

Thr Asp Met Ile Thr Ala Leu Tyr Ser Ala Ser Ala Asp Ser Ile Pro
                85                  90                  95

Ile Leu Cys Ile Thr Gly Gln Ala Pro Arg Ala Arg Leu His Lys Glu
            100                 105                 110

Asp Phe Gln Ala Val Asp Ile Glu Ala Ile Ala Lys Pro Val Ser Lys
        115                 120                 125

Met Ala Val Thr Val Arg Glu Ala Ala Leu Val Pro Arg Val Leu Gln
    130                 135                 140

Gln Ala Phe His Leu Met Arg Ser Gly Arg Pro Gly Pro Val Leu Val
145                 150                 155                 160

Asp Leu Pro Phe Asp Val Gln Val Ala Glu Ile Glu Phe Asp Pro Asp
                165                 170                 175

Met Tyr Glu Pro Leu Pro Val Tyr Lys Pro Ala Ala Ser Arg Met Gln
            180                 185                 190

Ile Glu Lys Ala Val Glu Met Leu Ile Gln Ala Glu Arg Pro Val Ile
        195                 200                 205

Val Ala Gly Gly Gly Val Ile Asn Ala Asp Ala Ala Ala Leu Leu Gln
    210                 215                 220

Gln Phe Ala Glu Leu Thr Ser Val Pro Val Ile Pro Thr Leu Met Gly
225                 230                 235                 240

Trp Gly Cys Ile Pro Asp Asp His Glu Leu Met Ala Gly Met Val Gly
                245                 250                 255

Leu Gln Thr Ala His Arg Tyr Gly Asn Ala Thr Leu Leu Ala Ser Asp
            260                 265                 270

Met Val Phe Gly Ile Gly Asn Arg Phe Ala Asn Arg His Thr Gly Ser
        275                 280                 285

Val Glu Lys Tyr Thr Glu Gly Arg Lys Ile Val His Ile Asp Ile Glu
    290                 295                 300

Pro Thr Gln Ile Gly Arg Val Leu Cys Pro Asp Leu Gly Ile Val Ser
305                 310                 315                 320

Asp Ala Lys Ala Ala Leu Thr Leu Leu Val Glu Val Ala Gln Glu Met
                325                 330                 335

Gln Lys Ala Gly Arg Leu Pro Cys Arg Lys Glu Trp Val Ala Asp Cys
            340                 345                 350

Gln Gln Arg Lys Arg Thr Leu Leu Arg Lys Thr His Phe Asp Asn Val
        355                 360                 365

Pro Val Lys Pro Gln Arg Val Tyr Glu Glu Met Asn Lys Ala Phe Gly
    370                 375                 380

Arg Asp Val Cys Tyr Val Thr Thr Ile Gly Leu Ser Gln Ile Ala Ala
385                 390                 395                 400

Ala Gln Met Leu His Val Phe Lys Asp Arg His Trp Ile Asn Cys Gly
                405                 410                 415

Gln Ala Gly Pro Leu Gly Trp Thr Ile Pro Ala Ala Leu Gly Val Cys
            420                 425                 430

Ala Ala Asp Pro Lys Arg Asn Val Val Ala Ile Ser Gly Asp Phe Asp
        435                 440                 445

Phe Gln Phe Leu Ile Glu Glu Leu Ala Val Gly Ala Gln Phe Asn Ile
```

```
    450                 455                 460

Pro Tyr Ile His Val Leu Val Asn Asn Ala Tyr Leu Gly Leu Ile Arg
465                 470                 475                 480

Gln Ser Gln Arg Ala Phe Asp Met Asp Tyr Cys Val Gln Leu Ala Phe
                485                 490                 495

Glu Asn Ile Asn Ser Ser Glu Val Asn Gly Tyr Gly Val Asp His Val
            500                 505                 510

Lys Val Ala Glu Gly Leu Gly Cys Lys Ala Ile Arg Val Phe Lys Pro
        515                 520                 525

Glu Asp Ile Ala Pro Ala Phe Glu Gln Ala Lys Ala Leu Met Ala Gln
    530                 535                 540

Tyr Arg Val Pro Val Val Val Glu Val Ile Leu Glu Arg Val Thr Asn
545                 550                 555                 560

Ile Ser Met Gly Ser Glu Leu Asp Asn Val Met Glu Phe Glu Asp Ile
                565                 570                 575

Ala Asp Asn Ala Ala Asp Ala Pro Thr Glu Thr Cys Phe Met His Tyr
            580                 585                 590

Glu


<210> SEQ ID NO 51
<211> LENGTH: 243
<212> TYPE: DNA
<213> ORGANISM: Escherichia coli

<400> SEQUENCE: 51

atgaagaaac cgctccgcca gcaaaaccgc cagattatta gctatgtccc acgcacggaa      60

cccgcgccgc cagaacatgc gataaagatg gattcgtttc gtgatgtctg gatgctgcgt     120

ggcaaatatg ttgcgtttgt actgatggga gagtcatttc tgcgctcacc ggcgtttact     180

gtgcctgaat ctgcccaacg ttgggcaaat cagatccgcc aggaagggga agtgactgag     240

taa                                                                   243


<210> SEQ ID NO 52
<211> LENGTH: 80
<212> TYPE: PRT
<213> ORGANISM: Escherichia coli

<400> SEQUENCE: 52

Met Lys Lys Pro Leu Arg Gln Gln Asn Arg Gln Ile Ile Ser Tyr Val
1               5                   10                  15

Pro Arg Thr Glu Pro Ala Pro Pro Glu His Ala Ile Lys Met Asp Ser
            20                  25                  30

Phe Arg Asp Val Trp Met Leu Arg Gly Lys Tyr Val Ala Phe Val Leu
        35                  40                  45

Met Gly Glu Ser Phe Leu Arg Ser Pro Ala Phe Thr Val Pro Glu Ser
    50                  55                  60

Ala Gln Arg Trp Ala Asn Gln Ile Arg Gln Glu Gly Glu Val Thr Glu
65                  70                  75                  80


<210> SEQ ID NO 53
<211> LENGTH: 1500
<212> TYPE: DNA
<213> ORGANISM: Escherichia coli

<400> SEQUENCE: 53

atgagcatct tgtacgaaga gcgtcttgat ggcgctttac ccgatgtcga ccgcacatcg      60
```

-continued

```
gtactgatgg cactgcgtga gcatgtccct ggacttgaga tcctgcatac cgatgaggag    120
atcattcctt acgagtgtga cgggttgagc gcgtatcgca cgcgtccatt actggttgtt    180
ctgcctaagc aaatggaaca ggtgacagcg attctggctg tctgccatcg cctgcgtgta    240
ccggtggtga cccgtggtgc aggcaccggg ctttctggtg gcgcgctgcc gctggaaaaa    300
ggtgtgttgt tggtgatggc gcgctttaaa gagatcctcg acattaaccc cgttggtcgc    360
cgcgcgcgcg tgcagccagg cgtgcgtaac ctggcgatct cccaggccgt tgcaccgcat    420
aatctctact acgcaccgga cccttcctca caaatcgcct gttccattgg cggcaatgtg    480
gctgaaaatg ccggcggcgt ccactgcctg aaatatggtc tgaccgtaca taacctgctg    540
aaaattgaag tgcaaacgct ggacggcgag gcactgacgc ttggatcgga cgcgctggat    600
tcacctggtt ttgacctgct ggcgctgttc accggatcgg aaggtatgct cggcgtgacc    660
accgaagtga cggtaaaact gctgccgaag ccgcccgtgg cgcgggttct gttagccagc    720
tttgactcgg tagaaaaagc cggacttgcg gttggtgaca tcatcgccaa tggcattatc    780
cccggcgggc tggagatgat ggataacctg tcgatccgcg cggcggaaga ttttattcat    840
gccggttatc ccgtcgacgc cgaagcgatt ttgttatgcg agctggacgg cgtggagtct    900
gacgtacagg aagactgcga gcgggttaac gacatcttgt tgaaagcggg cgcgactgac    960
gtccgtctgg cacaggacga agcagagcgc gtacgtttct gggccggtcg caaaaatgcg   1020
ttcccggcgg taggacgtat ctccccggat tactactgca tggatggcac catcccgcgt   1080
cgcgccctgc ctggcgtact ggaaggcatt gcccgtttat cgcagcaata tgatttacgt   1140
gttgccaacg tctttcatgc cggagatggc aacatgcacc cgttaatcct tttcgatgcc   1200
aacgaacccg gtgaatttgc ccgcgcggaa gagctgggcg ggaagatcct cgaactctgc   1260
gttgaagttg gcggcagcat cagtggcgaa catggcatcg ggcgagaaaa aatcaatcaa   1320
atgtgcgccc agttcaacag cgatgaaatc acgaccttcc atgcggtcaa ggcggcgttt   1380
gaccccgatg gtttgctgaa ccctgggaaa aacattccca cgctacaccg ctgtgctgaa   1440
tttggtgcca tgcatgtgca tcacggtcat ttacctttcc ctgaactgga gcgtttctga   1500
```

<210> SEQ ID NO 54
<211> LENGTH: 499
<212> TYPE: PRT
<213> ORGANISM: Escherichia coli

<400> SEQUENCE: 54

```
Met Ser Ile Leu Tyr Glu Glu Arg Leu Asp Gly Ala Leu Pro Asp Val
1               5                   10                  15

Asp Arg Thr Ser Val Leu Met Ala Leu Arg Glu His Val Pro Gly Leu
            20                  25                  30

Glu Ile Leu His Thr Asp Glu Glu Ile Ile Pro Tyr Glu Cys Asp Gly
        35                  40                  45

Leu Ser Ala Tyr Arg Thr Arg Pro Leu Leu Val Val Leu Pro Lys Gln
    50                  55                  60

Met Glu Gln Val Thr Ala Ile Leu Ala Val Cys His Arg Leu Arg Val
65                  70                  75                  80

Pro Val Val Thr Arg Gly Ala Gly Thr Gly Leu Ser Gly Gly Ala Leu
                85                  90                  95

Pro Leu Glu Lys Gly Val Leu Leu Val Met Ala Arg Phe Lys Glu Ile
            100                 105                 110

Leu Asp Ile Asn Pro Val Gly Arg Arg Ala Arg Val Gln Pro Gly Val
        115                 120                 125
```

```
Arg Asn Leu Ala Ile Ser Gln Ala Val Ala Pro His Asn Leu Tyr Tyr
    130                 135                 140

Ala Pro Asp Pro Ser Ser Gln Ile Ala Cys Ser Ile Gly Gly Asn Val
145                 150                 155                 160

Ala Glu Asn Ala Gly Gly Val His Cys Leu Lys Tyr Gly Leu Thr Val
                165                 170                 175

His Asn Leu Leu Lys Ile Glu Val Gln Thr Leu Asp Gly Glu Ala Leu
            180                 185                 190

Thr Leu Gly Ser Asp Ala Leu Asp Ser Pro Gly Phe Asp Leu Leu Ala
        195                 200                 205

Leu Phe Thr Gly Ser Glu Gly Met Leu Gly Val Thr Thr Glu Val Thr
    210                 215                 220

Val Lys Leu Leu Pro Lys Pro Pro Val Ala Arg Val Leu Leu Ala Ser
225                 230                 235                 240

Phe Asp Ser Val Glu Lys Ala Gly Leu Ala Val Gly Asp Ile Ile Ala
                245                 250                 255

Asn Gly Ile Ile Pro Gly Gly Leu Glu Met Met Asp Asn Leu Ser Ile
            260                 265                 270

Arg Ala Ala Glu Asp Phe Ile His Ala Gly Tyr Pro Val Asp Ala Glu
        275                 280                 285

Ala Ile Leu Leu Cys Glu Leu Asp Gly Val Glu Ser Asp Val Gln Glu
    290                 295                 300

Asp Cys Glu Arg Val Asn Asp Ile Leu Leu Lys Ala Gly Ala Thr Asp
305                 310                 315                 320

Val Arg Leu Ala Gln Asp Glu Ala Glu Arg Val Arg Phe Trp Ala Gly
                325                 330                 335

Arg Lys Asn Ala Phe Pro Ala Val Gly Arg Ile Ser Pro Asp Tyr Tyr
            340                 345                 350

Cys Met Asp Gly Thr Ile Pro Arg Arg Ala Leu Pro Gly Val Leu Glu
        355                 360                 365

Gly Ile Ala Arg Leu Ser Gln Gln Tyr Asp Leu Arg Val Ala Asn Val
    370                 375                 380

Phe His Ala Gly Asp Gly Asn Met His Pro Leu Ile Leu Phe Asp Ala
385                 390                 395                 400

Asn Glu Pro Gly Glu Phe Ala Arg Ala Glu Glu Leu Gly Gly Lys Ile
                405                 410                 415

Leu Glu Leu Cys Val Glu Val Gly Gly Ser Ile Ser Gly Glu His Gly
            420                 425                 430

Ile Gly Arg Glu Lys Ile Asn Gln Met Cys Ala Gln Phe Asn Ser Asp
        435                 440                 445

Glu Ile Thr Thr Phe His Ala Val Lys Ala Ala Phe Asp Pro Asp Gly
    450                 455                 460

Leu Leu Asn Pro Gly Lys Asn Ile Pro Thr Leu His Arg Cys Ala Glu
465                 470                 475                 480

Phe Gly Ala Met His Val His His Gly His Leu Pro Phe Pro Glu Leu
                485                 490                 495

Glu Arg Phe


<210> SEQ ID NO 55
<211> LENGTH: 1053
<212> TYPE: DNA
<213> ORGANISM: Escherichia coli

<400> SEQUENCE: 55
```

```
atgctacgcg agtgtgatta cagccaggcg ctgctggagc aggtgaatca ggcgattagc      60

gataaaacgc cgctggtgat tcagggcagc aatagcaaag ccttttttagg tcgccctgtc    120

accgggcaaa cgctggatgt tcgttgtcat cgcggcattg ttaattacga cccgaccgag    180

ctggtgataa ccgcgcgtgt cggaacgccg ctggtgacaa ttgaagcggc gctggaaagc    240

gcggggcaaa tgctccccctg tgagccgccg cattatggtg aagaagccac ctggggcggg    300

atggtcgcct gcgggctggc ggggccgcgt cgcccgtgga gcggttcggt ccgcgatttt    360

gtcctcggca cgcgcatcat taccggcgct ggaaaacatc tgcgttttgg tggcgaagtg    420

atgaaaaacg ttgccggata cgatctctca cggttaatgg tcggaagcta cggttgtctt    480

ggcgtgctca ctgaaatctc aatgaaagtg ttaccgcgac cgcgcgcctc cctgagcctg    540

cgtcgggaaa tcagcctgca agaagccatg agtgaaatcg ccgagtggca actccagcca    600

ttacccatta gtggcttatg ttacttcgac aatgcgttgt ggatccgcct tgagggcggc    660

gaaggatcgg taaaagcagc gcgtgaactg ctgggtggcg aagaggttgc cggtcagttc    720

tggcagcaat tgcgtgaaca acaactgccg ttcttctcgt taccaggtac cttatggcgc    780

atttcattac ccagtgatgc gccgatgatg gatttacccg gcgagcaact gatcgactgg    840

ggcggggcgt tacgctggct gaaatcgaca gccgaggaca atcaaatcca tcgcatcgcc    900

cgcaacgctg gcggtcatgc gacccgcttt agtgccggag atggtggctt tgccccgcta    960

tcggctcctt tattccgcta tcaccagcag cttaaacagc agctcgaccc ttgcggcgtg   1020

tttaaccccg gtcgcatgta cgcggaactt tga                                1053
```

<210> SEQ ID NO 56
<211> LENGTH: 350
<212> TYPE: PRT
<213> ORGANISM: Escherichia coli

<400> SEQUENCE: 56

```
Met Leu Arg Glu Cys Asp Tyr Ser Gln Ala Leu Leu Glu Gln Val Asn
1               5                   10                  15

Gln Ala Ile Ser Asp Lys Thr Pro Leu Val Ile Gln Gly Ser Asn Ser
            20                  25                  30

Lys Ala Phe Leu Gly Arg Pro Val Thr Gly Gln Thr Leu Asp Val Arg
        35                  40                  45

Cys His Arg Gly Ile Val Asn Tyr Asp Pro Thr Glu Leu Val Ile Thr
    50                  55                  60

Ala Arg Val Gly Thr Pro Leu Val Thr Ile Glu Ala Ala Leu Glu Ser
65                  70                  75                  80

Ala Gly Gln Met Leu Pro Cys Glu Pro Pro His Tyr Gly Glu Glu Ala
                85                  90                  95

Thr Trp Gly Gly Met Val Ala Cys Gly Leu Ala Gly Pro Arg Arg Pro
            100                 105                 110

Trp Ser Gly Ser Val Arg Asp Phe Val Leu Gly Thr Arg Ile Ile Thr
        115                 120                 125

Gly Ala Gly Lys His Leu Arg Phe Gly Gly Glu Val Met Lys Asn Val
    130                 135                 140

Ala Gly Tyr Asp Leu Ser Arg Leu Met Val Gly Ser Tyr Gly Cys Leu
145                 150                 155                 160

Gly Val Leu Thr Glu Ile Ser Met Lys Val Leu Pro Arg Pro Arg Ala
                165                 170                 175

Ser Leu Ser Leu Arg Arg Glu Ile Ser Leu Gln Glu Ala Met Ser Glu
```

```
            180                 185                 190

Ile Ala Glu Trp Gln Leu Gln Pro Leu Pro Ile Ser Gly Leu Cys Tyr
        195                 200                 205

Phe Asp Asn Ala Leu Trp Ile Arg Leu Glu Gly Gly Glu Gly Ser Val
    210                 215                 220

Lys Ala Ala Arg Glu Leu Leu Gly Gly Glu Glu Val Ala Gly Gln Phe
225                 230                 235                 240

Trp Gln Gln Leu Arg Glu Gln Gln Leu Pro Phe Phe Ser Leu Pro Gly
                245                 250                 255

Thr Leu Trp Arg Ile Ser Leu Pro Ser Asp Ala Pro Met Met Asp Leu
            260                 265                 270

Pro Gly Glu Gln Leu Ile Asp Trp Gly Gly Ala Leu Arg Trp Leu Lys
        275                 280                 285

Ser Thr Ala Glu Asp Asn Gln Ile His Arg Ile Ala Arg Asn Ala Gly
    290                 295                 300

Gly His Ala Thr Arg Phe Ser Ala Gly Asp Gly Gly Phe Ala Pro Leu
305                 310                 315                 320

Ser Ala Pro Leu Phe Arg Tyr His Gln Gln Leu Lys Gln Gln Leu Asp
                325                 330                 335

Pro Cys Gly Val Phe Asn Pro Gly Arg Met Tyr Ala Glu Leu
            340                 345                 350


<210> SEQ ID NO 57
<211> LENGTH: 1224
<212> TYPE: DNA
<213> ORGANISM: Escherichia coli

<400> SEQUENCE: 57

atgcaaaccc aattaactga agagatgcgg cagaacgcgc gcgcgctgga agccgacagc      60

atcctgcgcg cctgtgttca ctgcggattt tgtaccgcaa cctgcccaac ctatcagctt     120

ctgggcgatg aactggacgg gccgcgcggg cgcatctatc tgattaaaca ggtgctggaa     180

ggcaacgaag tcacgcttaa aacacaggag catctcgatc gctgcctcac ttgccgtaat     240

tgtgaaacca cctgtccttc tggtgtgcgc tatcacaatt tgctggatat cgggcgtgat     300

attgtcgagc agaaagtgaa acgcccactg ccggagcgaa tactgcgcga aggattgcgc     360

caggtagtgc cgcgtccggc ggtcttccgt gcgctgacgc aggtagggct ggtgctgcga     420

ccgtttttac cggaacaggt cagagcaaaa ctgcctgctg aaacggtgaa agctaaaccg     480

cgtccgccgc tgcgccataa gcgtcgggtt ttaatgttgg aaggctgcgc ccagcctacg     540

ctttcgccca acaccaacgc ggcaactgcg cgagtgctgg atcgtctggg gatcagcgtc     600

atgccagcta acgaagcagg ctgttgtggc gcggtggact atcatcttaa tgcgcaggag     660

aaagggctgg cacgggcgcg caataatatt gatgcctggt ggcccgcgat tgaagcaggt     720

gccgaggcaa ttttgcaaac cgccagcggc tgcggcgcgt ttgtcaaaga gtatgggcag     780

atgctgaaaa acgatgcgtt atatgccgat aaagcacgtc aggtcagtga actggcggtc     840

gatttagtcg aacttctgcg cgaggaaccg ctggaaaaac tggcaattcg cggcgataaa     900

aagctggcct tccactgtcc gtgtaccct a caacatgcgc aaaagctgaa cggcgaagtg     960

gaaaaagtgt tgcttcgtct tggatttacc ttaacggacg ttcccgacag ccatctgtgc    1020

tgcggttcag cgggaacata tgcgttaacg catcccgatc tggcacgcca gctgcgggat    1080

aacaaaatga atgcgctgga aagcggcaaa ccggaaatga tcgtcaccgc caacattggt    1140

tgccagacgc atctggcgag cgccggtcgt acctctgtgc gtcactggat tgaaattgta    1200
```

gaacaagccc ttgaaaagga ataa 1224

<210> SEQ ID NO 58
<211> LENGTH: 407
<212> TYPE: PRT
<213> ORGANISM: Escherichia coli

<400> SEQUENCE: 58

```
Met Gln Thr Gln Leu Thr Glu Glu Met Arg Gln Asn Ala Arg Ala Leu
1               5                   10                  15

Glu Ala Asp Ser Ile Leu Arg Ala Cys Val His Cys Gly Phe Cys Thr
            20                  25                  30

Ala Thr Cys Pro Thr Tyr Gln Leu Leu Gly Asp Glu Leu Asp Gly Pro
        35                  40                  45

Arg Gly Arg Ile Tyr Leu Ile Lys Gln Val Leu Glu Gly Asn Glu Val
    50                  55                  60

Thr Leu Lys Thr Gln Glu His Leu Asp Arg Cys Leu Thr Cys Arg Asn
65                  70                  75                  80

Cys Glu Thr Thr Cys Pro Ser Gly Val Arg Tyr His Asn Leu Leu Asp
                85                  90                  95

Ile Gly Arg Asp Ile Val Glu Gln Lys Val Lys Arg Pro Leu Pro Glu
            100                 105                 110

Arg Ile Leu Arg Glu Gly Leu Arg Gln Val Val Pro Arg Pro Ala Val
        115                 120                 125

Phe Arg Ala Leu Thr Gln Val Gly Leu Val Leu Arg Pro Phe Leu Pro
    130                 135                 140

Glu Gln Val Arg Ala Lys Leu Pro Ala Glu Thr Val Lys Ala Lys Pro
145                 150                 155                 160

Arg Pro Pro Leu Arg His Lys Arg Arg Val Leu Met Leu Glu Gly Cys
                165                 170                 175

Ala Gln Pro Thr Leu Ser Pro Asn Thr Asn Ala Ala Thr Ala Arg Val
            180                 185                 190

Leu Asp Arg Leu Gly Ile Ser Val Met Pro Ala Asn Glu Ala Gly Cys
        195                 200                 205

Cys Gly Ala Val Asp Tyr His Leu Asn Ala Gln Glu Lys Gly Leu Ala
    210                 215                 220

Arg Ala Arg Asn Asn Ile Asp Ala Trp Trp Pro Ala Ile Glu Ala Gly
225                 230                 235                 240

Ala Glu Ala Ile Leu Gln Thr Ala Ser Gly Cys Gly Ala Phe Val Lys
                245                 250                 255

Glu Tyr Gly Gln Met Leu Lys Asn Asp Ala Leu Tyr Ala Asp Lys Ala
            260                 265                 270

Arg Gln Val Ser Glu Leu Ala Val Asp Leu Val Glu Leu Leu Arg Glu
        275                 280                 285

Glu Pro Leu Glu Lys Leu Ala Ile Arg Gly Asp Lys Lys Leu Ala Phe
    290                 295                 300

His Cys Pro Cys Thr Leu Gln His Ala Gln Lys Leu Asn Gly Glu Val
305                 310                 315                 320

Glu Lys Val Leu Leu Arg Leu Gly Phe Thr Leu Thr Asp Val Pro Asp
                325                 330                 335

Ser His Leu Cys Cys Gly Ser Ala Gly Thr Tyr Ala Leu Thr His Pro
            340                 345                 350

Asp Leu Ala Arg Gln Leu Arg Asp Asn Lys Met Asn Ala Leu Glu Ser
        355                 360                 365
```

Gly Lys Pro Glu Met Ile Val Thr Ala Asn Ile Gly Cys Gln Thr His
    370                 375                 380

Leu Ala Ser Ala Gly Arg Thr Ser Val Arg His Trp Ile Glu Ile Val
385                 390                 395                 400

Glu Gln Ala Leu Glu Lys Glu
                405

<210> SEQ ID NO 59
<211> LENGTH: 405
<212> TYPE: DNA
<213> ORGANISM: Escherichia coli

<400> SEQUENCE: 59
atgaaaacta aagtcattct tagccagcaa atggcgagtg caattattgc cgcaggtcag 60
gaagaggcgc agaaaaataa ctggtctgtt tccattgctg ttgccgatga cggcggtcat 120
ctgctggcgt taagtcgcat ggacgattgc gcgccgattg cggcttatat ctcccaggag 180
aaagcgcgta ccgccgcgct ggggcgtcgt gaaactaagg gctatgaaga gatggtgaac 240
aacggacgta ccgcgttcgt gactgcgccg ttattaacgt cgctggaagg cggcgtaccg 300
gttgttgtgg atgggcaaat tattggtgcc gtgggcgttt ctggtttaac cggagcacag 360
gatgcgcagg tcgcgaaagc ggcagcagcg gtgttggcga aataa 405

<210> SEQ ID NO 60
<211> LENGTH: 134
<212> TYPE: PRT
<213> ORGANISM: Escherichia coli

<400> SEQUENCE: 60

Met Lys Thr Lys Val Ile Leu Ser Gln Gln Met Ala Ser Ala Ile Ile
1               5                   10                  15

Ala Ala Gly Gln Glu Glu Ala Gln Lys Asn Asn Trp Ser Val Ser Ile
            20                  25                  30

Ala Val Ala Asp Asp Gly Gly His Leu Leu Ala Leu Ser Arg Met Asp
        35                  40                  45

Asp Cys Ala Pro Ile Ala Ala Tyr Ile Ser Gln Glu Lys Ala Arg Thr
    50                  55                  60

Ala Ala Leu Gly Arg Arg Glu Thr Lys Gly Tyr Glu Glu Met Val Asn
65                  70                  75                  80

Asn Gly Arg Thr Ala Phe Val Thr Ala Pro Leu Leu Thr Ser Leu Glu
                85                  90                  95

Gly Gly Val Pro Val Val Val Asp Gly Gln Ile Ile Gly Ala Val Gly
            100                 105                 110

Val Ser Gly Leu Thr Gly Ala Gln Asp Ala Gln Val Ala Lys Ala Ala
        115                 120                 125

Ala Ala Val Leu Ala Lys
    130

<210> SEQ ID NO 61
<211> LENGTH: 1251
<212> TYPE: DNA
<213> ORGANISM: Escherichia coli

<400> SEQUENCE: 61
atggaaagta aagtagttgt tccggcacaa ggcaagaaga tcaccctgca aaacggcaaa 60
ctcaacgttc ctgaaaatcc gattatccct tacattgaag gtgatggaat cggtgtagat 120

```
gtaaccccag ccatgctgaa agtggtcgac gctgcagtcg agaaagccta taaaggcgag    180

cgtaaaatct cctggatgga aatttacacc ggtgaaaaat ccacacaggt ttatggtcag    240

gacgtctggc tgcctgctga aactcttgat ctgattcgtg aatatcgcgt tgccattaaa    300

ggtccgctga ccactccggt tggtggcggt attcgctctc tgaacgttgc cctgcgccag    360

gaactggatc tctacatctg cctgcgtccg gtacgttact atcagggcac tccaagcccg    420

gttaaacacc ctgaactgac cgatatggtt atcttccgtg aaaactcgga agacatttat    480

gcgggtatcg aatggaaagc agactctgcc gacgccgaga aagtgattaa attcctgcgt    540

gaagagatgg gggtgaagaa aattcgcttc ccggaacatt gtggtatcgg tattaagccg    600

tgttcggaag aaggcaccaa acgtctggtt cgtgcagcga tcgaatacgc aattgctaac    660

gatcgtgact ctgtgactct ggtgcacaaa ggcaacatca tgaagttcac cgaaggagcg    720

tttaaagact ggggctacca gctggcgcgt gaagagtttg gcggtgaact gatcgacggt    780

ggcccgtggc tgaaagttaa aaacccgaac actggcaaag agatcgtcat taaagacgtg    840

attgctgatg cattcctgca acagatcctg ctgcgtccgg ctgaatatga tgttatcgcc    900

tgtatgaacc tgaacggtga ctacatttct gacgccctgg cagcgcaggt tggcggtatc    960

ggtatcgccc ctggtgcaaa catcggtgac gaatgcgccc tgtttgaagc cacccacggt   1020

actgcgccga aatatgccgg tcaggacaaa gtaaatcctg gctctattat tctctccgct   1080

gagatgatgc tgcgccacat gggttggacc gaagcggctg acttaattgt taaaggtatg   1140

gaaggcgcaa tcaacgcgaa aaccgtaacc tatgacttcg agcgtctgat ggatggcgct   1200

aaactgctga aatgttcaga gtttggtgac gcgatcatcg aaaacatgta a            1251
```

<210> SEQ ID NO 62
<211> LENGTH: 416
<212> TYPE: PRT
<213> ORGANISM: Escherichia coli

<400> SEQUENCE: 62

```
Met Glu Ser Lys Val Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30

Glu Gly Asp Gly Ile Gly Val Asp Val Thr Pro Ala Met Leu Lys Val
        35                  40                  45

Val Asp Ala Ala Val Glu Lys Ala Tyr Lys Gly Glu Arg Lys Ile Ser
    50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
        115                 120                 125

Arg Pro Val Arg Tyr Tyr Gln Gly Thr Pro Ser Pro Val Lys His Pro
    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                165                 170                 175
```

```
Lys Phe Leu Arg Glu Glu Met Gly Val Lys Lys Ile Arg Phe Pro Glu
            180                 185                 190

His Cys Gly Ile Gly Ile Lys Pro Cys Ser Glu Glu Gly Thr Lys Arg
        195                 200                 205

Leu Val Arg Ala Ala Ile Glu Tyr Ala Ile Ala Asn Asp Arg Asp Ser
    210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
        275                 280                 285

Ile Leu Leu Arg Pro Ala Glu Tyr Asp Val Ile Ala Cys Met Asn Leu
    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
        355                 360                 365

Trp Thr Glu Ala Ala Asp Leu Ile Val Lys Gly Met Glu Gly Ala Ile
    370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                405                 410                 415
```

<210> SEQ ID NO 63
<211> LENGTH: 1737
<212> TYPE: DNA
<213> ORGANISM: Escherichia coli

<400> SEQUENCE: 63

```
atgccgcgtg gcctggaatt attgattgct caaaccattt tgcaaggctt cgatgctcag     60

tatggtcgat tcctcgaagt gacctccggt gcgcagcagc gtttcgaaca ggccgactgg    120

catgctgtcc agcaggcgat gaaaaaccgt atccatcttt acgatcatca cgttggtctg    180

gtcgtggagc aactgcgctg cattactaac ggccaaagta cggacgcggc atttttacta    240

cgtgttaaag agcattacac ccggctgttg ccggattacc cgcgcttcga gattgcggag    300

agctttttta actccgtgta ctgtcggtta tttgaccacc gctcgcttac tcccgagcgg    360

ctttttatct ttagctctca gccagagcgc cgctttcgta ccattccccg cccgctggcg    420

aaagactttc accccgatca cggctgggaa tctctactga tgcgcgttat cagcgaccta    480

ccgctgcgcc tgcgctggca gaataaaagc cgtgacatcc attacattat tcgccatctg    540

acggaaacgc tggggacaga caacctcgcg gaaagtcatt tacaggtggc gaacgaactg    600

ttttaccgca ataaagccgc ctggctggta ggcaaactga tcacaccttc cggcacattg    660

ccatttttgc tgccgatcca ccagacggac gacggcgagt tatttattga tacctgcctg    720

acgacgaccg ccgaagcgag cattgttttt ggctttgcgc gttcttattt tatggtttat    780
```

gcgccgctgc ccgcagcgct ggtcgagtgg ctacgggaaa ttctgccagg taaaaccacc 840
gctgaattgt atatggctat cggctgccag aagcacgcca aaaccgaaag ctaccgcgaa 900
tatctcgttt atctacaggg ctgtaatgag cagttcattg aagcgccggg tattcgtgga 960
atggtgatgt tggtgtttac gctgccgggc tttgatcggg tattcaaagt catcaaagac 1020
aggttcgcgc cgcagaaaga gatgtctgcc gctcacgttc gtgcctgcta tcaactggtg 1080
aaagagcacg atcgcgtggg ccgaatggcg gacacccagg agtttgaaaa ctttgtgctg 1140
gagaagcggc atatttcccc ggcattaatg gaattactgc ttcaggaagc agcggaaaaa 1200
atcaccgatc tcggcgaaca aattgtgatt cgccatcttt atattgagcg gcggatggtg 1260
ccgctcaata tctggctgga acaagtggaa ggtcagcagt tgcgcgacgc cattgaagaa 1320
tacggtaacg ctattcgcca gcttgccgct gctaacattt tccctggcga catgctgttt 1380
aaaaacttcg gtgtcacccg tcacgggcgt gtggtttttt atgattacga tgaaatttgc 1440
tacatgacgg aagtgaattt ccgcgacatc ccgccgccgc gctatccgga agacgaactt 1500
gccagcgaac cgtggtacag cgtctcgccg ggcgatgttt tcccggaaga gtttcgccac 1560
tggctatgcg ccgacccgcg tattggtccg ctgtttgaag agatgcacgc cgacctgttc 1620
cgcgctgatt actggcgcgc actacaaaac cgcatacgtg aagggcatgt ggaagatgtt 1680
tatgcgtatc ggcgcaggca aagatttagc gtacggtatg ggagatgct tttttga 1737

<210> SEQ ID NO 64
<211> LENGTH: 578
<212> TYPE: PRT
<213> ORGANISM: Escherichia coli

<400> SEQUENCE: 64

Met Pro Arg Gly Leu Glu Leu Leu Ile Ala Gln Thr Ile Leu Gln Gly
1               5                   10                  15

Phe Asp Ala Gln Tyr Gly Arg Phe Leu Glu Val Thr Ser Gly Ala Gln
            20                  25                  30

Gln Arg Phe Glu Gln Ala Asp Trp His Ala Val Gln Gln Ala Met Lys
        35                  40                  45

Asn Arg Ile His Leu Tyr Asp His His Val Gly Leu Val Val Glu Gln
    50                  55                  60

Leu Arg Cys Ile Thr Asn Gly Gln Ser Thr Asp Ala Ala Phe Leu Leu
65                  70                  75                  80

Arg Val Lys Glu His Tyr Thr Arg Leu Leu Pro Asp Tyr Pro Arg Phe
                85                  90                  95

Glu Ile Ala Glu Ser Phe Phe Asn Ser Val Tyr Cys Arg Leu Phe Asp
            100                 105                 110

His Arg Ser Leu Thr Pro Glu Arg Leu Phe Ile Phe Ser Ser Gln Pro
        115                 120                 125

Glu Arg Arg Phe Arg Thr Ile Pro Arg Pro Leu Ala Lys Asp Phe His
    130                 135                 140

Pro Asp His Gly Trp Glu Ser Leu Leu Met Arg Val Ile Ser Asp Leu
145                 150                 155                 160

Pro Leu Arg Leu Arg Trp Gln Asn Lys Ser Arg Asp Ile His Tyr Ile
                165                 170                 175

Ile Arg His Leu Thr Glu Thr Leu Gly Thr Asp Asn Leu Ala Glu Ser
            180                 185                 190

His Leu Gln Val Ala Asn Glu Leu Phe Tyr Arg Asn Lys Ala Ala Trp
        195                 200                 205

```
Leu Val Gly Lys Leu Ile Thr Pro Ser Gly Thr Leu Pro Phe Leu Leu
    210                 215                 220

Pro Ile His Gln Thr Asp Asp Gly Glu Leu Phe Ile Asp Thr Cys Leu
225                 230                 235                 240

Thr Thr Thr Ala Glu Ala Ser Ile Val Phe Gly Phe Ala Arg Ser Tyr
                245                 250                 255

Phe Met Val Tyr Ala Pro Leu Pro Ala Ala Leu Val Glu Trp Leu Arg
            260                 265                 270

Glu Ile Leu Pro Gly Lys Thr Thr Ala Glu Leu Tyr Met Ala Ile Gly
        275                 280                 285

Cys Gln Lys His Ala Lys Thr Glu Ser Tyr Arg Glu Tyr Leu Val Tyr
    290                 295                 300

Leu Gln Gly Cys Asn Glu Gln Phe Ile Glu Ala Pro Gly Ile Arg Gly
305                 310                 315                 320

Met Val Met Leu Val Phe Thr Leu Pro Gly Phe Asp Arg Val Phe Lys
                325                 330                 335

Val Ile Lys Asp Arg Phe Ala Pro Gln Lys Glu Met Ser Ala Ala His
            340                 345                 350

Val Arg Ala Cys Tyr Gln Leu Val Lys Glu His Asp Arg Val Gly Arg
        355                 360                 365

Met Ala Asp Thr Gln Glu Phe Glu Asn Phe Val Leu Glu Lys Arg His
    370                 375                 380

Ile Ser Pro Ala Leu Met Glu Leu Leu Leu Gln Glu Ala Ala Glu Lys
385                 390                 395                 400

Ile Thr Asp Leu Gly Glu Gln Ile Val Ile Arg His Leu Tyr Ile Glu
                405                 410                 415

Arg Arg Met Val Pro Leu Asn Ile Trp Leu Glu Gln Val Glu Gly Gln
            420                 425                 430

Gln Leu Arg Asp Ala Ile Glu Glu Tyr Gly Asn Ala Ile Arg Gln Leu
        435                 440                 445

Ala Ala Ala Asn Ile Phe Pro Gly Asp Met Leu Phe Lys Asn Phe Gly
    450                 455                 460

Val Thr Arg His Gly Arg Val Val Phe Tyr Asp Tyr Asp Glu Ile Cys
465                 470                 475                 480

Tyr Met Thr Glu Val Asn Phe Arg Asp Ile Pro Pro Pro Arg Tyr Pro
                485                 490                 495

Glu Asp Glu Leu Ala Ser Glu Pro Trp Tyr Ser Val Ser Pro Gly Asp
            500                 505                 510

Val Phe Pro Glu Glu Phe Arg His Trp Leu Cys Ala Asp Pro Arg Ile
        515                 520                 525

Gly Pro Leu Phe Glu Glu Met His Ala Asp Leu Phe Arg Ala Asp Tyr
    530                 535                 540

Trp Arg Ala Leu Gln Asn Arg Ile Arg Glu Gly His Val Glu Asp Val
545                 550                 555                 560

Tyr Ala Tyr Arg Arg Arg Gln Arg Phe Ser Val Arg Tyr Gly Glu Met
                565                 570                 575

Leu Phe
```

<210> SEQ ID NO 65
<211> LENGTH: 2145
<212> TYPE: DNA
<213> ORGANISM: Escherichia coli

<400> SEQUENCE: 65

-continued

```
gtgtcccgta ttattatgct gatccctacc ggaaccagcg tcggtctgac cagcgtcagc     60
cttggcgtga tccgtgcaat ggaacgcaaa ggcgttcgtc tgagcgtttt caaacctatc    120
gctcagccgc gtaccggtgg cgatgcgccc gatcagacta cgactatcgt gcgtgcgaac    180
tcttccacca cgacggccgc tgaaccgctg aaaatgagct acgttgaagg tctgctttcc    240
agcaatcaga aagatgtgct gatggaagag atcgtcgcaa actaccacgc taacaccaaa    300
gacgctgaag tcgttctggt tgaaggtctg gtcccgacac gtaagcacca gtttgcccag    360
tctctgaact acgaaatcgc taaaacgctg aatgcggaaa tcgtcttcgt tatgtctcag    420
ggcactgaca ccccggaaca gctgaaagag cgtatcgaac tgacccgcaa cagcttcggc    480
ggtgccaaaa acaccaacat caccggcgtt atcgttaaca aactgaacgc accggttgat    540
gaacagggtc gtactcgccc ggatctgtcc gagattttcg acgactcttc caaagctaaa    600
gtaaacaatg ttgatccggc gaagctgcaa gaatccagcc cgctgccggt tctcggcgct    660
gtgccgtgga gctttgacct gatcgcgact cgtgcgatcg atatggctcg ccacctgaat    720
gcgaccatca tcaacgaagg cgacatcaat actcgccgcg ttaaatccgt cactttctgc    780
gcacgcagca ttccgcacat gctggagcac ttccgtgccg gttctctgct ggtgacttcc    840
gcagaccgtc ctgacgtgct ggtggccgct tgcctggcag ccatgaacgg cgtagaaatc    900
ggtgccctgc tgctgactgg cggttacgaa atggacgcgc gcatttctaa actgtgcgaa    960
cgtgctttcg ctaccggcct gccggtattt atggtgaaca ccaacacctg gcagacctct   1020
ctgagcctgc agagcttcaa cctggaagtt ccggttgacg atcacgaacg tatcgagaaa   1080
gttcaggaat acgttgctaa ctacatcaac gctgactgga tcgaatctct gactgccact   1140
tctgagcgca gccgtcgtct gtctccgcct gcgttccgtt atcagctgac tgaacttgcg   1200
cgcaaagcgg gcaaacgtat cgtactgccg gaaggtgacg aaccgcgtac cgttaaagca   1260
gccgctatct gtgctgaacg tggtatcgca acttgcgtac tgctgggtaa tccggcagag   1320
atcaaccgtg ttgcagcgtc tcagggtgta gaactgggtg cagggattga aatcgttgat   1380
ccagaagtgg ttcgcgaaag ctatgttggt cgtctggtcg aactgcgtaa gaacaaaggc   1440
atgaccgaaa ccgttgcccg cgaacagctg gaagacaacg tggtgctcgg tacgctgatg   1500
ctggaacagg atgaagttga tggtctggtt tccggtgctg ttcacactac cgcaaacacc   1560
atccgtccgc cgctgcagct gatcaaaact gcaccgggca gctccctggt atcttccgtg   1620
ttcttcatgc tgctgccgga acaggtttac gtttacggtg actgtgcgat caacccggat   1680
ccgaccgctg aacagctggc agaaatcgcg attcagtccg ctgattccgc tgcggccttc   1740
ggtatcgaac cgcgcgttgc tatgctctcc tactccaccg gtacttctgg tgcaggtagc   1800
gacgtagaaa aagttcgcga agcaactcgt ctggcgcagg aaaaacgtcc tgacctgatg   1860
atcgacggtc cgctgcagta cgacgctgcg gtaatggctg acgttgcgaa atccaaagcg   1920
ccgaactctc cggttgcagg tcgcgctacc gtgttcatct tcccggatct gaacaccggt   1980
aacaccacct acaaagcggt acagcgttct gccgacctga tctccatcgg gccgatgctg   2040
cagggtatgc gcaagccggt taacgacctg tcccgtggcg cactggttga cgatatcgtc   2100
tacaccatcg cgctgactgc gattcagtct gcacagcagc agtaa                   2145
```

<210> SEQ ID NO 66
<211> LENGTH: 714
<212> TYPE: PRT
<213> ORGANISM: Escherichia coli

<400> SEQUENCE: 66

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
    290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
    370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415
```

```
Thr Val Lys Ala Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
    450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
    530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
    610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
    690                 695                 700

Leu Thr Ala Ile Gln Ser Ala Gln Gln Gln
705                 710
```

<210> SEQ ID NO 67
<211> LENGTH: 1203
<212> TYPE: DNA
<213> ORGANISM: Escherichia coli

<400> SEQUENCE: 67

```
atgtcgagta agttagtact ggttctgaac tgcggtagtt cttcactgaa atttgccatc      60

atcgatgcag taaatggtga agagtacctt tctggtttag ccgaatgttt ccacctgccc     120

gaagcacgta tcaaatggaa aatggacggc aataaacagg aagcggcttt aggtgcaggc     180

gccgctcaca gcgaagcgct caactttatc gttaatacta ttctggcaca aaaaccagaa     240

ctgtctgcgc agctgactgc tatcggtcac cgtatcgtac acggcggcga aaagtatacc     300

agctccgtag tgatcgatga gtctgttatt cagggtatca aagatgcagc ttcttttgca     360

ccgctgcaca acccggctca cctgatcggt atcgaagaag ctctgaaatc tttcccacag     420
```

```
ctgaaagaca aaaacgttgc tgtatttgac accgcgttcc accagactat gccggaagag    480

tcttacctct acgccctgcc ttacaacctg tacaaagagc acggcatccg tcgttacggc    540

gcgcacggca ccagccactt ctatgtaacc caggaagcgg caaaaatgct gaacaaaccg    600

gtagaagaac tgaacatcat cacctgccac ctgggcaacg gtggttccgt ttctgctatc    660

cgcaacggta aatgcgttga cacctctatg ggcctgaccc cgctggaagg tctggtcatg    720

ggtacccgtt ctggtgatat cgatccggcg atcatcttcc acctgcacga caccctgggc    780

atgagcgttg acgcaatcaa caaactgctg accaaagagt ctggcctgct gggtctgacc    840

gaagtgacca gcgactgccg ctatgttgaa gacaactacg cgacgaaaga agacgcgaag    900

cgcgcaatgg acgtttactg ccaccgcctg gcgaaataca tcggtgccta cactgcgctg    960

atggatggtc gtctggacgc tgttgtattc actggtggta tcggtgaaaa tgccgcaatg   1020

gttcgtgaac tgtctctggg caaactgggc gtgctgggct ttgaagttga tcatgaacgc   1080

aacctggctg cacgtttcgg caaatctggt ttcatcaaca aagaaggtac ccgtcctgcg   1140

gtggttatcc caaccaacga agaactggtt atcgcgcaag acgcgagccg cctgactgcc   1200

tga                                                                 1203
```

<210> SEQ ID NO 68
<211> LENGTH: 400
<212> TYPE: PRT
<213> ORGANISM: Escherichia coli

<400> SEQUENCE: 68

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
```

-continued

```
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
            340                 345                 350

Gly Phe Glu Val Asp His Glu Arg Asn Leu Ala Ala Arg Phe Gly Lys
        355                 360                 365

Ser Gly Phe Ile Asn Lys Glu Gly Thr Arg Pro Ala Val Val Ile Pro
    370                 375                 380

Thr Asn Glu Glu Leu Val Ile Ala Gln Asp Ala Ser Arg Leu Thr Ala
385                 390                 395                 400
```

<210> SEQ ID NO 69
<211> LENGTH: 1719
<212> TYPE: DNA
<213> ORGANISM: Escherichia coli

<400> SEQUENCE: 69

```
atgaaacaaa cggttgcagc ttatatcgcc aaaacactcg aatcggcagg ggtgaaacgc      60

atctggggag tcacaggcga ctctctgaac ggtcttagtg acagtcttaa tcgcatgggc     120

accatcgagt ggatgtccac ccgccacgaa gaagtggcgg cctttgccgc tggcgctgaa     180

gcacaactta gcggagaact ggcggtctgc gccggatcgt gcggccccgg caacctgcac     240

ttaatcaacg gcctgttcga ttgccaccgc aatcacgttc cggtactggc gattgccgct     300

catattccct ccagcgaaat tggcagcggc tatttccagg aaacccaccc acaagagcta     360

ttccgcgaat gtagtcacta ttgcgagctg gtttccagcc cggagcagat cccacaagta     420

ctggcgattg ccatgcgcaa agcggtgctt aaccgtggcg tttcggttgt cgtgttacca     480

ggcgacgtgg cgttaaaacc tgcgccagaa ggggcaacca tgcactggta tcatgcgcca     540

caaccagtcg tgacgccgga agaagaagag ttacgcaaac tggcgcaact gctgcgttat     600

tccagcaata tcgccctgat gtgtggcagc ggctgcgcgg gggcgcataa agagttagtt     660

gagtttgccg ggaaaattaa agcgcctatt gttcatgccc tgcgcggtaa agaacatgtc     720

gaatacgata atccgtatga tgttggaatg accgggttaa tcggcttctc gtcaggtttc     780

cataccatga tgaacgccga cacgttagtg ctactcggca cgcaatttcc ctaccgcgcc     840

ttctacccga ccgatgccaa aatcattcag attgatatca acccagccag catcggcgct     900

cacagcaagg tggatatggc actggtcggc gatatcaagt cgactctgcg tgcattgctt     960

ccattggtgg aagaaaaagc cgatcgcaag tttctggata aagcgctgga agattaccgc    1020

gacgcccgca aagggctgga cgatttagct aaaccgagcg agaaagccat tcacccgcaa    1080

tatctggcgc agcaaattag tcattttgcc gccgatgacg ctattttcac ctgtgacgtt    1140

ggtacgccaa cggtgtgggc ggcacgttat ctaaaaatga acggcaagcg tcgcctgtta    1200
```

-continued

```
ggttcgttta accacggttc gatggctaac gccatgccgc aggcgctggg tgcgcaggcg   1260

acagagccag aacgtcaggt ggtcgccatg tgcggcgatg gcggttttag catgttgatg   1320

ggcgatttcc tctcagtagt gcagatgaaa ctgccagtga aaattgtcgt ctttaacaac   1380

agcgtgctgg gctttgtggc gatggagatg aaagctggtg gctatttgac tgacggcacc   1440

gaactacacg acacaaactt tgcccgcatt gccgaagcgt gcggcattac gggtatccgt   1500

gtagaaaaag cgtctgaagt tgatgaagcc ctgcaacgcg ccttctccat cgacggtccg   1560

gtgttggtgg atgtggtggt cgccaaagaa gagttagcca ttccaccgca gatcaaactc   1620

gaacaggcca aaggtttcag cctgtatatg ctgcgcgcaa tcatcagcgg acgcggtgat   1680

gaagtgatcg aactggcgaa aacaaactgg ctaaggtaa                          1719
```

<210> SEQ ID NO 70
<211> LENGTH: 572
<212> TYPE: PRT
<213> ORGANISM: Escherichia coli

<400> SEQUENCE: 70

```
Met Lys Gln Thr Val Ala Ala Tyr Ile Ala Lys Thr Leu Glu Ser Ala
1               5                   10                  15

Gly Val Lys Arg Ile Trp Gly Val Thr Gly Asp Ser Leu Asn Gly Leu
            20                  25                  30

Ser Asp Ser Leu Asn Arg Met Gly Thr Ile Glu Trp Met Ser Thr Arg
        35                  40                  45

His Glu Glu Val Ala Ala Phe Ala Ala Gly Ala Glu Ala Gln Leu Ser
    50                  55                  60

Gly Glu Leu Ala Val Cys Ala Gly Ser Cys Gly Pro Gly Asn Leu His
65                  70                  75                  80

Leu Ile Asn Gly Leu Phe Asp Cys His Arg Asn His Val Pro Val Leu
                85                  90                  95

Ala Ile Ala Ala His Ile Pro Ser Ser Glu Ile Gly Ser Gly Tyr Phe
            100                 105                 110

Gln Glu Thr His Pro Gln Glu Leu Phe Arg Glu Cys Ser His Tyr Cys
        115                 120                 125

Glu Leu Val Ser Ser Pro Glu Gln Ile Pro Gln Val Leu Ala Ile Ala
    130                 135                 140

Met Arg Lys Ala Val Leu Asn Arg Gly Val Ser Val Val Val Leu Pro
145                 150                 155                 160

Gly Asp Val Ala Leu Lys Pro Ala Pro Glu Gly Ala Thr Met His Trp
                165                 170                 175

Tyr His Ala Pro Gln Pro Val Val Thr Pro Glu Glu Glu Glu Leu Arg
            180                 185                 190

Lys Leu Ala Gln Leu Leu Arg Tyr Ser Ser Asn Ile Ala Leu Met Cys
        195                 200                 205

Gly Ser Gly Cys Ala Gly Ala His Lys Glu Leu Val Glu Phe Ala Gly
    210                 215                 220

Lys Ile Lys Ala Pro Ile Val His Ala Leu Arg Gly Lys Glu His Val
225                 230                 235                 240

Glu Tyr Asp Asn Pro Tyr Asp Val Gly Met Thr Gly Leu Ile Gly Phe
                245                 250                 255

Ser Ser Gly Phe His Thr Met Met Asn Ala Asp Thr Leu Val Leu Leu
            260                 265                 270

Gly Thr Gln Phe Pro Tyr Arg Ala Phe Tyr Pro Thr Asp Ala Lys Ile
```

```
        275                 280                 285

Ile Gln Ile Asp Ile Asn Pro Ala Ser Ile Gly Ala His Ser Lys Val
    290                 295                 300

Asp Met Ala Leu Val Gly Asp Ile Lys Ser Thr Leu Arg Ala Leu Leu
305                 310                 315                 320

Pro Leu Val Glu Glu Lys Ala Asp Arg Lys Phe Leu Asp Lys Ala Leu
                325                 330                 335

Glu Asp Tyr Arg Asp Ala Arg Lys Gly Leu Asp Asp Leu Ala Lys Pro
            340                 345                 350

Ser Glu Lys Ala Ile His Pro Gln Tyr Leu Ala Gln Gln Ile Ser His
        355                 360                 365

Phe Ala Ala Asp Asp Ala Ile Phe Thr Cys Asp Val Gly Thr Pro Thr
    370                 375                 380

Val Trp Ala Ala Arg Tyr Leu Lys Met Asn Gly Lys Arg Arg Leu Leu
385                 390                 395                 400

Gly Ser Phe Asn His Gly Ser Met Ala Asn Ala Met Pro Gln Ala Leu
                405                 410                 415

Gly Ala Gln Ala Thr Glu Pro Glu Arg Gln Val Val Ala Met Cys Gly
            420                 425                 430

Asp Gly Gly Phe Ser Met Leu Met Gly Asp Phe Leu Ser Val Val Gln
        435                 440                 445

Met Lys Leu Pro Val Lys Ile Val Val Phe Asn Asn Ser Val Leu Gly
    450                 455                 460

Phe Val Ala Met Glu Met Lys Ala Gly Gly Tyr Leu Thr Asp Gly Thr
465                 470                 475                 480

Glu Leu His Asp Thr Asn Phe Ala Arg Ile Ala Glu Ala Cys Gly Ile
                485                 490                 495

Thr Gly Ile Arg Val Glu Lys Ala Ser Glu Val Asp Glu Ala Leu Gln
            500                 505                 510

Arg Ala Phe Ser Ile Asp Gly Pro Val Leu Val Asp Val Val Val Ala
        515                 520                 525

Lys Glu Glu Leu Ala Ile Pro Pro Gln Ile Lys Leu Glu Gln Ala Lys
    530                 535                 540

Gly Phe Ser Leu Tyr Met Leu Arg Ala Ile Ile Ser Gly Arg Gly Asp
545                 550                 555                 560

Glu Val Ile Glu Leu Ala Lys Thr Asn Trp Leu Arg
                565                 570


<210> SEQ ID NO 71
<211> LENGTH: 825
<212> TYPE: DNA
<213> ORGANISM: Escherichia coli

<400> SEQUENCE: 71

atggtcgcac ccattcccgc gaaacgcggc agaaaacccg ccgttgccac cgcaccagcg      60

actggacagg ttcagtcttt aacgcgtggc ctgaaattac tggagtggat tgccgaatcc     120

aatggcagtg tggcactcac ggaactggcg caacaagccg ggttacccaa ttccacgacc     180

caccgcctgc taaccacgat gcaacagcag ggtttcgtgc gtcaggttgg cgaactggga     240

cattgggcaa tcggcgcaca tgcctttatg gtcggcagca gctttctcca gagccgtaat     300

ttgttagcga ttgttcaccc tatcctgcgc aatctaatgg aagagtctgg cgaaacggtc     360

aatatggcgg tgcttgatca aagcgatcac gaagcgatta ttatcgacca ggtacagtgt     420

acgcatctga tgcgaatgtc cgcgcctatc ggcggtaaat tgccgatgca cgcttccggt     480
```

```
gcgggtaaag cctttttagc ccaactgagc gaagaacagg tgacgaagct gctgcaccgc    540

aaagggttac atgcctatac ccacgcaacg ctggtgtctc ctgtgcattt aaaagaagat    600

ctcgcccaaa cgcgcaaacg gggttattca tttgacgatg aggaacatgc actggggcta    660

cgttgccttg cagcgtgtat tttcgatgag caccgtgaac cgtttgccgc aatttctatt    720

tccggaccga tttcacgtat taccgatgac cgcgtgaccg agtttggcgc gatggtgatt    780

aaagcggcga aggaagtgac gctggcgtac ggtggaatgc gctga                   825
```

\<210\> SEQ ID NO 72
\<211\> LENGTH: 274
\<212\> TYPE: PRT
\<213\> ORGANISM: Escherichia coli

\<400\> SEQUENCE: 72

```
Met Val Ala Pro Ile Pro Ala Lys Arg Gly Arg Lys Pro Ala Val Ala
1               5                   10                  15

Thr Ala Pro Ala Thr Gly Gln Val Gln Ser Leu Thr Arg Gly Leu Lys
            20                  25                  30

Leu Leu Glu Trp Ile Ala Glu Ser Asn Gly Ser Val Ala Leu Thr Glu
        35                  40                  45

Leu Ala Gln Gln Ala Gly Leu Pro Asn Ser Thr Thr His Arg Leu Leu
    50                  55                  60

Thr Thr Met Gln Gln Gln Gly Phe Val Arg Gln Val Gly Glu Leu Gly
65                  70                  75                  80

His Trp Ala Ile Gly Ala His Ala Phe Met Val Gly Ser Ser Phe Leu
                85                  90                  95

Gln Ser Arg Asn Leu Leu Ala Ile Val His Pro Ile Leu Arg Asn Leu
            100                 105                 110

Met Glu Glu Ser Gly Glu Thr Val Asn Met Ala Val Leu Asp Gln Ser
        115                 120                 125

Asp His Glu Ala Ile Ile Ile Asp Gln Val Gln Cys Thr His Leu Met
    130                 135                 140

Arg Met Ser Ala Pro Ile Gly Gly Lys Leu Pro Met His Ala Ser Gly
145                 150                 155                 160

Ala Gly Lys Ala Phe Leu Ala Gln Leu Ser Glu Glu Gln Val Thr Lys
                165                 170                 175

Leu Leu His Arg Lys Gly Leu His Ala Tyr Thr His Ala Thr Leu Val
            180                 185                 190

Ser Pro Val His Leu Lys Glu Asp Leu Ala Gln Thr Arg Lys Arg Gly
        195                 200                 205

Tyr Ser Phe Asp Asp Glu Glu His Ala Leu Gly Leu Arg Cys Leu Ala
    210                 215                 220

Ala Cys Ile Phe Asp Glu His Arg Glu Pro Phe Ala Ala Ile Ser Ile
225                 230                 235                 240

Ser Gly Pro Ile Ser Arg Ile Thr Asp Asp Arg Val Thr Glu Phe Gly
                245                 250                 255

Ala Met Val Ile Lys Ala Ala Lys Glu Val Thr Leu Ala Tyr Gly Gly
            260                 265                 270

Met Arg
```

\<210\> SEQ ID NO 73
\<211\> LENGTH: 720
\<212\> TYPE: DNA
\<213\> ORGANISM: Escherichia coli

<400> SEQUENCE: 73

```
atggtcatta aggcgcaaag cccggcgggt ttcgcggaag agtacattat tgaaagtatc      60
tggaataacc gcttccctcc cgggactatt ttgcccgcag aacgtgaact ttcagaatta     120
attggcgtaa cgcgtactac gttacgtgaa gtgttacagc gtctggcacg agatggctgg     180
ttgaccattc aacatggcaa gccgacgaag gtgaataatt tctgggaaac ttccggttta     240
aatatccttg aaacactggc gcgactggat cacgaaagtg tgccgcagct tattgataat     300
ttgctgtcgg tgcgtaccaa tatttccact atttttattc gcaccgcgtt tcgtcagcat     360
cccgataaag cgcaggaagt gctggctacc gctaatgaag tggccgatca cgccgatgcc     420
tttgccgagc tggattacaa catattccgc ggcctggcgt ttgcttccgg caacccgatt     480
tacggtctga ttcttaacgg gatgaaaggg ctgtatacgc gtattggtcg tcactatttc     540
gccaatccgg aagcgcgcag tctggcgctg ggcttctacc acaaactgtc ggcgttgtgc     600
agtgaaggcg cgcacgatca ggtgtacgaa acagtgcgtc gctatgggca tgagagtggc     660
gagatttggc accggatgca gaaaaatctg ccgggtgatt tagccattca ggggcgataa     720
```

<210> SEQ ID NO 74
<211> LENGTH: 239
<212> TYPE: PRT
<213> ORGANISM: Escherichia coli

<400> SEQUENCE: 74

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235
```

<210> SEQ ID NO 75
<211> LENGTH: 1650
<212> TYPE: DNA
<213> ORGANISM: Escherichia coli

<400> SEQUENCE: 75
atgaaaaaca tcaatccaac gcagaccgct gcctggcagg cactacagaa acacttcgat 60
gaaatgaaag acgttacgat cgccgatctt tttgctaaag acggcgatcg tttttctaag 120
ttctccgcaa ccttcgacga tcagatgctg gtggattact ccaaaaaccg catcactgaa 180
gagacgctgg cgaaattaca ggatctggcg aaagagtgcg atctggcggg cgcgattaag 240
tcgatgttct ctggcgagaa gatcaaccgc actgaaaacc gcgccgtgct gcacgtagcg 300
ctgcgtaacc gtagcaatac cccgattttg gttgatggca aagacgtaat gccggaagtc 360
aacgcggtgc tggagaagat gaaaaccttc tcagaagcga ttatttccgg tgagtggaaa 420
ggttataccg gcaaagcaat cactgacgta gtgaacatcg ggatcggcgg ttctgacctc 480
ggcccataca tggtgaccga agctctgcgt ccgtacaaaa accacctgaa catgcacttt 540
gtttctaacg tcgatgggac tcacatcgcg gaagtgctga aaaaagtaaa cccggaaacc 600
acgctgttct tggtagcatc taaaaccttc accactcagg aaactatgac caacgcccat 660
agcgcgcgtg actggttcct gaaagcggca ggtgatgaaa aacacgttgc aaaacacttt 720
gcggcgcttt ccaccaatgc caaagccgtt ggcgagtttg gtattgatac tgccaacatg 780
ttcgagttct gggactgggt tggcggccgt tactctttgt ggtcagcgat tggcctgtcg 840
attgttctct ccatcggctt tgataacttc gttgaactgc tttccggcgc acacgcgatg 900
gacaagcatt tctccaccac gcctgccgag aaaaacctgc ctgtactgct ggcgctgatt 960
ggcatctggt acaacaattt ctttggtgcg gaaactgaag cgattctgcc gtatgaccag 1020
tatatgcacc gtttcgcggc gtacttccag cagggcaata tggagtccaa cggtaagtat 1080
gttgaccgta acggtaacgt tgtggattac cagactggcc cgattatctg gggtgaacca 1140
ggcactaacg gtcagcacgc gttctaccag ctgatccacc agggaaccaa aatggtaccg 1200
tgcgatttca tcgctccggc tatcacccat aacccgctct ctgatcatca ccagaaactg 1260
ctgtctaact tcttcgccca gaccgaagcg ctggcgtttg gtaaatcccg cgaagtggtt 1320
gagcaggaat atcgtgatca gggtaaagat ccggcaacgc ttgactacgt ggtgccgttc 1380
aaagtattcg aaggtaaccg cccgaccaac tccatcctgc tgcgtgaaat cactccgttc 1440
agcctgggtg cgttgattgc gctgtatgag cacaaaatct ttactcaggg cgtgatcctg 1500
aacatcttca ccttcgacca gtggggcgtg gaactgggta aacagctggc gaaccgtatt 1560
ctgccagagc tgaaagatga taaagaaatc agcagccacg atagctcgac caatggtctg 1620
attaaccgct ataaagcgtg gcgcggttaa 1650

<210> SEQ ID NO 76
<211> LENGTH: 549
<212> TYPE: PRT
<213> ORGANISM: Escherichia coli

<400> SEQUENCE: 76

Met Lys Asn Ile Asn Pro Thr Gln Thr Ala Ala Trp Gln Ala Leu Gln
1 5 10 15

Lys His Phe Asp Glu Met Lys Asp Val Thr Ile Ala Asp Leu Phe Ala
20 25 30

-continued

```
Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
        435                 440                 445

Lys Asp Pro Ala Thr Leu Asp Tyr Val Val Pro Phe Lys Val Phe Glu
```

```
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
        515                 520                 525

Glu Ile Ser Ser His Asp Ser Ser Thr Asn Gly Leu Ile Asn Arg Tyr
    530                 535                 540

Lys Ala Trp Arg Gly
545


<210> SEQ ID NO 77
<211> LENGTH: 1401
<212> TYPE: DNA
<213> ORGANISM: Escherichia coli

<400> SEQUENCE: 77

atgccacatt cctacgatta cgatgccata gtaataggtt ccggccccgg cggcgaaggc      60

gctgcaatgg gcctggttaa gcaaggtgcg cgcgtcgcag ttatcgagcg ttatcaaaat     120

gttggcggcg gttgcaccca ctggggcacc atcccgtcga aagctctccg tcacgccgtc     180

agccgcatta tagaattcaa tcaaaaccca ctttacagcg accattcccg actgctccgc     240

tcttcttttg ccgatatcct taaccatgcc gataacgtga ttaatcaaca aacgcgcatg     300

cgtcagggat tttacgaacg taatcactgt gaaatattgc agggaaacgc tcgctttgtt     360

gacgagcata cgttggcgct ggattgcccg gacggcagcg ttgaaacact aaccgctgaa     420

aaatttgtta ttgcctgcgg ctctcgtcca tatcatccaa cagatgttga tttcacccat     480

ccacgcattt acgacagcga ctcaattctc agcatgcacc acgaaccgcg ccatgtactt     540

atctatggtg ctggagtgat cggctgtgaa tatgcgtcga tcttccgcgg tatggatgta     600

aaagtggatc tgatcaacac ccgcgatcgc ctgctggcat ttctcgatca agagatgtca     660

gattctctct cctatcactt ctggaacagt ggcgtagtga ttcgtcacaa cgaagagtac     720

gagaagatcg aaggctgtga cgatggtgtg atcatgcatc tgaagtcggg taaaaaactg     780

aaagctgact gcctgctcta tgccaacggt cgcaccggta ataccgattc gctggcgtta     840

cagaacattg ggctagaaac tgacagccgc ggacagctga aggtcaacag catgtatcag     900

accgcacagc cacacgttta cgcggtgggc gacgtgattg gttatccgag cctggcgtcg     960

gcggcctatg accaggggcg cattgccgcg caggcgctgg taaaaggcga agccaccgca    1020

catctgattg aagatatccc taccggtatt tacaccatcc cggaaatcag ctctgtgggc    1080

aaaaccgaac agcagctgac cgcaatgaaa gtgccatatg aagtgggccg cgcccagttt    1140

aaacatctgg cacgcgcaca aatcgtcggc atgaacgtgg gcacgctgaa aattttgttc    1200

catcgggaaa caaaagagat tctgggtatt cactgctttg gcgagcgcgc tgccgaaatt    1260

attcatatcg gtcaggcgat tatggaacag aaaggtggcg gcaacactat tgagtacttc    1320

gtcaacacca cctttaacta cccgacgatg gcggaagcct atcgggtagc tgcgttaaac    1380

ggtttaaacc gcctgtttta a                                               1401


<210> SEQ ID NO 78
<211> LENGTH: 466
```

<212> TYPE: PRT
<213> ORGANISM: Escherichia coli

<400> SEQUENCE: 78

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400
```

His Arg Glu Thr Lys Glu Ile Leu Gly Ile His Cys Phe Gly Glu Arg
405 410 415

Ala Ala Glu Ile Ile His Ile Gly Gln Ala Ile Met Glu Gln Lys Gly
420 425 430

Gly Gly Asn Thr Ile Glu Tyr Phe Val Asn Thr Thr Phe Asn Tyr Pro
435 440 445

Thr Met Ala Glu Ala Tyr Arg Val Ala Ala Leu Asn Gly Leu Asn Arg
450 455 460

Leu Phe
465

<210> SEQ ID NO 79
<211> LENGTH: 1683
<212> TYPE: DNA
<213> ORGANISM: Escherichia coli

<400> SEQUENCE: 79
atggttacct ggacccaaat gtatatgccg atgggaggac tggggctatc cgctctggtc 60
gccctgatcc cgataatatt cttcttcgtt gcactcgcgg tattacgtct gaaaggacat 120
gtcgctggag caataaccct tatattatct atcctgattg caatattcgc ctttaaaatg 180
ccgattgata tggcatttgc tgctgcgggc tatggcttta tttatggatt atggccaata 240
gcgtggatta ttgtcgcggc ggtgttcctg tataaattaa ccgttgccag cgggcagttc 300
gatattatcc gcagctcggt tatctccatc accgacgatc agcgtttgca ggtgttactg 360
attggtttct cctttggtgc gttgctggaa ggagcggctg gctttggtgc gccggtggcg 420
attaccggtg cgctgctggt gggcctgggc ttcaaaccgt tatacgcggc ggggctgtgt 480
ctgattgcca atactgcgcc ggtggcgttt ggtgcgttgg gcgtgccgat tctggtcgcc 540
ggtcaggtaa cgggaatcga tccgttccac attggcgcaa tggcgggacg tcagttaccg 600
ttcctgtcgg ttcttgtgcc gttctggctg gtagcaatga tggacggctg gaaaggggtg 660
aaagagacgt ggccagcggc gctggttgct gggggaagct tcgctgtcac tcagttcttt 720
acctctaact atattggtcc ggaactgccg gatattactt cggcgctggt gagtatcgtc 780
tcactcgctt tattccttaa agtctggcgg ccgaaaaata ccgaaacggc aatcagcatg 840
ggacaatccg caggtgcgat ggtggtaaat aagccatctt ctggcggtcc cgtgccttca 900
gaatatagtc tggggcaaat cattcgagcg tggtcaccgt ttttaatctt aacggtgctg 960
gtcaccatct ggaccatgaa gccgtttaaa gcgttatttg ctccgggcgg cgcgttttat 1020
tcactggtga ttaatttcca gatccctcat ttgcatcaac aagtgttgaa agcggcaccc 1080
attgtcgccc aaccaacgcc aatggatgcg gtgtttaaat tcgacccct ctcggctggc 1140 ggcaccgcta tttttattgc ggcgattatc tctatcttca tcctcggtgt ggggatcaag 1200
aaaggtattg gcgtctttgc cgaaacgcta attagcttga agtggccgat actgtcgatt 1260
ggcatggtgc tggcgttcgc cttcgtcacc aactattctg gcatgtccac cacgctggcg 1320
ctggtactgg caggtacagg cgtgatgttc ccgttcttct caccgtttct cggctggctg 1380
ggcgtattcc ttaccggctc ggacacctcc tctaacgccc tgtttggttc actgcaatcg 1440
accacggcgc agcaaatcaa cgtctctgac accctgctgg tggcagcaaa caccagcggc 1500
ggcgtaactg gcaagatgat ctccccgcaa tctatcgccg tggcctgcgc cgcgacgggc 1560
atggtgggcc gagaatctga actgttccgc tacaccgtga agcacagtct gatttttgcc 1620
agcgttatcg gcattatcac cctgctgcag gcgtatgtgt ttaccgggat gttagtctcg 1680
taa 1683

<210> SEQ ID NO 80
<211> LENGTH: 560
<212> TYPE: PRT
<213> ORGANISM: Escherichia coli

<400> SEQUENCE: 80

```
Met Val Thr Trp Thr Gln Met Tyr Met Pro Met Gly Gly Leu Gly Leu
1               5                   10                  15

Ser Ala Leu Val Ala Leu Ile Pro Ile Ile Phe Phe Phe Val Ala Leu
            20                  25                  30

Ala Val Leu Arg Leu Lys Gly His Val Ala Gly Ala Ile Thr Leu Ile
        35                  40                  45

Leu Ser Ile Leu Ile Ala Ile Phe Ala Phe Lys Met Pro Ile Asp Met
    50                  55                  60

Ala Phe Ala Ala Ala Gly Tyr Gly Phe Ile Tyr Gly Leu Trp Pro Ile
65                  70                  75                  80

Ala Trp Ile Ile Val Ala Ala Val Phe Leu Tyr Lys Leu Thr Val Ala
                85                  90                  95

Ser Gly Gln Phe Asp Ile Ile Arg Ser Ser Val Ile Ser Ile Thr Asp
            100                 105                 110

Asp Gln Arg Leu Gln Val Leu Leu Ile Gly Phe Ser Phe Gly Ala Leu
        115                 120                 125

Leu Glu Gly Ala Ala Gly Phe Gly Ala Pro Val Ala Ile Thr Gly Ala
    130                 135                 140

Leu Leu Val Gly Leu Gly Phe Lys Pro Leu Tyr Ala Ala Gly Leu Cys
145                 150                 155                 160

Leu Ile Ala Asn Thr Ala Pro Val Ala Phe Gly Ala Leu Gly Val Pro
                165                 170                 175

Ile Leu Val Ala Gly Gln Val Thr Gly Ile Asp Pro Phe His Ile Gly
            180                 185                 190

Ala Met Ala Gly Arg Gln Leu Pro Phe Leu Ser Val Leu Val Pro Phe
        195                 200                 205

Trp Leu Val Ala Met Met Asp Gly Trp Lys Gly Val Lys Glu Thr Trp
    210                 215                 220

Pro Ala Ala Leu Val Ala Gly Gly Ser Phe Ala Val Thr Gln Phe Phe
225                 230                 235                 240

Thr Ser Asn Tyr Ile Gly Pro Glu Leu Pro Asp Ile Thr Ser Ala Leu
                245                 250                 255

Val Ser Ile Val Ser Leu Ala Leu Phe Leu Lys Val Trp Arg Pro Lys
            260                 265                 270

Asn Thr Glu Thr Ala Ile Ser Met Gly Gln Ser Ala Gly Ala Met Val
        275                 280                 285

Val Asn Lys Pro Ser Ser Gly Gly Pro Val Pro Ser Glu Tyr Ser Leu
    290                 295                 300

Gly Gln Ile Ile Arg Ala Trp Ser Pro Phe Leu Ile Leu Thr Val Leu
305                 310                 315                 320

Val Thr Ile Trp Thr Met Lys Pro Phe Lys Ala Leu Phe Ala Pro Gly
                325                 330                 335

Gly Ala Phe Tyr Ser Leu Val Ile Asn Phe Gln Ile Pro His Leu His
            340                 345                 350

Gln Gln Val Leu Lys Ala Ala Pro Ile Val Ala Gln Pro Thr Pro Met
        355                 360                 365
```

-continued

```
Asp Ala Val Phe Lys Phe Asp Pro Leu Ser Ala Gly Gly Thr Ala Ile
    370                 375                 380

Phe Ile Ala Ala Ile Ile Ser Ile Phe Ile Leu Gly Val Gly Ile Lys
385                 390                 395                 400

Lys Gly Ile Gly Val Phe Ala Glu Thr Leu Ile Ser Leu Lys Trp Pro
                405                 410                 415

Ile Leu Ser Ile Gly Met Val Leu Ala Phe Ala Phe Val Thr Asn Tyr
            420                 425                 430

Ser Gly Met Ser Thr Thr Leu Ala Leu Val Leu Ala Gly Thr Gly Val
        435                 440                 445

Met Phe Pro Phe Phe Ser Pro Phe Leu Gly Trp Leu Gly Val Phe Leu
    450                 455                 460

Thr Gly Ser Asp Thr Ser Ser Asn Ala Leu Phe Gly Ser Leu Gln Ser
465                 470                 475                 480

Thr Thr Ala Gln Gln Ile Asn Val Ser Asp Thr Leu Leu Val Ala Ala
                485                 490                 495

Asn Thr Ser Gly Gly Val Thr Gly Lys Met Ile Ser Pro Gln Ser Ile
            500                 505                 510

Ala Val Ala Cys Ala Ala Thr Gly Met Val Gly Arg Glu Ser Glu Leu
        515                 520                 525

Phe Arg Tyr Thr Val Lys His Ser Leu Ile Phe Ala Ser Val Ile Gly
    530                 535                 540

Ile Ile Thr Leu Leu Gln Ala Tyr Val Phe Thr Gly Met Leu Val Ser
545                 550                 555                 560
```

<210> SEQ ID NO 81
<211> LENGTH: 1656
<212> TYPE: DNA
<213> ORGANISM: Escherichia coli

<400> SEQUENCE: 81

```
atgaatctct ggcaacaaaa ctacgatccc gccgggaata tctggctttc cagtctgata     60

gcatcgcttc ccatcctgtt tttcttcttt gcgctgatta agctcaaact gaaaggatac    120

gtcgccgcct cgtggacggt ggcaatcgcc cttgccgtgg ctttgctgtt ctataaaatg    180

ccggtcgcta acgcgctggc ctcggtggtt tatggtttct tctacgggtt gtggcccatc    240

gcgtggatca ttattgcagc ggtgttcgtc tataagatct cggtgaaaac cgggcagttt    300

gacatcattc gctcgtctat tctttcgata acccctgacc agcgtctgca aatgctgatc    360

gtcggtttct gtttcggcgc gttccttgaa ggagccgcag gctttggcgc accggtagca    420

attaccgccg cattgctggt cggcctgggt tttaaaccgc tgtacgccgc cgggctgtgc    480

ctgattgtta acaccgcgcc agtggcattt ggtgcgatgg gcattccaat cctggttgcc    540

ggacaggtaa caggtatcga cagctttgag attggtcaga tggtggggcg gcagctaccg    600

tttatgacca ttatcgtgct gttctggatc atggcgatta tggacggctg gcgcggtatc    660

aaagagacgt ggcctgcggt cgtggttgcg ggcggctcgt ttgccatcgc tcagtacctt    720

agctctaact tcattgggcc ggagctgccg gacattatct cttcgctggt atcactgctc    780

tgcctgacgc tgttcctcaa acgctggcag ccagtgcgtg tattccgttt tggtgatttg    840

ggggcgtcac aggttgatat gacgctggcc cacaccggtt acactgcggg tcaggtgtta    900

cgtgcctgga caccgttcct gttcctgaca gctaccgtaa cactgtggag tatcccgccg    960

tttaaagccc tgttcgcatc gggtggcgcg ctgtatgagt gggtgatcaa tattccggtg   1020
```

```
ccgtacctcg ataaactggt tgcccgtatg ccgccagtgg tcagcgaggc tacagcctat   1080

gccgccgtgt ttaagtttga ctggttctct gccaccggca ccgccattct gtttgctgca   1140

ctgctctcga ttgtctggct gaagatgaaa ccgtctgacg ctatcagcac cttcggcagc   1200

acgctgaaag aactggctct gcccatctac tccatcggta tggtgctggc attcgccttt   1260

atttcgaact attccggact gtcatcaaca ctggcgctgg cactggcgca caccggtcat   1320

gcattcacct tcttctcgcc gttcctcggc tggctggggg tattcctgac cgggtcggat   1380

acctcatcta acgccctgtt cgccgcgctg caagccaccg cagcacaaca aattggcgtc   1440

tctgatctgt tgctggttgc cgccaatacc accggtggcg tcaccggtaa gatgatctcc   1500

ccgcaatcta tcgctatcgc ctgtgcggcg gtaggcctgg tgggcaaaga gtctgatttg   1560

ttccgcttta ctgtcaaaca cagcctgatc ttcacctgta tagtgggcgt gatcaccacg   1620

cttcaggctt atgtcttaac gtggatgatt ccttaa                            1656
```

<210> SEQ ID NO 82
<211> LENGTH: 551
<212> TYPE: PRT
<213> ORGANISM: Escherichia coli

<400> SEQUENCE: 82

```
Met Asn Leu Trp Gln Gln Asn Tyr Asp Pro Ala Gly Asn Ile Trp Leu
1               5                   10                  15

Ser Ser Leu Ile Ala Ser Leu Pro Ile Leu Phe Phe Phe Phe Ala Leu
            20                  25                  30

Ile Lys Leu Lys Leu Lys Gly Tyr Val Ala Ala Ser Trp Thr Val Ala
        35                  40                  45

Ile Ala Leu Ala Val Ala Leu Leu Phe Tyr Lys Met Pro Val Ala Asn
    50                  55                  60

Ala Leu Ala Ser Val Val Tyr Gly Phe Phe Tyr Gly Leu Trp Pro Ile
65                  70                  75                  80

Ala Trp Ile Ile Ile Ala Ala Val Phe Val Tyr Lys Ile Ser Val Lys
                85                  90                  95

Thr Gly Gln Phe Asp Ile Ile Arg Ser Ser Ile Leu Ser Ile Thr Pro
            100                 105                 110

Asp Gln Arg Leu Gln Met Leu Ile Val Gly Phe Cys Phe Gly Ala Phe
        115                 120                 125

Leu Glu Gly Ala Ala Gly Phe Gly Ala Pro Val Ala Ile Thr Ala Ala
    130                 135                 140

Leu Leu Val Gly Leu Gly Phe Lys Pro Leu Tyr Ala Ala Gly Leu Cys
145                 150                 155                 160

Leu Ile Val Asn Thr Ala Pro Val Ala Phe Gly Ala Met Gly Ile Pro
                165                 170                 175

Ile Leu Val Ala Gly Gln Val Thr Gly Ile Asp Ser Phe Glu Ile Gly
            180                 185                 190

Gln Met Val Gly Arg Gln Leu Pro Phe Met Thr Ile Ile Val Leu Phe
        195                 200                 205

Trp Ile Met Ala Ile Met Asp Gly Trp Arg Gly Ile Lys Glu Thr Trp
    210                 215                 220

Pro Ala Val Val Val Ala Gly Gly Ser Phe Ala Ile Ala Gln Tyr Leu
225                 230                 235                 240

Ser Ser Asn Phe Ile Gly Pro Glu Leu Pro Asp Ile Ile Ser Ser Leu
                245                 250                 255

Val Ser Leu Leu Cys Leu Thr Leu Phe Leu Lys Arg Trp Gln Pro Val
```

```
            260                 265                 270

Arg Val Phe Arg Phe Gly Asp Leu Gly Ala Ser Gln Val Asp Met Thr
        275                 280                 285

Leu Ala His Thr Gly Tyr Thr Ala Gly Gln Val Leu Arg Ala Trp Thr
    290                 295                 300

Pro Phe Leu Phe Leu Thr Ala Thr Val Thr Leu Trp Ser Ile Pro Pro
305                 310                 315                 320

Phe Lys Ala Leu Phe Ala Ser Gly Gly Ala Leu Tyr Glu Trp Val Ile
                325                 330                 335

Asn Ile Pro Val Pro Tyr Leu Asp Lys Leu Val Ala Arg Met Pro Pro
            340                 345                 350

Val Val Ser Glu Ala Thr Ala Tyr Ala Ala Val Phe Lys Phe Asp Trp
        355                 360                 365

Phe Ser Ala Thr Gly Thr Ala Ile Leu Phe Ala Ala Leu Leu Ser Ile
    370                 375                 380

Val Trp Leu Lys Met Lys Pro Ser Asp Ala Ile Ser Thr Phe Gly Ser
385                 390                 395                 400

Thr Leu Lys Glu Leu Ala Leu Pro Ile Tyr Ser Ile Gly Met Val Leu
                405                 410                 415

Ala Phe Ala Phe Ile Ser Asn Tyr Ser Gly Leu Ser Ser Thr Leu Ala
            420                 425                 430

Leu Ala Leu Ala His Thr Gly His Ala Phe Thr Phe Phe Ser Pro Phe
        435                 440                 445

Leu Gly Trp Leu Gly Val Phe Leu Thr Gly Ser Asp Thr Ser Ser Asn
    450                 455                 460

Ala Leu Phe Ala Ala Leu Gln Ala Thr Ala Ala Gln Gln Ile Gly Val
465                 470                 475                 480

Ser Asp Leu Leu Leu Val Ala Ala Asn Thr Thr Gly Gly Val Thr Gly
                485                 490                 495

Lys Met Ile Ser Pro Gln Ser Ile Ala Ile Ala Cys Ala Ala Val Gly
            500                 505                 510

Leu Val Gly Lys Glu Ser Asp Leu Phe Arg Phe Thr Val Lys His Ser
        515                 520                 525

Leu Ile Phe Thr Cys Ile Val Gly Val Ile Thr Thr Leu Gln Ala Tyr
    530                 535                 540

Val Leu Thr Trp Met Ile Pro
545                 550


<210> SEQ ID NO 83
<211> LENGTH: 1650
<212> TYPE: DNA
<213> ORGANISM: Escherichia coli

<400> SEQUENCE: 83

atgaaaagag ttctgacggc gcttgccgcc acactccctt tcgcagctaa cgccgcggat      60

gctattagcg gggccgtaga gcgccagcca acgaactggc aggcgattat tatgttcctg     120

attttcgtcg tgtttacgct cggcattacc tactgggcat caaaacgcgt acgttctcgt     180

agcgactact acaccgcagg cggcaatatc actggcttcc agaacgggct ggcgattgcc     240

ggggactata tgtccgccgc ctcattcttg ggatctccg cgctggtgtt tacctccggc     300

tatgacggct taatttactc gctgggcttc ctggtgggct ggccgatcat tttgttcctg     360

attgccgaac gtctgcgtaa cctggggcgc tacacctttg ccgatgtggc ctcttaccgt     420

ctgaaacaag ggccgattcg tattctttcg gcctgtggtt ctctggtggt ggtggcgctt     480
```

```
taccttatcg cccagatggt gggcgcaggt aaactgatcg agctgctgtt tggccttaac    540
tatcacattg cggtggtgct ggtcggcgtg ctgatgatga tgtacgtcct gttcggcggc    600
atgctggcga ccacctgggt gcaaattatc aaagccgtgc tgttgctgtt cggtgccagc    660
tttatggcct ttatggtgat gaaacacgtc ggctttagct tcaacaatct gttcagtgaa    720
gcgatggcgg tacacccgaa aggtgtcgac atcatgaagc cgggcgggct ggtgaaagat    780
ccgatctccg cgctctctct gggtctggga ctgatgtttg gtacggcggg cttgccgcac    840
attctgatgc gcttctttac agtcagcgat gcccgcgaag cacgtaagag cgtgttctac    900
gccaccgggt ttatgggcta cttctatatt ctgaccttta ttatcggctt cggcgcgatc    960
atgctggttg gtgcgaatcc ggaatataaa gacgcggcgg gccatctgat tggtggtaac   1020
aacatggcgg ccgttcacct ggcgaatgca gtgggcggca acctgttcct cggttttatt   1080
tcagcggttg ctttcgccac tatcctcgcg gtggttgcgg gtctgacgct ggcgggcgca   1140
tccgcggttt cgcatgactt gtacgctaac gtcttcaaaa aaggcgcgac cgaacgtgaa   1200
gagctgcggg tatcaaaaat caccgtactg atcctcggcg tgattgcgat tatcctcggc   1260
gtgctgtttg agaatcagaa catcgccttt atggtggggc tggcgtttgc catcgcggcg   1320
agctgtaact tcccgatcat tctgctttct atgtactggt cgaaactgac cacgcgtggc   1380
gcgatgatgg gtggctggct ggggctgatt accgcagtag tactgatgat cctcggcccg   1440
acgatttggg tacagatcct tggtcacgaa aaagccatct tcccgtatga atacccggcg   1500
ctgttctcta tcaccgtggc attcctcggc atctggttct tctcggcaac cgataactca   1560
gcggaaggcg cgcgtgagcg tgaactgttc cgcgcgcagt ttatccgctc ccagaccggc   1620
tttggcgttg agcaaggccg cgcgcattaa                                     1650
```

```
<210> SEQ ID NO 84
<211> LENGTH: 549
<212> TYPE: PRT
<213> ORGANISM: Escherichia coli

<400> SEQUENCE: 84

Met Lys Arg Val Leu Thr Ala Leu Ala Ala Thr Leu Pro Phe Ala Ala
1               5                   10                  15

Asn Ala Ala Asp Ala Ile Ser Gly Ala Val Glu Arg Gln Pro Thr Asn
            20                  25                  30

Trp Gln Ala Ile Ile Met Phe Leu Ile Phe Val Val Phe Thr Leu Gly
        35                  40                  45

Ile Thr Tyr Trp Ala Ser Lys Arg Val Arg Ser Arg Ser Asp Tyr Tyr
    50                  55                  60

Thr Ala Gly Gly Asn Ile Thr Gly Phe Gln Asn Gly Leu Ala Ile Ala
65                  70                  75                  80

Gly Asp Tyr Met Ser Ala Ala Ser Phe Leu Gly Ile Ser Ala Leu Val
                85                  90                  95

Phe Thr Ser Gly Tyr Asp Gly Leu Ile Tyr Ser Leu Gly Phe Leu Val
            100                 105                 110

Gly Trp Pro Ile Ile Leu Phe Leu Ile Ala Glu Arg Leu Arg Asn Leu
        115                 120                 125

Gly Arg Tyr Thr Phe Ala Asp Val Ala Ser Tyr Arg Leu Lys Gln Gly
    130                 135                 140

Pro Ile Arg Ile Leu Ser Ala Cys Gly Ser Leu Val Val Val Ala Leu
145                 150                 155                 160
```

```
Tyr Leu Ile Ala Gln Met Val Gly Ala Gly Lys Leu Ile Glu Leu Leu
                165                 170                 175

Phe Gly Leu Asn Tyr His Ile Ala Val Val Leu Val Gly Val Leu Met
            180                 185                 190

Met Met Tyr Val Leu Phe Gly Gly Met Leu Ala Thr Thr Trp Val Gln
        195                 200                 205

Ile Ile Lys Ala Val Leu Leu Leu Phe Gly Ala Ser Phe Met Ala Phe
    210                 215                 220

Met Val Met Lys His Val Gly Phe Ser Phe Asn Asn Leu Phe Ser Glu
225                 230                 235                 240

Ala Met Ala Val His Pro Lys Gly Val Asp Ile Met Lys Pro Gly Gly
                245                 250                 255

Leu Val Lys Asp Pro Ile Ser Ala Leu Ser Leu Gly Leu Gly Leu Met
            260                 265                 270

Phe Gly Thr Ala Gly Leu Pro His Ile Leu Met Arg Phe Phe Thr Val
        275                 280                 285

Ser Asp Ala Arg Glu Ala Arg Lys Ser Val Phe Tyr Ala Thr Gly Phe
    290                 295                 300

Met Gly Tyr Phe Tyr Ile Leu Thr Phe Ile Ile Gly Phe Gly Ala Ile
305                 310                 315                 320

Met Leu Val Gly Ala Asn Pro Glu Tyr Lys Asp Ala Ala Gly His Leu
                325                 330                 335

Ile Gly Gly Asn Asn Met Ala Ala Val His Leu Ala Asn Ala Val Gly
            340                 345                 350

Gly Asn Leu Phe Leu Gly Phe Ile Ser Ala Val Ala Phe Ala Thr Ile
        355                 360                 365

Leu Ala Val Val Ala Gly Leu Thr Leu Ala Gly Ala Ser Ala Val Ser
    370                 375                 380

His Asp Leu Tyr Ala Asn Val Phe Lys Lys Gly Ala Thr Glu Arg Glu
385                 390                 395                 400

Glu Leu Arg Val Ser Lys Ile Thr Val Leu Ile Leu Gly Val Ile Ala
                405                 410                 415

Ile Ile Leu Gly Val Leu Phe Glu Asn Gln Asn Ile Ala Phe Met Val
            420                 425                 430

Gly Leu Ala Phe Ala Ile Ala Ala Ser Cys Asn Phe Pro Ile Ile Leu
        435                 440                 445

Leu Ser Met Tyr Trp Ser Lys Leu Thr Thr Arg Gly Ala Met Met Gly
    450                 455                 460

Gly Trp Leu Gly Leu Ile Thr Ala Val Val Leu Met Ile Leu Gly Pro
465                 470                 475                 480

Thr Ile Trp Val Gln Ile Leu Gly His Glu Lys Ala Ile Phe Pro Tyr
                485                 490                 495

Glu Tyr Pro Ala Leu Phe Ser Ile Thr Val Ala Phe Leu Gly Ile Trp
            500                 505                 510

Phe Phe Ser Ala Thr Asp Asn Ser Ala Glu Gly Ala Arg Glu Arg Glu
        515                 520                 525

Leu Phe Arg Ala Gln Phe Ile Arg Ser Gln Thr Gly Phe Gly Val Glu
    530                 535                 540

Gln Gly Arg Ala His
545
```

<210> SEQ ID NO 85
<211> LENGTH: 1305
<212> TYPE: DNA

<213> ORGANISM: Escherichia coli

<400> SEQUENCE: 85

```
atgaaaaccc gtacacaaca aattgaagaa ttacagaaag agtggactca accgcgttgg     60
gaaggcatta ctcgcccata cagtgcggaa gatgtggtga aattacgcgg ttcagtcaat    120
cctgaatgca cgctggcgca actgggcgca gcgaaaatgt ggcgtctgct gcacggtgag    180
tcgaaaaaag gctacatcaa cagcctcggc gcactgactg gcggtcaggc gctgcaacag    240
gcgaaagcgg gtattgaagc agtctatctg tcgggatggc aggtagcggc ggacgctaac    300
ctggcggcca gcatgtatcc ggatcagtcg ctctatccgg caaactcggt gccagctgtg    360
gtggagcgga tcaacaacac cttccgtcgt gccgatcaga tccaatggtc cgcgggcatt    420
gagccgggcg atccgcgcta tgtcgattac ttcctgccga tcgttgccga tgcggaagcc    480
ggttttggcg gtgtcctgaa tgcctttgaa ctgatgaaag cgatgattga agccggtgca    540
gcggcagttc acttcgaaga tcagctggcg tcagtgaaga aatgcggtca catgggcggc    600
aaagttttag tgccaactca ggaagctatt cagaaactgg tcgcggcgcg tctggcagct    660
gacgtgacgg gcgttccaac cctgctggtt gcccgtaccg atgctgatgc ggcggatctg    720
atcacctccg attgcgaccc gtatgacagc gaatttatta ccggcgagcg taccagtgaa    780
ggcttcttcc gtactcatgc gggcattgag caagcgatca gccgtggcct ggcgtatgcg    840
ccatatgctg acctggtctg gtgtgaaacc tccacgccgg atctggaact ggcgcgtcgc    900
tttgcacaag ctatccacgc gaaatatccg ggcaaactgc tggcttataa ctgctcgccg    960
tcgttcaact ggcagaaaaa cctcgacgac aaaactattg ccagcttcca gcagcagctg   1020
tcggatatgg gctacaagtt ccagttcatc accctggcag gtatccacag catgtggttc   1080
aacatgtttg acctggcaaa cgcctatgcc cagggcgagg gtatgaagca ctacgttgag   1140
aaagtgcagc agccggaatt tgccgccgcg aaagatggct ataccttcgt atctcaccag   1200
caggaagtgg gtacaggtta cttcgataaa gtgacgacta ttattcaggg cggcacgtct   1260
tcagtcaccg cgctgaccgg ctccactgaa gaatcgcagt tctaa                   1305
```

<210> SEQ ID NO 86
<211> LENGTH: 434
<212> TYPE: PRT
<213> ORGANISM: Escherichia coli

<400> SEQUENCE: 86

```
Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125
```

-continued

```
Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe
```

<210> SEQ ID NO 87
<211> LENGTH: 939
<212> TYPE: DNA
<213> ORGANISM: Escherichia coli

<400> SEQUENCE: 87

```
atggatatca tcttttatca cccaacgttc gatacccaat ggtggattga ggcactgcgc      60

aaagctattc ctcaggcaag agtcagagca tggaaaagcg gagataatga ctctgctgat     120

tatgctttag tctggcatcc tcctgttgaa atgctggcag ggcgcgatct taaagcggtg     180

ttcgcactcg ggccggtgt tgattctatt ttgagcaagc tacaggcaca ccctgaaatg     240

ctgaaccctt ctgttccact tttcgcctg gaagataccg gtatgggcga gcaaatgcag     300

gaatatgctg tcagtcaggt gctgcattgg tttcgacgtt ttgacgatta tcgcatccag     360
```

```
caaaatagtt cgcattggca accgctgcct gaatatcatc gggaagattt taccatcggc    420

attttgggcg caggcgtact gggcagtaaa gttgctcaga gtctgcaaac ctggcgcttt    480

ccgctgcgtt gctggagtcg aacccgtaaa tcgtggcctg gcgtgcaaag ctttgccgga    540

cgggaagaac tgtctgcatt tctgagccaa tgtcgggtat tgattaattt gttaccgaat    600

acccctgaaa ccgtcggcat tattaatcaa caattactcg aaaaattacc ggatggcgcg    660

tatctcctca acctggcgcg tggtgttcat gttgtggaag atgacctgct cgcggcgctg    720

gatagcggca aagttaaagg cgcaatgttg gatgttttta atcgtgaacc cttaccgcct    780

gaaagtccgc tctggcaaca tccacgcgtg acgataacac cacatgtcgc cgcgattacc    840

cgtcccgctg aagctgtgga gtacatttct cgcaccattg cccagctcga aaaaggggag    900

agggtctgcg ggcaagtcga ccgcgcacgc ggctactaa                           939
```

<210> SEQ ID NO 88
<211> LENGTH: 312
<212> TYPE: PRT
<213> ORGANISM: Escherichia coli

<400> SEQUENCE: 88

```
Met Asp Ile Ile Phe Tyr His Pro Thr Phe Asp Thr Gln Trp Trp Ile
1               5                   10                  15

Glu Ala Leu Arg Lys Ala Ile Pro Gln Ala Arg Val Arg Ala Trp Lys
            20                  25                  30

Ser Gly Asp Asn Asp Ser Ala Asp Tyr Ala Leu Val Trp His Pro Pro
        35                  40                  45

Val Glu Met Leu Ala Gly Arg Asp Leu Lys Ala Val Phe Ala Leu Gly
    50                  55                  60

Ala Gly Val Asp Ser Ile Leu Ser Lys Leu Gln Ala His Pro Glu Met
65                  70                  75                  80

Leu Asn Pro Ser Val Pro Leu Phe Arg Leu Glu Asp Thr Gly Met Gly
                85                  90                  95

Glu Gln Met Gln Glu Tyr Ala Val Ser Gln Val Leu His Trp Phe Arg
            100                 105                 110

Arg Phe Asp Asp Tyr Arg Ile Gln Gln Asn Ser Ser His Trp Gln Pro
        115                 120                 125

Leu Pro Glu Tyr His Arg Glu Asp Phe Thr Ile Gly Ile Leu Gly Ala
    130                 135                 140

Gly Val Leu Gly Ser Lys Val Ala Gln Ser Leu Gln Thr Trp Arg Phe
145                 150                 155                 160

Pro Leu Arg Cys Trp Ser Arg Thr Arg Lys Ser Trp Pro Gly Val Gln
                165                 170                 175

Ser Phe Ala Gly Arg Glu Glu Leu Ser Ala Phe Leu Ser Gln Cys Arg
            180                 185                 190

Val Leu Ile Asn Leu Leu Pro Asn Thr Pro Glu Thr Val Gly Ile Ile
        195                 200                 205

Asn Gln Gln Leu Leu Glu Lys Leu Pro Asp Gly Ala Tyr Leu Leu Asn
    210                 215                 220

Leu Ala Arg Gly Val His Val Val Glu Asp Asp Leu Leu Ala Ala Leu
225                 230                 235                 240

Asp Ser Gly Lys Val Lys Gly Ala Met Leu Asp Val Phe Asn Arg Glu
                245                 250                 255

Pro Leu Pro Pro Glu Ser Pro Leu Trp Gln His Pro Arg Val Thr Ile
            260                 265                 270
```

Thr Pro His Val Ala Ala Ile Thr Arg Pro Ala Glu Ala Val Glu Tyr
        275                 280                 285

Ile Ser Arg Thr Ile Ala Gln Leu Glu Lys Gly Glu Arg Val Cys Gly
    290                 295                 300

Gln Val Asp Arg Ala Arg Gly Tyr
305                 310

<210> SEQ ID NO 89
<211> LENGTH: 759
<212> TYPE: DNA
<213> ORGANISM: Escherichia coli

<400> SEQUENCE: 89
atgcattacc agccaaaaca agatttactc aatgatcgca ttatcctggt gacgggagcc 60
agcgatggta ttggtcgtga agccgcgatg acgtatgcac gctatggtgc gacagtgatt 120
ctgttgggcc gtaatgaaga aaaattacgt caggtagcca gccacataaa cgaagaaact 180
gggcgtcagc cacagtggtt tattctcgat ttgctgacct gcacgtccga aaattgccaa 240
caactggcac agcgcattgc cgttaattat ccgcgtctgg atggtgtttt gcataatgcc 300
ggattgctcg gcgatgtttg cccaatgagc gaacaaaatc cgcaggtctg gcaggacgtc 360
atgcaggtca acgttaatgc cacctttatg ctcacccagg cactgcttcc tttattactc 420
aaatcggacg ccggttcact ggtctttact tcatcaagcg ttggacgtca gggacgagcc 480
aactggggtg catatgcagc gtcgaaattt gccaccgaag ggatgatgca ggtactggcc 540
gatgaatatc agcagcgcct gcgtgtcaac tgcattaacc caggcggtac gcgcaccgca 600
atgcgtgcca gcgccttccc gaccgaagat ccacagaaac ttaaaacacc cgctgatatc 660
atgccgctct acctctggct gatgggcgat gacagccgcc gtaaaaccgg catgaccttt 720
gacgcccaac cgggccgtaa accaggaatt tcccaatga 759

<210> SEQ ID NO 90
<211> LENGTH: 252
<212> TYPE: PRT
<213> ORGANISM: Escherichia coli

<400> SEQUENCE: 90

Met His Tyr Gln Pro Lys Gln Asp Leu Leu Asn Asp Arg Ile Ile Leu
1               5                   10                  15

Val Thr Gly Ala Ser Asp Gly Ile Gly Arg Glu Ala Ala Met Thr Tyr
            20                  25                  30

Ala Arg Tyr Gly Ala Thr Val Ile Leu Leu Gly Arg Asn Glu Glu Lys
        35                  40                  45

Leu Arg Gln Val Ala Ser His Ile Asn Glu Glu Thr Gly Arg Gln Pro
    50                  55                  60

Gln Trp Phe Ile Leu Asp Leu Leu Thr Cys Thr Ser Glu Asn Cys Gln
65                  70                  75                  80

Gln Leu Ala Gln Arg Ile Ala Val Asn Tyr Pro Arg Leu Asp Gly Val
                85                  90                  95

Leu His Asn Ala Gly Leu Leu Gly Asp Val Cys Pro Met Ser Glu Gln
            100                 105                 110

Asn Pro Gln Val Trp Gln Asp Val Met Gln Val Asn Val Asn Ala Thr
        115                 120                 125

Phe Met Leu Thr Gln Ala Leu Leu Pro Leu Leu Leu Lys Ser Asp Ala
    130                 135                 140

```
Gly Ser Leu Val Phe Thr Ser Ser Ser Val Gly Arg Gln Gly Arg Ala
145                 150                 155                 160

Asn Trp Gly Ala Tyr Ala Ala Ser Lys Phe Ala Thr Glu Gly Met Met
                165                 170                 175

Gln Val Leu Ala Asp Glu Tyr Gln Gln Arg Leu Arg Val Asn Cys Ile
            180                 185                 190

Asn Pro Gly Gly Thr Arg Thr Ala Met Arg Ala Ser Ala Phe Pro Thr
        195                 200                 205

Glu Asp Pro Gln Lys Leu Lys Thr Pro Ala Asp Ile Met Pro Leu Tyr
    210                 215                 220

Leu Trp Leu Met Gly Asp Asp Ser Arg Arg Lys Thr Gly Met Thr Phe
225                 230                 235                 240

Asp Ala Gln Pro Gly Arg Lys Pro Gly Ile Ser Gln
                245                 250
```

<210> SEQ ID NO 91
<211> LENGTH: 759
<212> TYPE: DNA
<213> ORGANISM: Escherichia coli

<400> SEQUENCE: 91

```
atgcattacc agccaaaaca agatttactc aatgatcgca ttatcctggt gacgggagcc      60

agcgatggta ttggtcgtga agccgcgatg acgtatgcac gctatggtgc gacagtgatt     120

ctgttgggcc gtaatgaaga aaaattacgt caggtagcca gccacataaa cgaagaaact     180

gggcgtcagc cacagtggtt tattctcgat ttgctgacct gcacgtccga aaattgccaa     240

caactggcac agcgcattgc cgttaattat ccgcgtctgg atggtgtttt gcataatgcc     300

ggattgctcg gcgatgtttg cccaatgagc gaacaaaatc cgcaggtctg gcaggacgtc     360

atgcaggtca acgttaatgc cacctttatg ctcacccagg cactgcttcc tttattactc     420

aaatcggacg ccggttcact ggtctttact tcatcaagcg ttggacgtca gggacgagcc     480

aactggggtg catatgcagc gtcgaaattt gccaccgaag ggatgatgca ggtactggcc     540

gatgaatatc agcagcgcct gcgtgtcaac tgcattaacc caggcggtac gcgcaccgca     600

atgcgtgcca gcgccttccc gaccgaagat ccacagaaac ttaaaacacc cgctgatatc     660

atgccgctct acctctggct gatgggcgat gacagccgcc gtaaaaccgg catgaccttt     720

gacgcccaac cgggccgtaa accaggaatt tcccaatga                            759
```

<210> SEQ ID NO 92
<211> LENGTH: 196
<212> TYPE: PRT
<213> ORGANISM: Escherichia coli

<400> SEQUENCE: 92

```
Met Ser Asp Glu Arg Tyr Gln Gln Arg Gln Gln Arg Val Lys Glu Lys
1               5                   10                  15

Val Asp Ala Arg Val Ala Gln Ala Gln Asp Glu Arg Gly Ile Ile Ile
            20                  25                  30

Val Phe Thr Gly Asn Gly Lys Gly Lys Thr Thr Ala Ala Phe Gly Thr
        35                  40                  45

Ala Thr Arg Ala Val Gly His Gly Lys Lys Val Gly Val Val Gln Phe
    50                  55                  60

Ile Lys Gly Thr Trp Pro Asn Gly Glu Arg Asn Leu Leu Glu Pro His
65                  70                  75                  80

Gly Val Glu Phe Gln Val Met Ala Thr Gly Phe Thr Trp Asp Thr Gln
```

```
                85                  90                  95

Asn Arg Glu Ser Asp Thr Ala Ala Cys Arg Glu Val Trp Gln His Ala
            100                 105                 110

Lys Arg Met Leu Ala Asp Ser Ser Leu Asp Met Val Leu Leu Asp Glu
        115                 120                 125

Leu Thr Tyr Met Val Ala Tyr Asp Tyr Leu Pro Leu Glu Glu Val Val
    130                 135                 140

Gln Ala Leu Asn Glu Arg Pro His Gln Gln Thr Val Ile Ile Thr Gly
145                 150                 155                 160

Arg Gly Cys His Arg Asp Ile Leu Glu Leu Ala Asp Thr Val Ser Glu
                165                 170                 175

Leu Arg Pro Val Lys His Ala Phe Asp Ala Gly Val Lys Ala Gln Ile
            180                 185                 190

Gly Ile Asp Tyr
        195


<210> SEQ ID NO 93
<211> LENGTH: 2652
<212> TYPE: DNA
<213> ORGANISM: Escherichia coli

<400> SEQUENCE: 93

atgaacgaac aatattccgc attgcgtagt aatgtcagta tgctcggcaa agtgctggga      60

gaaaccatca aggatgcgtt gggagaacac attcttgaac gcgtagaaac tatccgtaag     120

ttgtcgaaat cttcacgcgc tggcaatgat gctaaccgcc aggagttgct caccacctta     180

caaaatttgt cgaacgacga gctgctgccc gttgcgcgtg cgtttagtca gttcctgaac     240

ctggccaaca ccgccgagca ataccacagc atttcgccga aaggcgaagc tgccagcaac     300

ccggaagtga tcgcccgcac cctgcgtaaa ctgaaaaacc agccggaact gagcgaagac     360

accatcaaaa aagcagtgga atcgctgtcg ctggaactgg tcctcacggc tcacccaacc     420

gaaattaccc gtcgtacact gatccacaaa atggtggaag tgaacgcctg tttaaaacag     480

ctcgataaca aagatatcgc tgactacgaa cacaaccagc tgatgcgtcg cctgcgccag     540

ttgatcgccc agtcatggca taccgatgaa atccgtaagc tgcgtccaag cccggtagat     600

gaagccaaat ggggctttgc cgtagtggaa aacagcctgt ggcaaggcgt accaaattac     660

ctgcgcgaac tgaacgaaca actggaagag aacctcggct acaaactgcc cgtcgaattt     720

gttccggtcc gttttacttc gtggatgggc ggcgaccgcg acggcaaccc gaacgtcact     780

gccgatatca cccgccacgt cctgctactc agccgctgga aagccaccga tttgttcctg     840

aaagatattc aggtgctggt ttctgaactg tcgatggttg aagcgacccc tgaactgctg     900

gcgctggttg gcgaagaagg tgccgcagaa ccgtatcgct atctgatgaa aaacctgcgt     960

tctcgcctga tggcgacaca ggcatggctg gaagcgcgcc tgaaaggcga agaactgcca    1020

aaaccagaag gcctgctgac acaaaacgaa gaactgtggg aaccgctcta cgcttgctac    1080

cagtcacttc aggcgtgtgg catgggtatt atcgccaacg gcgatctgct cgacaccctg    1140

cgccgcgtga aatgtttcgg cgtaccgctg gtccgtattg atatccgtca ggagagcacg    1200

cgtcataccg aagcgctggg cgagctgacc cgctacctcg gtatcggcga ctacgaaagc    1260

tggtcagagg ccgacaaaca ggcgttcctg atccgcgaac tgaactccaa acgtccgctt    1320

ctgccgcgca actggcaacc aagcgccgaa acgcgcgaag tgctcgatac ctgccaggtg    1380

attgccgaag caccgcaagg ctccattgcc gcctacgtga tctcgatggc gaaaacgccg    1440
```

-continued

```
tccgacgtac tggctgtcca cctgctgctg aaagaagcgg gtatcgggtt tgcgatgccg   1500

gttgctccgc tgtttgaaac cctcgatgat ctgaacaacg ccaacgatgt catgacccag   1560

ctgctcaata ttgactggta tcgtggcctg attcagggca aacagatggt gatgattggc   1620

tattccgact cagcaaaaga tgcgggagtg atggcagctt cctgggcgca atatcaggca   1680

caggatgcat taatcaaaac ctgcgaaaaa gcgggtattg agctgacgtt gttccacggt   1740

cgcggcggtt ccattggtcg cggcggcgca cctgctcatg cggcgctgct gtcacaaccg   1800

ccaggaagcc tgaaaggcgg cctgcgcgta accgaacagg gcgagatgat ccgctttaaa   1860

tatggtctgc cagaaatcac cgtcagcagc ctgtcgcttt ataccggggc gattctggaa   1920

gccaacctgc tgccaccgcc ggagccgaaa gagagctggc gtcgcattat ggatgaactg   1980

tcagtcatct cctgcgatgt ctaccgcggc tacgtacgtg aaaacaaaga ttttgtgcct   2040

tacttccgct ccgctacgcc ggaacaagaa ctgggcaaac tgccgttggg ttcacgtccg   2100

gcgaaacgtc gcccaaccgg cggcgtcgag tcactacgcg ccattccgtg gatcttcgcc   2160

tggacgcaaa accgtctgat gctccccgcc tggctgggtg caggtacggc gctgcaaaaa   2220

gtggtcgaag acggcaaaca gagcgagctg gaggctatgt gccgcgattg gccattcttc   2280

tcgacgcgtc tcggcatgct ggagatggtc ttcgccaaag cagacctgtg gctggcggaa   2340

tactatgacc aacgcctggt agacaaagca ctgtggccgt taggtaaaga gttacgcaac   2400

ctgcaagaag aagacatcaa agtggtgctg gcgattgcca acgattccca tctgatggcc   2460

gatctgccgt ggattgcaga gtctattcag ctacggaata tttacaccga cccgctgaac   2520

gtattgcagg ccgagttgct gcaccgctcc cgccaggcag aaaaagaagg ccaggaaccg   2580

gatcctcgcg tcgaacaagc gttaatggtc actattgccg ggattgcggc aggtatgcgt   2640

aataccggct aa                                                       2652
```

<210> SEQ ID NO 94
<211> LENGTH: 883
<212> TYPE: PRT
<213> ORGANISM: Escherichia coli

<400> SEQUENCE: 94

```
Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160
```

-continued

```
Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575
```

-continued

```
Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly


<210> SEQ ID NO 95
<211> LENGTH: 1395
<212> TYPE: DNA
<213> ORGANISM: Escherichia coli

<400> SEQUENCE: 95

atgcctgacg ctaaaaaaca ggggcggtca aacaaggcaa tgacgttttt cgtctgcttc      60

cttgccgctc tggcgggatt actctttggc ctggatatcg gtgtaattgc tggcgcactg     120

ccgtttattg cagatgaatt ccagattact tcgcacacgc aagaatgggt cgtaagctcc     180

atgatgttcg gtgcggcagt cggtgcggtg ggcagcggct ggctctcctt taaactcggg     240

cgcaaaaaga gcctgatgat cggcgcaatt ttgtttgttg ccggttcgct gttctctgcg     300

gctgcgccaa acgttgaagt actgattctt tcccgcgttc tactggggct ggcggtgggt     360
```

```
gtggcctctt ataccgcacc gctgtacctc tctgaaattg cgccggaaaa aattcgtggc    420

agtatgatct cgatgtatca gttgatgatc actatcggga tcctcggtgc ttatctttct    480

gataccgcct tcagctacac cggtgcatgg cgctggatgc tgggtgtgat tatcatcccg    540

gcaattttgc tgctgattgg tgtcttcttc ctgccagaca gcccacgttg gtttgccgcc    600

aaacgccgtt ttgttgatgc cgaacgcgtg ctgctacgcc tgcgtgacac cagcgcggaa    660

gcgaaacgcg aactggatga aatccgtgaa agtttgcagg ttaaacagag tggctgggcg    720

ctgtttaaag agaacagcaa cttccgccgc gcggtgttcc ttggcgtact gttgcaggta    780

atgcagcaat tcaccgggat gaacgtcatc atgtattacg cgccgaaaat cttcgaactg    840

gcgggttata ccaacactac cgagcaaatg tgggggaccg tgattgtcgg cctgaccaac    900

gtacttgcca cctttatcgc aatcggcctt gttgaccgct ggggacgtaa accaacgcta    960

acgctgggct tcctggtgat ggctgctggc atgggcgtac tcggtacaat gatgcatatc   1020

ggtattcact ctccgtcggc gcagtatttc gccatcgcca tgctgctgat gtttattgtc   1080

ggttttgcca tgagtgccgg tccgctgatt tgggtactgt gctccgaaat tcagccgctg   1140

aaaggccgcg attttggcat cacctgctcc actgccacca actggattgc caacatgatc   1200

gttggcgcaa cgttcctgac catgctcaac acgctgggta acgccaacac cttctgggtg   1260

tatgcggctc tgaacgtact gtttatcctg ctgacattgt ggctggtacc ggaaaccaaa   1320

cacgtttcgc tggaacatat tgaacgtaat ctgatgaaag gtcgtaaact gcgcgaaata   1380

ggcgctcacg attaa                                                    1395
```

<210> SEQ ID NO 96
<211> LENGTH: 464
<212> TYPE: PRT
<213> ORGANISM: Escherichia coli

<400> SEQUENCE: 96

```
Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Ala Pro Asn Val Glu Val Leu Ile Leu Ser Arg
            100                 105                 110

Val Leu Leu Gly Leu Ala Val Gly Val Ala Ser Tyr Thr Ala Pro Leu
        115                 120                 125

Tyr Leu Ser Glu Ile Ala Pro Glu Lys Ile Arg Gly Ser Met Ile Ser
    130                 135                 140

Met Tyr Gln Leu Met Ile Thr Ile Gly Ile Leu Gly Ala Tyr Leu Ser
145                 150                 155                 160

Asp Thr Ala Phe Ser Tyr Thr Gly Ala Trp Arg Trp Met Leu Gly Val
                165                 170                 175

Ile Ile Ile Pro Ala Ile Leu Leu Leu Ile Gly Val Phe Phe Leu Pro
            180                 185                 190
```

```
Asp Ser Pro Arg Trp Phe Ala Ala Lys Arg Arg Phe Val Asp Ala Glu
        195                 200                 205

Arg Val Leu Leu Arg Leu Arg Asp Thr Ser Ala Glu Ala Lys Arg Glu
    210                 215                 220

Leu Asp Glu Ile Arg Glu Ser Leu Gln Val Lys Gln Ser Gly Trp Ala
225                 230                 235                 240

Leu Phe Lys Glu Asn Ser Asn Phe Arg Arg Ala Val Phe Leu Gly Val
                245                 250                 255

Leu Leu Gln Val Met Gln Gln Phe Thr Gly Met Asn Val Ile Met Tyr
            260                 265                 270

Tyr Ala Pro Lys Ile Phe Glu Leu Ala Gly Tyr Thr Asn Thr Thr Glu
        275                 280                 285

Gln Met Trp Gly Thr Val Ile Val Gly Leu Thr Asn Val Leu Ala Thr
    290                 295                 300

Phe Ile Ala Ile Gly Leu Val Asp Arg Trp Gly Arg Lys Pro Thr Leu
305                 310                 315                 320

Thr Leu Gly Phe Leu Val Met Ala Ala Gly Met Gly Val Leu Gly Thr
                325                 330                 335

Met Met His Ile Gly Ile His Ser Pro Ser Ala Gln Tyr Phe Ala Ile
            340                 345                 350

Ala Met Leu Leu Met Phe Ile Val Gly Phe Ala Met Ser Ala Gly Pro
        355                 360                 365

Leu Ile Trp Val Leu Cys Ser Glu Ile Gln Pro Leu Lys Gly Arg Asp
    370                 375                 380

Phe Gly Ile Thr Cys Ser Thr Ala Thr Asn Trp Ile Ala Asn Met Ile
385                 390                 395                 400

Val Gly Ala Thr Phe Leu Thr Met Leu Asn Thr Leu Gly Asn Ala Asn
                405                 410                 415

Thr Phe Trp Val Tyr Ala Ala Leu Asn Val Leu Phe Ile Leu Leu Thr
            420                 425                 430

Leu Trp Leu Val Pro Glu Thr Lys His Val Ser Leu Glu His Ile Glu
        435                 440                 445

Arg Asn Leu Met Lys Gly Arg Lys Leu Arg Glu Ile Gly Ala His Asp
    450                 455                 460
```

<210> SEQ ID NO 97
<211> LENGTH: 966
<212> TYPE: DNA
<213> ORGANISM: Escherichia coli

<400> SEQUENCE: 97

```
atgacaaagt atgcattagt cggtgatgtg ggcggcacca acgcacgtct tgctctgtgt      60

gatattgcca gtggtgaaat ctcgcaggct aagacctatt cagggcttga ttaccccagc     120

ctcgaagcgg tcattcgcgt ttatcttgaa gaacataagg tcgaggtgaa agacggctgt     180

attgccatcg cttgcccaat taccggtgac tgggtggcga tgaccaacca tacctgggcg     240

ttctcaattg ccgaaatgaa aaagaatctc ggttttagcc atctggaaat tattaacgat     300

tttaccgctg tatcgatggc gatcccgatg ctgaaaaaag agcatctgat tcagtttggt     360

ggcgcagaac cggtcgaagg taagcctatt gcggtttacg gtgccggaac ggggcttggg     420

gttgcgcatc tggtccatgt cgataagcgt tgggtaagct tgccaggcga aggcggtcac     480

gttgattttg cgccgaatag tgaagaagag gccattatcc tcgaaatatt gcgtgcggaa     540

attggtcatg tttcggcgga gcgcgtgctt tctggccctg ggctggtgaa tttgtatcgc     600
```

-continued

```
gcaattgtga aagctgacaa ccgcctgcca gaaaatctca agccaaaaga tattaccgaa    660

cgcgcgctgg ctgacagctg caccgattgc cgccgcgcat tgtcgctgtt ttgcgtcatt    720

atgggccgtt ttggcggcaa tctggcgctc aatctcggga catttggcgg cgtgtttatt    780

gcgggcggta tcgtgccgcg cttccttgag ttcttcaaag cctccggttt ccgtgccgca    840

tttgaagata aagggcgctt taaagaatat gtccatgata ttccggtgta tctcatcgtc    900

catgacaatc cgggccttct cggttccggt gcacatttac gccagacctt aggtcacatt    960

ctgtaa                                                               966
```

<210> SEQ ID NO 98
<211> LENGTH: 321
<212> TYPE: PRT
<213> ORGANISM: Escherichia coli

<400> SEQUENCE: 98

```
Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
    50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
        195                 200                 205

Leu Pro Glu Asn Leu Lys Pro Lys Asp Ile Thr Glu Arg Ala Leu Ala
    210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
            260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
    290                 295                 300
```

```
Gly Leu Leu Gly Ser Gly Ala His Leu Arg Gln Thr Leu Gly His Ile
305                 310                 315                 320

Leu


<210> SEQ ID NO 99
<211> LENGTH: 1668
<212> TYPE: DNA
<213> ORGANISM: Klebsiella pneumoniae

<400> SEQUENCE: 99

ttattcaatg gtgtcgggct gaaccacgcc cggaatattt ttgatctccg cccagcgttc      60

ggcagagatg cgatagccgg tgcccggccc ctgatagtca ttgatgtcgt tgaccgcact     120

caccacctcg aactgccgat cgagaatggc cgaggtctgc aggtaatcgc cggtgacccg     180

ctggcgcagc atattgagaa tattgctggc gatatcctca aagccgctgc ggctcagcgc     240

gccgacaata tcgaggccgg tgatgttgcg cttcatcatc tcttccaccg cactcagatc     300

ctccaccacg ttacgcggcg gcatctcgtt gctgccgtgc gcgtaggtgg cggcctccac     360

ctcctcgtcg gcgattggcg gcagccccag ctcgcggaaa accgcctgga tcgcccgcgc     420

cgctttctgg cgaatggcaa tggtttccgc ctcggtcacc ggacgcaggc cgccgtcaac     480

catcaggtca cgctgcagga tgttgtaatc atcaaaatct tccgcatcga agttcgagcc     540

ggcgaacatg ttgtcgtagt tcggcaccgc gctgtagccg gagaaaataa agtcggtgcc     600

cggcagcatc tgcatcaggg tgcgcgcggt gcggcgaata tccgagtggg agaaagtctg     660

gtcgttggcg gacgccactt cgaggtcgag catagaggcg atcaggtttt ccgccagcac     720

cgcccgaatg cccgacggca cagcgccggt catgccgata cagctcaccg cgccgttttg     780

cagtccctga accccggcgc ctttagtaat gaagatgcag cgcgattcga ggtagagcat     840

cgacttgctc tccgaatagc ccatcagcgc ttcggatccg gtgccggagg tgtagcgcat     900

tttcaacccg cgggaggcgt aggccgaggc gaggaacgcc tttgaccacg gcgtatcatc     960

gccgtcggta aataccgctt cggtgccgta gaccgacacc gtctcggcgt agctggttaa    1020

gccacgcatg cccagctcca gctcggtggc ctcttccacc gagcactgcg tcaacacgcc    1080

ggggcggccg cactgcgaac cgaccaacag cgccagggcg ttaaacggcg cgtagcgcgc    1140

gataccgacc gtggtctcct gttctgagaa gccgcggatc ccggcctcgg cggcgtcagc    1200

ggcaatctgc accggattat ctttgagatt ggtgacgtgg cactggttgg agggggtccg    1260

gcgggcacgc atcttctgca gcgccatcat catctccacc acgttcatct gcgccatcac    1320

ctcgaccgct ttggccggcg tgatggcggt agtgatggca atgatctcct cccggctgac    1380

gtgaatatcc accagcatac gggctatttc caccgcctcc aggcgcattg cctgctctgt    1440

gcgctcaacg ttgatcgcgt aatcggcgat aaatcggtcg atcatgtcaa actggtcccg    1500

gcgtttgccg tccagttcga cgatcagacc gttgtccact tttactgaag agaccgggtc    1560

aaaggggctg tccatggcga tcagcccctc ttcaggccac tcgccaatca gcccgtcctg    1620

attgacgggg cgctgggcca gtactgcaaa tcgttttgat cttttcat                 1668


<210> SEQ ID NO 100
<211> LENGTH: 555
<212> TYPE: PRT
<213> ORGANISM: Klebsiella pneumoniae

<400> SEQUENCE: 100

Met Lys Arg Ser Lys Arg Phe Ala Val Leu Ala Gln Arg Pro Val Asn
```

-continued

```
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335

Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
    370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430
```

```
Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555


<210> SEQ ID NO 101
<211> LENGTH: 441
<212> TYPE: DNA
<213> ORGANISM: Klebsiella pneumoniae

<400> SEQUENCE: 101

tcactccctt actaagtcga tgtgcagggt gacgggctcg gcgtcctgca ccacatgttt      60

ggtctctttg atatgaaata gcgcggcttt ggccataaat ttcggccgca ccatctgatc     120

gttcaccacc ggcaccggcg aaggtgactc tttgcgcgca tagcgcgcag cgtttttgcc     180

aatctgccgg taggtctcca gcgtcagcag cggcgcctgg gagaacagct ccaggttgct     240

gagcggcagc agatcgcgct gatggatgac cgtggtcccc ttcgactgga taccgatgcc     300

gatccccgag ccgctcaggt tggccgcatc ccaggccata aaggagacgt cggacgtgcg     360

cagaatgcgc accacccggg cgtgaagccc ctcttcttcc accccggcaa tcagctcttt     420

gaggatcgcg ccatggggca t                                               441


<210> SEQ ID NO 102
<211> LENGTH: 194
<212> TYPE: PRT
<213> ORGANISM: Klebsiella pneumoniae

<400> SEQUENCE: 102

Met Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
```

```
        115                 120                 125

Leu Glu Thr Tyr Arg Gln Ile Gly Lys Asn Ala Ala Arg Tyr Ala Arg
    130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Val Asp Leu Val
            180                 185                 190

Arg Glu


<210> SEQ ID NO 103
<211> LENGTH: 426
<212> TYPE: DNA
<213> ORGANISM: Klebsiella pneumoniae

<400> SEQUENCE: 103

ttagcttcct ttacgcagct tatgccgctg ctgatacact tccgccgact cccggacaaa      60

ggcggcattc actgtcgcat gccaggtgtg ctccagctcg tcggcgatcg ccagcagctc     120

cgcctgcgag gagcggaacg ggcgcagcgc gttatagata gccagaatgc gctcgtcagg     180

aatggcgata agctccgccg cgcggcggaa attgcgcgcc accgcatggc gctgcatctg     240

ctcggcaatc tgcgcctggt actcaagggt ctggcgggag atccgcacat cctgcgggcc     300

cacctcgcca gagagcacct tctcgagggt aatatcggtc aatggtttgc cggtaggcgt     360

caggatatgc tccgggcagc gggtggctaa cggataatcc tgcacgcgca tggttttctc     420

gctcat                                                                426


<210> SEQ ID NO 104
<211> LENGTH: 141
<212> TYPE: PRT
<213> ORGANISM: Klebsiella pneumoniae

<400> SEQUENCE: 104

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140


<210> SEQ ID NO 105
<211> LENGTH: 1824
<212> TYPE: DNA
```

<213> ORGANISM: Klebsiella pneumoniae

<400> SEQUENCE: 105

```
ttaattcgcc tgaccggcca gtagcagccc ggtggcgacc gcattgcgcg gcccttctgt     60
tccccgaata ttgccctgcc cggcgaccac gccatagtgc gacaaggctt ccgtgataag    120
ctgcgggatc tcaaagtcca gcgatgagcc gcccaccagc accacaaagg cgatatcgcg    180
aatggaaccg ccgggtgaga cctggcgcag cgcgcgcagg cagttggtga caaacacttt    240
ctctttcgcc tgccggcgca cgagacgaat tttttccagc gggctggcgt tatcgatcgg    300
caccagttcg ccctccttga tgtacaccac tttggcgaac accgccgggc tgagggcttc    360
ccgaaagaac tccaccgcgc cattctcgtg acgaatactg aacaggcttt ccactttggc    420
cagcgggtat ttttttatcg cttccgccag cgaaagatcc tcgaggccca gctcggtttt    480
aatcaacagg ctgaccatat tccccgcccc ggcgagatgg accgccgtta tctgcccctc    540
cgcgttgacg atcgccgcat ccgtcgagcc ggcgccgagg tcgaggatcg ccagcggcgc    600
cgcacagccg ggagtggtta acgccccggc gatggccatg ttggcctcca cgccgcccac    660
caccacctcg gtctgcagtc gggcgctcag ttcgcgggcg ataacctgca tttgcagacg    720
atccgctttc accatcgccg ccatcccgac ggcattctcc atggcgcact cgccggccat    780
cccgccctgc accttgcgcg gaataaacgt atccaccgcc agcagatcct ggatgtatat    840
cgcgctcatc tcatggccgg tcagggacgc cattaccttg cgcacccgct caagcatgcc    900
gccggcgtgg gtgcccggtt cgccgcggat gtcgcgtacc ggagcgcagg cgctcatcgc    960
ctgcatgatg gcttccgcgc cctcggcgac atcggcctct ccgcggcgct tttcgccgct   1020
aatgtagagg ttgcccgccg ggatcacccg cgactgcaca tccccctgcg ggtcttgag    1080
caccaccgcg gaacggttgc caatcagggc gcgggcgatg gggacgatgg cctgggtctc   1140
ttccgggctt agcccgaaga aggtggcgat cccgtaggga ttcgacagga tccgcaccac   1200
ctggcccggc gcggccactt ccaccgccgc cattaccccc tcggggacct gctccagcag   1260
cgtcacttca tccaccaccg gcagggtttt acgcaggcgg ttgttcacca gcacgccgtc   1320
gtcctttttg aggatcgccg ccaccacgtt gatcccccgg tcgagcgcct cattgagcca   1380
ccacacggcg tcaaggaaat cgacggcgtc gtcaatcagt acgatccacc cctcggcata   1440
ctgcgccgcc ggcagcgtcg ccagccgccc gagggcgata gtcgtcccca cgccaacgcc   1500
caccccgccc ggcgtctgcg ggttatgacc gatcatggtc gattcggtga taatggtctc   1560
ggtgatggtc tccatcgcca catcgccaat caccggcgcg gcttcgttaa gatagatgcg   1620
agagacatcg ctcatcgacc acggtgtttt cgccagggcc tgctccagcg cggcgagggt   1680
cccggcgata ttgtcccgcg tccctttcat gcccgtcgtc gcgacgatcc cgctggcaac   1740
aaacgccctc gcctgcgggt agtcggacgc cagcgccacc tcggtggtgg cgttgccgat   1800
atcaatcccg gctattaacg gcat                                          1824
```

<210> SEQ ID NO 106
<211> LENGTH: 607
<212> TYPE: PRT
<213> ORGANISM: Klebsiella pneumoniae

<400> SEQUENCE: 106

```
Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30
```

-continued

```
Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

Val Val Arg Ile Leu Ser Asn Pro Tyr Gly Ile Ala Thr Phe Phe Gly
    210                 215                 220

Leu Ser Pro Glu Glu Thr Gln Ala Ile Val Pro Ile Ala Arg Ala Leu
225                 230                 235                 240

Ile Gly Asn Arg Ser Ala Val Val Leu Lys Thr Pro Gln Gly Asp Val
                245                 250                 255

Gln Ser Arg Val Ile Pro Ala Gly Asn Leu Tyr Ile Ser Gly Glu Lys
            260                 265                 270

Arg Arg Gly Glu Ala Asp Val Ala Glu Gly Ala Glu Ala Ile Met Gln
        275                 280                 285

Ala Met Ser Ala Cys Ala Pro Val Arg Asp Ile Arg Gly Glu Pro Gly
    290                 295                 300

Thr His Ala Gly Gly Met Leu Glu Arg Val Arg Lys Val Met Ala Ser
305                 310                 315                 320

Leu Thr Gly His Glu Met Ser Ala Ile Tyr Ile Gln Asp Leu Leu Ala
                325                 330                 335

Val Asp Thr Phe Ile Pro Arg Lys Val Gln Gly Gly Met Ala Gly Glu
            340                 345                 350

Cys Ala Met Glu Asn Ala Val Gly Met Ala Ala Met Val Lys Ala Asp
        355                 360                 365

Arg Leu Gln Met Gln Val Ile Ala Arg Glu Leu Ser Ala Arg Leu Gln
    370                 375                 380

Thr Glu Val Val Val Gly Gly Val Glu Ala Asn Met Ala Ile Ala Gly
385                 390                 395                 400

Ala Leu Thr Thr Pro Gly Cys Ala Ala Pro Leu Ala Ile Leu Asp Leu
                405                 410                 415

Gly Ala Gly Ser Thr Asp Ala Ala Ile Val Asn Ala Glu Gly Gln Ile
            420                 425                 430

Thr Ala Val His Leu Ala Gly Ala Gly Asn Met Val Ser Leu Leu Ile
        435                 440                 445
```

```
Lys Thr Glu Leu Gly Leu Glu Asp Leu Ser Leu Ala Glu Ala Ile Lys
    450                 455                 460

Lys Tyr Pro Leu Ala Lys Val Glu Ser Leu Phe Ser Ile Arg His Glu
465                 470                 475                 480

Asn Gly Ala Val Glu Phe Phe Arg Glu Ala Leu Ser Pro Ala Val Phe
                485                 490                 495

Ala Lys Val Val Tyr Ile Lys Glu Gly Glu Leu Val Pro Ile Asp Asn
            500                 505                 510

Ala Ser Pro Leu Glu Lys Ile Arg Leu Val Arg Arg Gln Ala Lys Glu
        515                 520                 525

Lys Val Phe Val Thr Asn Cys Leu Arg Ala Leu Arg Gln Val Ser Pro
    530                 535                 540

Gly Gly Ser Ile Arg Asp Ile Ala Phe Val Val Leu Val Gly Gly Ser
545                 550                 555                 560

Ser Leu Asp Phe Glu Ile Pro Gln Leu Ile Thr Glu Ala Leu Ser His
                565                 570                 575

Tyr Gly Val Val Ala Gly Gln Gly Asn Ile Arg Gly Thr Glu Gly Pro
            580                 585                 590

Arg Asn Ala Val Ala Thr Gly Leu Leu Leu Ala Gly Gln Ala Asn
        595                 600                 605
```

<210> SEQ ID NO 107
<211> LENGTH: 513
<212> TYPE: DNA
<213> ORGANISM: Klebsiella pneumoniae

<400> SEQUENCE: 107

```
atgaacgtac gcacttgcac tgaatctgac gtcgcctcta tcgcagtcgt atttactgag      60

tctattcatg tacttggagc gtctcactat gacgcttcgc aaaggaatgc gtgggcaccg     120

cgtcccgcag atatagaggc ttggtcagct cgcttatctg gcctacagac tcttctagca     180

attgagggag atgcggttat cgggttcatc tcttacgagc ttagcggcca catcgagttt     240

ctttacaccg caccgggttc cgagcgtcgg ggcgtcgcgt ctgttctgta ccgtgaggtt     300

gagaaagccc tcccaggtgt ttcgctcttc acagaagcca gtctggtcgc caagcccttt     360

ttcctgcggc atggtttcag tgtagttgag gagcaaaatg tctcccgtgg aggcgtcatg     420

ttccgtaggt atgcaatgcg caaggcagtt gtcgcccaac atggcgctca agccgaccgg     480

ccagccctgc gggctgtccg tcggcttagc tag                                  513
```

<210> SEQ ID NO 108
<211> LENGTH: 170
<212> TYPE: PRT
<213> ORGANISM: Klebsiella pneumoniae

<400> SEQUENCE: 108

```
Met Asn Val Arg Thr Cys Thr Glu Ser Asp Val Ala Ser Ile Ala Val
1               5                   10                  15

Val Phe Thr Glu Ser Ile His Val Leu Gly Ala Ser His Tyr Asp Ala
            20                  25                  30

Ser Gln Arg Asn Ala Trp Ala Pro Arg Pro Ala Asp Ile Glu Ala Trp
        35                  40                  45

Ser Ala Arg Leu Ser Gly Leu Gln Thr Leu Leu Ala Ile Glu Gly Asp
    50                  55                  60

Ala Val Ile Gly Phe Ile Ser Tyr Glu Leu Ser Gly His Ile Glu Phe
65                  70                  75                  80
```

-continued

Leu Tyr Thr Ala Pro Gly Ser Glu Arg Arg Gly Val Ala Ser Val Leu
85 90 95

Tyr Arg Glu Val Glu Lys Ala Leu Pro Gly Val Ser Leu Phe Thr Glu
100 105 110

Ala Ser Leu Val Ala Lys Pro Phe Phe Leu Arg His Gly Phe Ser Val
115 120 125

Val Glu Glu Gln Asn Val Ser Arg Gly Gly Val Met Phe Arg Arg Tyr
130 135 140

Ala Met Arg Lys Ala Val Val Ala Gln His Gly Ala Gln Ala Asp Arg
145 150 155 160

Pro Ala Leu Arg Ala Val Arg Arg Leu Ser
165 170

<210> SEQ ID NO 109
<211> LENGTH: 1176
<212> TYPE: DNA
<213> ORGANISM: Saccharomyces cerevisiae

<400> SEQUENCE: 109
atgtctgctg ctgctgatag attaaactta acttccggcc acttgaatgc tggtagaaag 60
agaagttcct cttctgtttc tttgaaggct gccgaaaagc ctttcaaggt tactgtgatt 120
ggatctggta actggggtac tactattgcc aaggtggttg ccgaaaattg taagggatac 180
ccagaagttt tcgctccaat agtacaaatg tgggtgttcg aagaagagat caatggtgaa 240
aaattgactg aaatcataaa tactagacat caaaacgtga aatacttgcc tggcatcact 300
ctacccgaca atttggttgc taatccagac ttgattgatt cagtcaagga tgtcgacatc 360
atcgttttca acattccaca tcaatttttg ccccgtatct gtagccaatt gaaaggtcat 420
gttgattcac acgtcagagc tatctcctgt ctaaagggtt ttgaagttgg tgctaaaggt 480
gtccaattgc tatcctctta catcactgag gaactaggta ttcaatgtgg tgctctatct 540
ggtgctaaca ttgccaccga agtcgctcaa gaacactggt ctgaaacaac agttgcttac 600
cacattccaa aggatttcag aggcgagggc aaggacgtcg accataaggt tctaaaggcc 660
ttgttccaca gaccttactt ccacgttagt gtcatcgaag atgttgctgg tatctccatc 720
tgtggtgctt tgaagaacgt tgttgcctta ggttgtggtt tcgtcgaagg tctaggctgg 780
ggtaacaacg cttctgctgc catccaaaga gtcggtttgg gtgagatcat cagattcggt 840
caaatgtttt tcccagaatc tagagaagaa acatactacc aagagtctgc tggtgttgct 900
gatttgatca ccacctgcgc tggtggtaga aacgtcaagg ttgctaggct aatggctact 960
tctggtaagg acgcctggga atgtgaaaag gagttgttga atggccaatc cgctcaaggt 1020
ttaattacct gcaaagaagt tcacgaatgg ttggaaacat gtggctctgt cgaagacttc 1080
ccattatttg aagccgtata ccaaatcgtt tacaacaact acccaatgaa gaacctgccg 1140
gacatgattg aagaattaga tctacatgaa gattag 1176

<210> SEQ ID NO 110
<211> LENGTH: 391
<212> TYPE: PRT
<213> ORGANISM: Saccharomyces cerevisiae

<400> SEQUENCE: 110

Met Ser Ala Ala Ala Asp Arg Leu Asn Leu Thr Ser Gly His Leu Asn
1 5 10 15

Ala Gly Arg Lys Arg Ser Ser Ser Ser Val Ser Leu Lys Ala Ala Glu
20 25 30

```
Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 111
<211> LENGTH: 753
<212> TYPE: DNA
<213> ORGANISM: Saccharomyces cerevisiae

<400> SEQUENCE: 111
atgggattga ctactaaacc tctatctttg aaagttaacg ccgctttgtt cgacgtcgac 60

```
ggtaccatta tcatctctca accagccatt gctgcattct ggagggattt cggtaaggac    120

aaaccttatt tcgatgctga acacgttatc caagtctcgc atggttggag aacgtttgat    180

gccattgcta agttcgctcc agactttgcc aatgaagagt atgttaacaa attagaagct    240

gaaattccgg tcaagtacgg tgaaaaatcc attgaagtcc caggtgcagt taagctgtgc    300

aacgctttga acgctctacc aaaagagaaa tgggctgtgg caacttccgg tacccgtgat    360

atggcacaaa aatggttcga gcatctggga atcaggagac caaagtactt cattaccgct    420

aatgatgtca aacagggtaa gcctcatcca gaaccatatc tgaagggcag gaatggctta    480

ggatatccga tcaatgagca agacccttcc aaatctaagg tagtagtatt tgaagacgct    540

ccagcaggta ttgccgccgg aaaagccgcc ggttgtaaga tcattggtat tgccactact    600

ttcgacttgg acttcctaaa ggaaaaaggc tgtgacatca ttgtcaaaaa ccacgaatcc    660

atcagagttg gcggctacaa tgccgaaaca gacgaagttg aattcatttt tgacgactac    720

ttatatgcta aggacgatct gttgaaatgg taa                                 753
```

```
<210> SEQ ID NO 112
<211> LENGTH: 250
<212> TYPE: PRT
<213> ORGANISM: Saccharomyces cerevisiae

<400> SEQUENCE: 112

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Ile Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Gly Tyr Asn Ala Glu Thr Asp Glu Val Glu Phe Ile Phe Asp Asp Tyr
225                 230                 235                 240

Leu Tyr Ala Lys Asp Asp Leu Leu Lys Trp
```

245 250

<210> SEQ ID NO 113
<211> LENGTH: 996
<212> TYPE: DNA
<213> ORGANISM: Escherichia coli

<400> SEQUENCE: 113
atgactatca aagtaggtat caacggtttt ggccgtatcg gtcgcattgt tttccgtgct 60
gctcagaaac gttctgacat cgagatcgtt gcaatcaacg acctgttaga cgctgattac 120
atggcataca tgctgaaata tgactccact cacggccgtt tcgacggtac cgttgaagtg 180
aaagacggtc atctgatcgt taacggtaaa aaaatccgtg ttaccgctga acgtgatccg 240
gctaacctga aatgggacga agttggtgtt gacgttgtcg ctgaagcaac tggtctgttc 300
ctgactgacg aaactgctcg taaacacatc accgctggtg cgaagaaagt ggttatgact 360
ggtccgtcta aagacaacac tccgatgttc gttaaaggcg ctaacttcga caaatatgct 420
ggccaggaca tcgtttccaa cgcttcctgc accaccaact gcctggctcc gctggctaaa 480
gttatcaacg ataacttcgg catcatcgaa ggtctgatga ccaccgttca cgctactacc 540
gctactcaga aaaccgttga tggcccgtct cacaaagact ggcgcggcgg ccgcggcgct 600
tcccagaaca tcatcccgtc ctctaccggt gctgctaaag ctgtaggtaa agtactgcca 660
gaactgaatg gcaaactgac tggtatggcg ttccgcgttc cgaccccgaa cgtatctgta 720
gttgacctga ccgttcgtct ggaaaaagct gcaacttacg agcagatcaa agctgccgtt 780
aaagctgctg ctgaaggcga aatgaaaggc gttctgggct acaccgaaga tgacgtagta 840
tctaccgatt tcaacggcga agtttgcact tccgtgttcg atgctaaagc tggtatcgct 900
ctgaacgaca acttcgtgaa actggtatcc tggtacgaca acgaaaccgg ttactccaac 960
aaagttctgg acctgatcgc tcacatctcc aaataa 996

<210> SEQ ID NO 114
<211> LENGTH: 331
<212> TYPE: PRT
<213> ORGANISM: Escherichia coli

<400> SEQUENCE: 114

Met Thr Ile Lys Val Gly Ile Asn Gly Phe Gly Arg Ile Gly Arg Ile
1 5 10 15

Val Phe Arg Ala Ala Gln Lys Arg Ser Asp Ile Glu Ile Val Ala Ile
20 25 30

Asn Asp Leu Leu Asp Ala Asp Tyr Met Ala Tyr Met Leu Lys Tyr Asp
35 40 45

Ser Thr His Gly Arg Phe Asp Gly Thr Val Glu Val Lys Asp Gly His
50 55 60

Leu Ile Val Asn Gly Lys Lys Ile Arg Val Thr Ala Glu Arg Asp Pro
65 70 75 80

Ala Asn Leu Lys Trp Asp Glu Val Gly Val Asp Val Val Ala Glu Ala
85 90 95

Thr Gly Leu Phe Leu Thr Asp Glu Thr Ala Arg Lys His Ile Thr Ala
100 105 110

Gly Ala Lys Lys Val Val Met Thr Gly Pro Ser Lys Asp Asn Thr Pro
115 120 125

Met Phe Val Lys Gly Ala Asn Phe Asp Lys Tyr Ala Gly Gln Asp Ile
130 135 140

```
Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Thr Thr Val
                165                 170                 175

His Ala Thr Thr Ala Thr Gln Lys Thr Val Asp Gly Pro Ser His Lys
            180                 185                 190

Asp Trp Arg Gly Gly Arg Gly Ala Ser Gln Asn Ile Ile Pro Ser Ser
        195                 200                 205

Thr Gly Ala Ala Lys Ala Val Gly Lys Val Leu Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Ala Ala Thr Tyr Glu Gln Ile
                245                 250                 255

Lys Ala Ala Val Lys Ala Ala Ala Glu Gly Glu Met Lys Gly Val Leu
            260                 265                 270

Gly Tyr Thr Glu Asp Asp Val Val Ser Thr Asp Phe Asn Gly Glu Val
        275                 280                 285

Cys Thr Ser Val Phe Asp Ala Lys Ala Gly Ile Ala Leu Asn Asp Asn
    290                 295                 300

Phe Val Lys Leu Val Ser Trp Tyr Asp Asn Glu Thr Gly Tyr Ser Asn
305                 310                 315                 320

Lys Val Leu Asp Leu Ile Ala His Ile Ser Lys
                325                 330


<210> SEQ ID NO 115
<211> LENGTH: 957
<212> TYPE: DNA
<213> ORGANISM: Escherichia coli

<400> SEQUENCE: 115

atgctacaaa attgcgcaca atcaaattgc cgcattattc ctaagaaatt acgcgatatg     60

aaacgtgaag agatttgccg cttgctggcg gataaagtta ataaactgaa aaataaagaa    120

aatagtttgt caggactgtt gcccgatgtg cgtttgttgt atggcgagac gcctttcgca    180

cgtacaccgg tgatgtacga gcctggcatc ataattctct tttccgggca taaaatcggt    240

tatatcaatg aacgcgtgtt tcgttatgat gccaatgaat acctgctgct gacggtgccg    300

ttgccgtttg agtgcgaaac ctatgccacg tcagaggtgc cgctggcagg gttgcgtctc    360

aatgtcgata ttttgcagtt acaggaactg ttgatggaca ttggcgaaga tgagcatttc    420

cagccgtcga tggcagccag cgggattaac tccgccacgt tatcagaaga gattttatgc    480

gcggcggagc ggttactcga cgtgatggag cgaccactgg atgcgcgtat tctcggcaaa    540

cagatcatcc gcgaaattct gtactacgtg ctgaccggac cttgcggcgg cgcgttactg    600

gcgctggtca gtcgccagac tcacttcagt ctgattagcc gcgtgctgaa acggattgag    660

aataaataca ccgaaaacct gagcgtcgag caactggcgg cagaagccaa catgagcgta    720

tcggcgttcc accataattt taagtctgtc accagtacct cgccgttgca gtatttgaag    780

aattaccgtc tgcataaggc gcggatgatg atcatccatg acggcatgaa ggccagcgca    840

gcagcgatgc gcgtcggcta tgaaagcgca tcgcaattta gccgtgagtt taaacgttac    900

ttcggtgtga cgccggggga agatgcggca agaatgcggg cgatgcaggg gaattaa       957


<210> SEQ ID NO 116
<211> LENGTH: 318
```

<212> TYPE: PRT
<213> ORGANISM: Escherichia coli

<400> SEQUENCE: 116

Met Leu Gln Asn Cys Ala Gln Ser Asn Cys Arg Ile Ile Pro Lys Lys
1               5                   10                  15

Leu Arg Asp Met Lys Arg Glu Glu Ile Cys Arg Leu Leu Ala Asp Lys
            20                  25                  30

Val Asn Lys Leu Lys Asn Lys Glu Asn Ser Leu Ser Gly Leu Leu Pro
        35                  40                  45

Asp Val Arg Leu Leu Tyr Gly Glu Thr Pro Phe Ala Arg Thr Pro Val
    50                  55                  60

Met Tyr Glu Pro Gly Ile Ile Ile Leu Phe Ser Gly His Lys Ile Gly
65                  70                  75                  80

Tyr Ile Asn Glu Arg Val Phe Arg Tyr Asp Ala Asn Glu Tyr Leu Leu
                85                  90                  95

Leu Thr Val Pro Leu Pro Phe Glu Cys Glu Thr Tyr Ala Thr Ser Glu
            100                 105                 110

Val Pro Leu Ala Gly Leu Arg Leu Asn Val Asp Ile Leu Gln Leu Gln
        115                 120                 125

Glu Leu Leu Met Asp Ile Gly Glu Asp Glu His Phe Gln Pro Ser Met
    130                 135                 140

Ala Ala Ser Gly Ile Asn Ser Ala Thr Leu Ser Glu Glu Ile Leu Cys
145                 150                 155                 160

Ala Ala Glu Arg Leu Leu Asp Val Met Glu Arg Pro Leu Asp Ala Arg
                165                 170                 175

Ile Leu Gly Lys Gln Ile Ile Arg Glu Ile Leu Tyr Tyr Val Leu Thr
            180                 185                 190

Gly Pro Cys Gly Gly Ala Leu Leu Ala Leu Val Ser Arg Gln Thr His
        195                 200                 205

Phe Ser Leu Ile Ser Arg Val Leu Lys Arg Ile Glu Asn Lys Tyr Thr
    210                 215                 220

Glu Asn Leu Ser Val Glu Gln Leu Ala Ala Glu Ala Asn Met Ser Val
225                 230                 235                 240

Ser Ala Phe His His Asn Phe Lys Ser Val Thr Ser Thr Ser Pro Leu
                245                 250                 255

Gln Tyr Leu Lys Asn Tyr Arg Leu His Lys Ala Arg Met Met Ile Ile
            260                 265                 270

His Asp Gly Met Lys Ala Ser Ala Ala Ala Met Arg Val Gly Tyr Glu
        275                 280                 285

Ser Ala Ser Gln Phe Ser Arg Glu Phe Lys Arg Tyr Phe Gly Val Thr
    290                 295                 300

Pro Gly Glu Asp Ala Ala Arg Met Arg Ala Met Gln Gly Asn
305                 310                 315

<210> SEQ ID NO 117
<211> LENGTH: 1509
<212> TYPE: DNA
<213> ORGANISM: Escherichia coli

<400> SEQUENCE: 117
atgactgaaa aaaaatatat cgttgcgctc gaccagggca ccaccagctc ccgcgcggtc      60
gtaatggatc acgatgccaa tatcattagc gtgtcgcagc gcgaatttga gcaaatctac     120
ccaaaaccag gttgggtaga acacgaccca atggaaatct gggccaccca aagctccacg     180

```
ctggtagaag tgctggcgaa agccgatatc agttccgatc aaattgcagc tatcggtatt    240

acgaaccagc gtgaaaccac tattgtctgg gaaaaagaaa ccggcaagcc tatctataac    300

gccattgtct ggcagtgccg tcgtaccgca gaaatctgcg agcatttaaa acgtgacggt    360

ttagaagatt atatccgcag caataccggt ctggtgattg acccgtactt ttctggcacc    420

aaagtgaagt ggatcctcga ccatgtggaa ggctctcgcg agcgtgcacg tcgtggtgaa    480

ttgctgtttg gtacggttga tacgtggctt atctggaaaa tgactcaggg ccgtgtccat    540

gtgaccgatt acaccaacgc ctctcgtacc atgttgttca acatccatac cctggactgg    600

gacgacaaaa tgctggaagt gctggatatt ccgcgcgaga tgctgccaga agtgcgtcgt    660

tcttccgaag tatacggtca gactaacatt ggcggcaaag gcggcacgcg tattccaatc    720

tccgggatcg ccggtgacca gcaggccgcg ctgtttggtc agttgtgcgt gaaagaaggg    780

atggcgaaga acacctatgg cactggctgc tttatgctga tgaacactgg cgagaaagcg    840

gtgaaatcag aaaacggcct gctgaccacc atcgcctgcg gcccgactgg cgaagtgaac    900

tatgcgttgg aaggtgcggt gtttatggca ggcgcatcca ttcagtggct gcgcgatgaa    960

atgaagttga ttaacgacgc ctacgattcc gaatatttcg ccaccaaagt gcaaaacacc   1020

aatggtgtgt atgtggttcc ggcatttacc gggctgggtg cgccgtactg ggacccgtat   1080

gcgcgcgggg cgattttcgg tctgactcgt ggggtgaacg ctaaccacat tatacgcgcg   1140

acgctggagt ctattgctta tcagacgcgt gacgtgctgg aagcgatgca ggccgactct   1200

ggtatccgtc tgcacgccct gcgcgtggat ggtggcgcag tagcaaacaa tttcctgatg   1260

cagttccagt ccgatattct cggcacccgc gttgagcgcc cggaagtgcg cgaagtcacc   1320

gcattgggtg cggcctatct cgcaggcctg gcggttggct tctggcagaa cctcgacgag   1380

ctgcaagaga aagcggtgat tgagcgcgag ttccgtccag gcatcgaaac cactgagcgt   1440

aattaccgtt acgcaggctg gaaaaaagcg gttaaacgcg cgatggcgtg ggaagaacac   1500

gacgaataa                                                           1509
```

```
<210> SEQ ID NO 118
<211> LENGTH: 502
<212> TYPE: PRT
<213> ORGANISM: Escherichia coli

<400> SEQUENCE: 118

Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Ile Ser Val Ser
            20                  25                  30

Gln Arg Glu Phe Glu Gln Ile Tyr Pro Lys Pro Gly Trp Val Glu His
        35                  40                  45

Asp Pro Met Glu Ile Trp Ala Thr Gln Ser Ser Thr Leu Val Glu Val
    50                  55                  60

Leu Ala Lys Ala Asp Ile Ser Ser Asp Gln Ile Ala Ala Ile Gly Ile
65                  70                  75                  80

Thr Asn Gln Arg Glu Thr Thr Ile Val Trp Glu Lys Glu Thr Gly Lys
                85                  90                  95

Pro Ile Tyr Asn Ala Ile Val Trp Gln Cys Arg Arg Thr Ala Glu Ile
            100                 105                 110

Cys Glu His Leu Lys Arg Asp Gly Leu Glu Asp Tyr Ile Arg Ser Asn
        115                 120                 125

Thr Gly Leu Val Ile Asp Pro Tyr Phe Ser Gly Thr Lys Val Lys Trp
```

```
    130                 135                 140

Ile Leu Asp His Val Glu Gly Ser Arg Glu Arg Ala Arg Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Thr Leu Asp Trp Asp Asp Lys Met Leu Glu Val Leu
        195                 200                 205

Asp Ile Pro Arg Glu Met Leu Pro Glu Val Arg Arg Ser Ser Glu Val
    210                 215                 220

Tyr Gly Gln Thr Asn Ile Gly Gly Lys Gly Gly Thr Arg Ile Pro Ile
225                 230                 235                 240

Ser Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Thr Gly Glu Val Asn Tyr Ala Leu Glu
    290                 295                 300

Gly Ala Val Phe Met Ala Gly Ala Ser Ile Gln Trp Leu Arg Asp Glu
305                 310                 315                 320

Met Lys Leu Ile Asn Asp Ala Tyr Asp Ser Glu Tyr Phe Ala Thr Lys
                325                 330                 335

Val Gln Asn Thr Asn Gly Val Tyr Val Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ala Asn His Ile Ile Arg Ala Thr Leu Glu Ser
    370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

Arg Pro Glu Val Arg Glu Val Thr Ala Leu Gly Ala Ala Tyr Leu Ala
        435                 440                 445

Gly Leu Ala Val Gly Phe Trp Gln Asn Leu Asp Glu Leu Gln Glu Lys
    450                 455                 460

Ala Val Ile Glu Arg Glu Phe Arg Pro Gly Ile Glu Thr Thr Glu Arg
465                 470                 475                 480

Asn Tyr Arg Tyr Ala Gly Trp Lys Lys Ala Val Lys Arg Ala Met Ala
                485                 490                 495

Trp Glu Glu His Asp Glu
            500
```

<210> SEQ ID NO 119
<211> LENGTH: 258
<212> TYPE: DNA
<213> ORGANISM: Escherichia coli

<400> SEQUENCE: 119
atgttccagc aagaagttac cattaccgct ccgaacggtc tgcacacccg ccctgctgcc 60
cagtttgtaa aagaagctaa gggcttcact tctgaaatta ctgtgacttc caacggcaaa 120
agcgccagcg cgaaaagcct gtttaaactg cagactctgg gcctgactca aggtaccgtt 180
gtgactatct ccgcagaagg cgaagacgag cagaaagcgg ttgaacatct ggttaaactg 240
atggcggaac tcgagtaa 258

<210> SEQ ID NO 120
<211> LENGTH: 85
<212> TYPE: PRT
<213> ORGANISM: Escherichia coli

<400> SEQUENCE: 120

Met Phe Gln Gln Glu Val Thr Ile Thr Ala Pro Asn Gly Leu His Thr
1 5 10 15

Arg Pro Ala Ala Gln Phe Val Lys Glu Ala Lys Gly Phe Thr Ser Glu
20 25 30

Ile Thr Val Thr Ser Asn Gly Lys Ser Ala Ser Ala Lys Ser Leu Phe
35 40 45

Lys Leu Gln Thr Leu Gly Leu Thr Gln Gly Thr Val Val Thr Ile Ser
50 55 60

Ala Glu Gly Glu Asp Glu Gln Lys Ala Val Glu His Leu Val Lys Leu
65 70 75 80

Met Ala Glu Leu Glu
85

<210> SEQ ID NO 121
<211> LENGTH: 1728
<212> TYPE: DNA
<213> ORGANISM: Escherichia coli

<400> SEQUENCE: 121
atgatttcag gcattttagc atccccgggt atcgctttcg gtaaagctct gcttctgaaa 60
gaagacgaaa ttgtcattga ccggaaaaaa atttctgccg accaggttga tcaggaagtt 120
gaacgttttc tgagcggtcg tgccaaggca tcagcccagc tggaaacgat caaaacgaaa 180
gctggtgaaa cgttcggtga agaaaaagaa gccatctttg aagggcatat tatgctgctc 240
gaagatgagg agctggagca ggaaatcata gccctgatta aagataagca catgacagct 300
gacgcagctg ctcatgaagt tatcgaaggt caggcttctg ccctggaaga gctggatgat 360
gaatacctga aagaacgtgc ggctgacgta cgtgatatcg gtaagcgcct gctgcgcaac 420
atcctgggcc tgaagattat cgacctgagc gccattcagg atgaagtcat tctggttgcc 480
gctgacctga cgccgtccga aaccgcacag ctgaacctga agaaggtgct gggtttcatc 540
accgacgcgg gtggccgtac ttcccacacc tctatcatgg cgcgttctct ggaactacct 600
gctatcgtgg gtaccggtag cgtcacctct caggtgaaaa atgacgacta tctgattctg 660
gatgccgtaa ataatcaggt ttacgtcaat ccaaccaacg aagttattga taaaatgcgc 720
gctgttcagg agcaagtggc ttctgaaaaa gcagagcttg ctaaactgaa agatctgcca 780
gctattacgc tggacggtca ccaggtagaa gtatgcgcta acattggtac ggttcgtgac 840
gttgaaggtg cagagcgtaa cggcgctgaa ggcgttggtc tgtatcgtac tgagttcctg 900
ttcatggacc gcgacgcact gcccactgaa gaagaacagt ttgctgctta caaagcagtg 960
gctgaagcgt gtggctcgca agcggttatc gttcgtacca tggacatcgg cggcgacaaa 1020
gagctgccat acatgaactt cccgaaagaa gagaacccgt tcctcggctg gcgcgctatc 1080

```
cgtatcgcga tggatcgtag agagatcctg cgcgatcagc tccgcgctat cctgcgtgcc   1140

tcggctttcg gtaaattgcg cattatgttc ccgatgatca tctctgttga agaagtgcgt   1200

gcactgcgca aagagatcga aatctacaaa caggaactgc gcgacgaagg taaagcgttt   1260

gacgagtcaa ttgaaatcgg cgtaatggtg gaaacaccgg ctgccgcaac aattgcacgt   1320

catttagcca aagaagttga tttctttagt atcggcacca atgatttaac gcagtacact   1380

ctggcagttg accgtggtaa tgatatgatt tcacaccttt accagccaat gtcaccgtcc   1440

gtgctgaact tgatcaagca agttattgat gcttctcatg ctgaaggcaa atggactggc   1500

atgtgtggtg agcttgctgg cgatgaacgt gctacacttc tgttgctggg gatgggtctg   1560

gacgaattct ctatgagcgc catttctatc ccgcgcatta agaagattat ccgtaacacg   1620

aacttcgaag atgcgaaggt gttagcagag caggctcttg ctcaaccgac aacggacgag   1680

ttaatgacgc tggttaacaa gttcattgaa gaaaaaacaa tctgctaa                1728
```

```
<210> SEQ ID NO 122
<211> LENGTH: 575
<212> TYPE: PRT
<213> ORGANISM: Escherichia coli

<400> SEQUENCE: 122

Met Ile Ser Gly Ile Leu Ala Ser Pro Gly Ile Ala Phe Gly Lys Ala
1               5                   10                  15

Leu Leu Leu Lys Glu Asp Glu Ile Val Ile Asp Arg Lys Lys Ile Ser
            20                  25                  30

Ala Asp Gln Val Asp Gln Glu Val Glu Arg Phe Leu Ser Gly Arg Ala
        35                  40                  45

Lys Ala Ser Ala Gln Leu Glu Thr Ile Lys Thr Lys Ala Gly Glu Thr
    50                  55                  60

Phe Gly Glu Glu Lys Glu Ala Ile Phe Glu Gly His Ile Met Leu Leu
65                  70                  75                  80

Glu Asp Glu Glu Leu Glu Gln Glu Ile Ile Ala Leu Ile Lys Asp Lys
                85                  90                  95

His Met Thr Ala Asp Ala Ala Ala His Glu Val Ile Glu Gly Gln Ala
            100                 105                 110

Ser Ala Leu Glu Glu Leu Asp Asp Glu Tyr Leu Lys Glu Arg Ala Ala
        115                 120                 125

Asp Val Arg Asp Ile Gly Lys Arg Leu Leu Arg Asn Ile Leu Gly Leu
    130                 135                 140

Lys Ile Ile Asp Leu Ser Ala Ile Gln Asp Glu Val Ile Leu Val Ala
145                 150                 155                 160

Ala Asp Leu Thr Pro Ser Glu Thr Ala Gln Leu Asn Leu Lys Lys Val
                165                 170                 175

Leu Gly Phe Ile Thr Asp Ala Gly Gly Arg Thr Ser His Thr Ser Ile
            180                 185                 190

Met Ala Arg Ser Leu Glu Leu Pro Ala Ile Val Gly Thr Gly Ser Val
        195                 200                 205

Thr Ser Gln Val Lys Asn Asp Asp Tyr Leu Ile Leu Asp Ala Val Asn
    210                 215                 220

Asn Gln Val Tyr Val Asn Pro Thr Asn Glu Val Ile Asp Lys Met Arg
225                 230                 235                 240

Ala Val Gln Glu Gln Val Ala Ser Glu Lys Ala Glu Leu Ala Lys Leu
                245                 250                 255
```

-continued

```
Lys Asp Leu Pro Ala Ile Thr Leu Asp Gly His Gln Val Glu Val Cys
            260                 265                 270

Ala Asn Ile Gly Thr Val Arg Asp Val Glu Gly Ala Glu Arg Asn Gly
        275                 280                 285

Ala Glu Gly Val Gly Leu Tyr Arg Thr Glu Phe Leu Phe Met Asp Arg
    290                 295                 300

Asp Ala Leu Pro Thr Glu Glu Glu Gln Phe Ala Ala Tyr Lys Ala Val
305                 310                 315                 320

Ala Glu Ala Cys Gly Ser Gln Ala Val Ile Val Arg Thr Met Asp Ile
                325                 330                 335

Gly Gly Asp Lys Glu Leu Pro Tyr Met Asn Phe Pro Lys Glu Glu Asn
            340                 345                 350

Pro Phe Leu Gly Trp Arg Ala Ile Arg Ile Ala Met Asp Arg Arg Glu
        355                 360                 365

Ile Leu Arg Asp Gln Leu Arg Ala Ile Leu Arg Ala Ser Ala Phe Gly
    370                 375                 380

Lys Leu Arg Ile Met Phe Pro Met Ile Ile Ser Val Glu Glu Val Arg
385                 390                 395                 400

Ala Leu Arg Lys Glu Ile Glu Ile Tyr Lys Gln Glu Leu Arg Asp Glu
                405                 410                 415

Gly Lys Ala Phe Asp Glu Ser Ile Glu Ile Gly Val Met Val Glu Thr
            420                 425                 430

Pro Ala Ala Ala Thr Ile Ala Arg His Leu Ala Lys Glu Val Asp Phe
        435                 440                 445

Phe Ser Ile Gly Thr Asn Asp Leu Thr Gln Tyr Thr Leu Ala Val Asp
    450                 455                 460

Arg Gly Asn Asp Met Ile Ser His Leu Tyr Gln Pro Met Ser Pro Ser
465                 470                 475                 480

Val Leu Asn Leu Ile Lys Gln Val Ile Asp Ala Ser His Ala Glu Gly
                485                 490                 495

Lys Trp Thr Gly Met Cys Gly Glu Leu Ala Gly Asp Glu Arg Ala Thr
            500                 505                 510

Leu Leu Leu Leu Gly Met Gly Leu Asp Glu Phe Ser Met Ser Ala Ile
        515                 520                 525

Ser Ile Pro Arg Ile Lys Lys Ile Ile Arg Asn Thr Asn Phe Glu Asp
    530                 535                 540

Ala Lys Val Leu Ala Glu Gln Ala Leu Ala Gln Pro Thr Thr Asp Glu
545                 550                 555                 560

Leu Met Thr Leu Val Asn Lys Phe Ile Glu Glu Lys Thr Ile Cys
                565                 570                 575
```

<210> SEQ ID NO 123
<211> LENGTH: 510
<212> TYPE: DNA
<213> ORGANISM: Escherichia coli

<400> SEQUENCE: 123

```
atgggtttgt tcgataaact gaaatctctg gtttccgacg acaagaagga taccggaact      60

attgagatca ttgctccgct ctctggcgag atcgtcaata tcgaagacgt gccggatgtc     120

gtttttgcgg aaaaaatcgt tggtgatggt attgctatca aaccaacggg taacaaaatg     180

gtcgcgccag tagacggcac cattggtaaa atctttgaaa ccaaccacgc attctctatc     240

gaatctgata gcggcgttga actgttcgtc cacttcggta tcgacaccgt tgaactgaaa     300

ggcgaaggct tcaagcgtat tgctgaagaa ggtcagcgcg tgaaagttgg cgatactgtc     360
```

```
attgaatttg atctgccgct gctggaagag aaagccaagt ctaccctgac tccggttgtt    420

atctccaaca tggacgaaat caaagaactg atcaaactgt ccggtagcgt aaccgtgggt    480

gaaaccccgg ttatccgcat caagaagtaa                                     510


<210> SEQ ID NO 124
<211> LENGTH: 169
<212> TYPE: PRT
<213> ORGANISM: Escherichia coli

<400> SEQUENCE: 124

Met Gly Leu Phe Asp Lys Leu Lys Ser Leu Val Ser Asp Asp Lys Lys
1               5                   10                  15

Asp Thr Gly Thr Ile Glu Ile Ile Ala Pro Leu Ser Gly Glu Ile Val
            20                  25                  30

Asn Ile Glu Asp Val Pro Asp Val Val Phe Ala Glu Lys Ile Val Gly
        35                  40                  45

Asp Gly Ile Ala Ile Lys Pro Thr Gly Asn Lys Met Val Ala Pro Val
    50                  55                  60

Asp Gly Thr Ile Gly Lys Ile Phe Glu Thr Asn His Ala Phe Ser Ile
65                  70                  75                  80

Glu Ser Asp Ser Gly Val Glu Leu Phe Val His Phe Gly Ile Asp Thr
                85                  90                  95

Val Glu Leu Lys Gly Glu Gly Phe Lys Arg Ile Ala Glu Glu Gly Gln
            100                 105                 110

Arg Val Lys Val Gly Asp Thr Val Ile Glu Phe Asp Leu Pro Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Ile Lys Leu Ser Gly Ser Val Thr Val Gly
145                 150                 155                 160

Glu Thr Pro Val Ile Arg Ile Lys Lys
                165


<210> SEQ ID NO 125
<211> LENGTH: 101
<212> TYPE: DNA
<213> ORGANISM: artificial
<220> FEATURE:
<223> OTHER INFORMATION: oligo DgldA

<400> SEQUENCE: 125

atggaccgca ttattcaatc accgggtaaa tacatccagg gcgctgatgt gattaatcgt     60

ctgggcgaat acctgaagcc gtgtaggctg gagctgcttc g                        101


<210> SEQ ID NO 126
<211> LENGTH: 100
<212> TYPE: DNA
<213> ORGANISM: artificial
<220> FEATURE:
<223> OTHER INFORMATION: oligo DgldA

<400> SEQUENCE: 126

ttattcccac tcttgcagga aacgctgacc gtactggtcg gctaccagca gagcggcgta     60

aacctgatct ggcgtcgcgc catatgaata tcctccttag                          100


<210> SEQ ID NO 127
<211> LENGTH: 98
```

<212> TYPE: DNA
<213> ORGANISM: artificial
<220> FEATURE:
<223> OTHER INFORMATION: oligo DptsHIcrr souche 3

<400> SEQUENCE: 127
ggggaaatac aatgttccag caagaagtta ccattaccgc tccgaacggt ctgcacaccc 60
gccctgctgc ccagtttgca tatgaatatc ctccttag 98

<210> SEQ ID NO 128
<211> LENGTH: 100
<212> TYPE: DNA
<213> ORGANISM: artificial
<220> FEATURE:
<223> OTHER INFORMATION: oligo DptsHIcrr souche 3

<400> SEQUENCE: 128
gcggcaagaa ttacttcttg atgcggataa ccggggtttc acccacggtt acgctaccgg 60
acagtttgat cagttctttg tgtaggctgg agctgcttcg 100

<210> SEQ ID NO 129
<211> LENGTH: 100
<212> TYPE: DNA
<213> ORGANISM: artificial
<220> FEATURE:
<223> OTHER INFORMATION: oligo ptsHIcrr souche 7

<400> SEQUENCE: 129
ccgtgggtga aaccccggtt atccgcatca agaagtaatt cttgccgcag tgaaaaatgg 60
cgcccatcgg cgccattttt catatgaata tcctccttag 100

<210> SEQ ID NO 130
<211> LENGTH: 99
<212> TYPE: DNA
<213> ORGANISM: artificial
<220> FEATURE:
<223> OTHER INFORMATION: oligo ptsHIcrr souche 7

<400> SEQUENCE: 130
gcgcgtactg gaagtgatgc gctacaccca gcagcatgag agcgatgaat tgattttgcc 60
gccgctggcg gaagcataat gtaggctgga gctgcttcg 99

<210> SEQ ID NO 131
<211> LENGTH: 100
<212> TYPE: DNA
<213> ORGANISM: artificial
<220> FEATURE:
<223> OTHER INFORMATION: oligo DppsR

<400> SEQUENCE: 131
cgttctacgc ttctgtgcgt ttttaattta tgctttcata gaattatgtc tgcatcacgg 60
gaagaacaaa atgattccgg ggatccgtcg acctgcagtt 100

-continued

```
<210> SEQ ID NO 132
<211> LENGTH: 100
<212> TYPE: DNA
<213> ORGANISM: artificial
<220> FEATURE:
<223> OTHER INFORMATION: oligo DppsR

<400> SEQUENCE: 132

gtcacacctc gccgggtggt tagcatgata acaaaaaaat aagctaatgc actagttctc     60

tagtacattc ggcgactaag tgtaggctgg agctgcttcg                          100
```

METHOD FOR THE FERMENTATIVE PRODUCTION OF MOLECULES OF INTEREST BY MICROORGANISMS COMPRISING GENES CODING SUGAR PHOSPHOTRANSFERASE SYSTEM (PTS)

FIELD OF THE INVENTION

The present invention relates to a new method for the production of a molecule of interest by conversion of a source of carbon in a fermentative process comprising culturing a microorganism genetically modified for the production of said molecule of interest, wherein said microorganism comprises functional genes coding PTS carbohydrate utilization system and wherein the expression of proteins regulating the expression of phosphoenolpyruvate synthase (PPS) is down-regulated. The present invention also relates to the genetically modified microorganism used in the method of the invention.

BACKGROUND

In bacteria, external carbohydrate (sugar) is transported into the cell and phosphorylated by the phosphoenolpyruvate: sugar phosphotransferase system (PTS). Phosphoenolpyruvate (PEP) is a critical molecule of central metabolism. In many microorganisms, carbohydrates supporting growth are taken up and simultaneously phosphorylated by PTS consuming one molecule of PEP per molecule of carbohydrate (Postma a Roseman 1976). The PTS is made of two cytoplasmic proteins, Enzyme I (EI) and HPr, and a variable number of membrane protein complexes specific to the carbohydrate to be taken up (Enzymes II, EII). All together, these EI, HPr and EII proteins act as a phosphoryl transfer chain between PEP and the carbohydrate, which is phosphorylated as it crosses the cell membrane:

EI+PEP ⇨ EI-P+Pyruvate

EI-P+Hpr ⇨ Hpr-P+EI

Hpr-P+EII ⇨ EII-P+Hpr

EII-P+Carbohydrate (outside) ⇨ Carbohydrate-P (inside)+EII

In addition to its role as a phosphate donor for the PTS, PEP also participates in the last step of glycolysis generating pyruvate through the pyruvate kinase enzymes (Kornberg & Malcovati 1973):

PEP+ADP ⇨ Pyruvate+ATP

Furthermore, PEP connects glycolysis and the citric acid cycle via an anaplerotic reaction generating oxaloacetate, catalysed by the PEP carboxylase enzyme (Canovas & Kornberg 1965):

PEP+HCO3- ⇨ Oxaloacetate+Pi

PEP is also a precursor of aromatic amino acids, quinones and C1 metabolites, through the chorismate pathway (Pittard a Wallace 1966):

2 PEP+Erythrose-4-phosphate+ATP+$NAD(P)^+$ ⇨ Chorismate+4 Pi+ADP+NAD(P)H+$H^+$

Several research groups have developed strategies to increase the availability of PEP in order to enhance the production and yield of desired products: inactivation of the PTS and/or the pyruvate kinase enzymes (Gosset et al. 1996, Meza et al. 2012), inactivation of the global regulator CsrA (Tatarko a Romeo 2001), overexpression of the gluconeogenic enzymes PEP carboxykinase (Kim et al. 2004) or PEP synthase (Patnaik et al. 1992).

The enzyme PEP synthase (PPS, EC 2.7.9.2) catalyzes the phosphorylation of pyruvate to PEP with the hydrolysis of ATP to AMP (Cooper & Kornberg, 1965):

Pyruvate+ATP+$H_2O$ ⇨ PEP+AMP+Pi

In many microorganisms, PPS is regulated by a phosphorylation/dephosphorylation mechanism mediated by the PPS regulatory protein (PRPP) belonging to the DUF299 family (Burnell, 2010).

The aim of the study of Burnell is to characterize the structure and the function of protein DUF299 and the gene encoding said protein. However, this article does not suggest the possibility to regulate the expression of this protein in order to obtain a specific effect such as increasing the production of molecules of interest.

SUMMARY OF INVENTION

The Applicant has found surprisingly that the inactivation of the expression of proteins regulating PPS expression allows the production of molecules of interest which are usually produced by fermentation process in microorganisms to be increased.

The finding of the inventors is advantageous since it allows a number of drawbacks of other prior art methods known for increasing the production of metabolic products, such as suggested in patent application WO2004033471, to be overcome.

Indeed, in order to increase the production of molecules of interest, it is often necessary to improve the carbon source uptake in the producer microorganism by performing several genetic modifications. However, genes involved in carbon sources uptake and more particularly in carbohydrates import are engaged in complex system of regulation (Gabor et al, 2011; Kotrba et al, 2001). Thus, such genetic modifications lead to unpredictable consequences and strains obtained could be unstable. Moreover, these methods have a high cost.

Consequently, there is a need to provide new methods allowing producing molecules of interest at low cost using stable microorganism strains.

According to the present invention, it is possible to increase the production of desired products by inactivating the PPS regulatory protein (PRPP) only.

With respect to a first aspect, the present invention thus relates to a method for the production of a molecule of interest by conversion of a source of carbon in a fermentative process comprising the following steps:

- culturing a genetically modified microorganism for the production of the molecule of interest in an appropriate culture medium comprising a carbohydrate as a source of carbon; and
- recovering the molecule of interest from the culture medium,
  - wherein said genetically modified microorganism comprises functional genes coding for a PTS carbohydrate utilization system and
  - wherein in said genetically modified microorganism the expression of the bifunctional ADP-dependent kinase-Pi-dependent pyrophosphorylase protein regulating the expression of the phosphoenolpyruvate synthase (PPS) is decreased.

The microorganism used in the method of the invention has specific characteristics, such as having a functional gene coding for a PTS carbohydrate utilization system and a decreased expression of the bifunctional ADP-dependent kinase-Pi-dependent pyrophosphorylase protein regulating the expression of the PPS. This microorganism can be considered as being specific and surprising since it was not obvious to obtain a genetically modified microorganism wherein the expression of phosphoenolpyruvate synthase (PPS) is affected without affecting the functionality of the whole cascade of carbohydrates uptake.

With respect to a second aspect, the present invention thus relates to a genetically modified microorganism for the enhanced production of a molecule of interest from a carbohydrate as a source of carbon, wherein said genetically modified microorganism comprises functional genes coding for a PTS carbohydrate utilization system and a decreased expression of the bifunctional ADP-dependent kinase-Pi-dependent pyrophosphorylase protein regulating the expression of the PPS.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention.

Furthermore, the practice of the present invention employs, unless otherwise indicated, conventional microbiological and molecular biology techniques within the skill of the art. Such techniques are well-known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, a reference to "an enzyme" is a reference to one or more enzymes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

As used herein, the following terms may be used for interpretation of the claims and specification.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins) are obtained by comparing protein sequences from 66 fully sequenced genomes representing 38 major phylogenetic lines. Each COG is defined from at least three lines, which permits the identification of former conserved domains.

The means of identifying homologous sequences and their percent homologies are well-known to those skilled in the art, and include, in particular, the BLAST programs (Altschul et al, 1990). The sequences obtained can then be exploited (e.g., aligned) using, for example, the programs CLUSTALW or MULTALIN.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (2001).

As described above, the method of the present invention allows the production of a molecule of interest by conversion of a source of carbon in a fermentative process including the steps of:

- culturing a genetically modified microorganism for the production of the molecule of interest in an appropriate culture medium comprising a carbohydrate as source of carbon and
- recovering the molecule of interest from the culture medium,
  - said genetically modified microorganism comprising functional genes coding for a PTS carbohydrate utilization system and a decreased expression of the bifunctional ADP-dependent kinase-Pi-dependent pyrophosphorylase protein regulating the expression of the phosphoenolpyruvate synthase (PPS).

The terms "fermentative process," "fermentation," or "culture" are used herein interchangeably to denote the growth of a microorganism. The fermentation is generally conducted in fermenters with an inorganic culture medium of a known, defined composition adapted to the microorganism being used, containing at least one simple carbon source, and if necessary a co-substrate necessary for the production of the metabolite. In particular, the inorganic culture medium for *E. coli* can be of identical or similar composition to an M9 medium (Anderson, 1946), an M63 medium (Miller, 1992) or a medium such as defined by Schaefer et al. (1999).

In the context of the present invention, by "fermentative conversion," it is meant that the conversion of the carbon source into the molecule of interest occurs when the microorganism is cultured under appropriate fermentation conditions.

A "culture medium" means herein a medium (e.g., a sterile, liquid media) comprising nutrients essential or beneficial to the maintenance and/or growth of the microorganism such as carbon sources or carbon substrates; nitrogen sources, for example peptone, yeast extracts, meat extracts, malt extracts, urea, ammonium sulfate, ammonium chloride, ammonium nitrate and ammonium phosphate; phosphorus sources, for example monopotassium phosphate or dipotassium phosphate; trace elements (e.g., metal salts) for example magnesium salts, cobalt salts and/or manganese salts; as well as growth factors such as amino acids and vitamins.

The term "source of carbon," "carbon source," or "carbon substrate" according to the present invention refers to any molecule that a microorganism is capable of metabolizing and which contains at least one carbon atom. Examples of preferred carbon sources according to the invention include, without limitation, carbohydrates.

In a preferred embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass pre-treated or not, is a particularly preferred renewable carbon source.

The term "carbohydrate" refers herein to any carbon source capable of being metabolized by a microorganism and containing at least one carbon atom, two atoms of hydrogen and one atom of oxygen. The carbohydrate of the invention is preferably selected from glucose, fructose, sucrose, mannose, chitobiose, cellobiose, trehalose, galactitol, mannitol, sorbitol, galactosamine, N-acetyl-D-galactosamine, N-acetylglucosamine, N-acetylmuramic acid, lactose, galactose, sorbose, maltose, N,N'-diacetylchitobiose, ascorbate, β-glucoside. In a more preferred embodiment of the invention, the source of carbon is selected from glucose, fructose, mannose, cellobiose, sucrose, and any combination thereof.

The person skilled in the art can easily determine the culture conditions necessary for growing the microorganisms in the method according to the invention. In particular, it is well-known that bacteria can be fermented at a temperature comprised between 20° C. and 55° C., preferentially between 25° C. and 40° C. *E. coli* can more particularly be cultured at a temperature comprised between about 30° C. and about 37° C.

This culturing process can be performed either in a batch process, in a fed-batch process or in a continuous process, and under aerobic, micro-aerobic or anaerobic conditions.

According to a particular embodiment of the method of the invention, the functional genes coding for a PTS carbohydrate utilization system are heterologous (recombinant microorganism) or native to the genetically modified microorganism (wild-type microorganism).

By "gene", it is meant herein a nucleic acid molecule or polynucleotide that codes for a particular protein (i.e. polypeptide), or in certain cases, for a functional or structural RNA molecule. In the context of the present invention, the genes referred to herein encode proteins, such as enzymes, efflux systems or uptake transporters. Genes according to the invention are either endogenous genes or exogenous genes.

The term "recombinant microorganism" or "genetically modified microorganism" as used herein, refers to a bacterium, yeast, or a fungus that is not found in nature and is genetically different from equivalent microorganisms found in nature. According to the invention, the term "modifications" designate any genetic change introduced or induced in the microorganism. The microorganism may be modified through either the introduction of new genetic elements, the increase or the attenuation of the expression of endogenous or exogenous genes or the deletion of endogenous genetic elements. Further, a microorganism may be modified by forcing the development and evolution of new metabolic pathways by combining directed mutagenesis and evolution under specific selection pressure (see, for example, WO 2004076659).

In the context of the present invention, the term "exogenous gene" (or alternatively, "heterologous gene" or "transgene") refers to a gene not naturally occurring in the microorganism. It may be artificial or it may originate from another microorganism.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described in Graf et al. (2000), Deml et al. (2001) or Davis & Olsen (2011). Several softwares have been developed for codon optimization determination such as the GeneOptimizer® software (Lifetechnologies) or the OptimumGene™ software (GenScript). In other words, the exogenous gene encoding a protein of interest is preferably codon-optimized for expression in a specific microorganism.

According to another embodiment of the method of the present invention, the genetically modified microorganism comprises a native gene coding for the bifunctional ADP-dependent kinase-Pi-dependent pyrophosphorylase protein regulating the expression of the phosphoenolpyruvate synthase (PPS) whose expression is attenuated or deleted. In other worlds, in said genetically modified microorganism, expression of the native gene coding for the bifunctional ADP-dependent kinase-Pi-dependent pyrophosphorylase protein is attenuated or deleted compared to the microorganism unmodified. Preferably in the microorganism of the invention, the native gene coding for the bifunctional ADP-dependent kinase-Pi-dependent pyrophosphorylase protein is deleted.

By "native gene" or "endogenous gene" it is meant herein that said gene is naturally present in the microorganism.

In the context of the present invention, should the microorganism be genetically modified to "modulate" the expression level of one or more endogenous genes, it is meant herein that the expression level of said gene is up-regulated, downregulated (i.e. attenuated), or even completely abolished by comparison to its natural expression level. Such modulation can therefore theoretically result in an enhancement of the activity of the gene product, or alternatively, in a lower or null activity of the endogenous gene product.

Endogenous gene activity and/or expression level can also be modified by introducing mutations into their coding sequence to modify the gene product. A deletion of an endogenous gene can also be performed to totally inhibit its expression within the microorganism. Another way to modulate the expression of an endogenous gene is to exchange its promoter (i.e. wild type promoter) with a stronger or weaker promoter to up- or down-regulate the expression level of this gene. Promoters suitable for such a purpose can be homologous or heterologous and are well-known in the art. It is within the skill of the person in the art to select appropriate promoters for modulating the expression of an endogenous gene.

According to another embodiment of the present invention, the microorganism is selected from microorganisms expressing a functional PTS sugar system. Preferentially, the microorganism is selected from the group comprising Enterobacteriaceae, Clostridiaceae, Bacillaceae, Streptomycetaceae, Deinococcaceae, Nitrosomonadaceae, Vibrionaceae, Pseudomonadaceae, Corynebacteriaceae, Saccharomyceteceae and yeasts. More preferentially, the microorganism is a species of *Citrobacter, Corynebacterium, Deinococcus, Escherichia, Pantoea, Klebsiella, Nitrosomonas, Photorhabdus, Photobacterium, Pseudomonas, Salmonella, Serratia, Shigella* and *Yersinia*. Even more preferentially, the microorganism is selected from *Escherichia coli, Klebsiella pneumoniae, Klebisella oxytoca, Pseudomonas aeruginosa, Pseudomonas fluorescens, Salmonalla typhimurium, Salmonella enterica, Serratia marcescens, Pantoea ananatis, Corynebacterium glutamicum, Deinococcus radiodurans, Thermoanaerobacterium thermosaccharolyticum, Clostridium sphenoides*, and *Saccharomyces cerevisiae.*

In particular, the examples show modified *E. coli* strains, but these modifications can easily be performed on other microorganisms of the same family.

*E. coli* belongs to the Enterobacteriaceae family which comprises members that are gram-negative, rod-shaped, non-spore forming and are typically 1-5 μm in length. Most members use flagella to move about, but a few genera are non-motile. Many members of this family are a normal part of the gut flora found in the intestines of humans and other animals, while others are found in water or soil, or are parasites of a variety of different animals and plants. *E. coli* is one of the most important model organisms, but other important members of the Enterobacteriaceae family include *Klebsiella*, in particular *Klebsiella pneumoniae*, and *Salmonella.*

According to another embodiment of the method of the present invention, the gene ppsR of SEQ ID NO:1 coding for the bifunctional ADP-dependent kinase-Pi-dependent pyrophosphorylase DUF299 protein of SEQ ID NO:2 is deleted (which can be referred to as "ΔppsR").

The term "deleted", as used herein, refers to the complete suppression of the expression of a gene. This suppression of expression can be either an inhibition of the expression of the gene, a deletion of all or part of the promoter region necessary for expression of the gene, or a deletion in the coding region of the gene. The deleted gene can be replaced by a selection marker gene that facilitates the identification, isolation and purification of the strains according to the invention. For example, suppression of gene expression may be achieved by the technique of homologous recombination (Datsenko & Wanner, 2000).

In another embodiment, the gene ppsR coding for the bifunctional ADP-dependent kinase-Pi-dependent pyrophosphorylase DUF299 protein may be attenuated.

The term "attenuated", as used herein, refers to the partial suppression of the expression of a gene. This attenuation of expression can be either the exchange of the wild-type promoter for a weaker natural or synthetic promoter or the use of an agent reducing ppsR gene expression, including antisense RNA or interfering RNA (iRNA), and more particularly small interfering RNAs (siRNAs) or short hairpin RNAS (shRNAs). For example, promoter exchange may be achieved by the technique of homologous recombination (Datsenko & Wanner, 2000).

Any other methods known to those skilled in the art suitable for the inhibition of the expression or the function of a protein, and especially of this protein, may be used.

The method of the present invention may be used for producing various molecules of interest in high quantity. Thus, the method of the invention allows the production of molecules selected from alcohols, hydrocarbons, carboxylic acids, biofuels, solvents and amino acids to be increased.

Particularly, the method of the invention allows the production of molecules of interest selected from ethanol, ethylene, ethylene glycol, glycolic acid, propylene, acrylic acid, isopropanol, lactic acid, 1,3-propanediol, 1,2-propanediol, prenol, isobutene, butadiene, butanediol, butanol, isobutanol, methyl ethyl ketone, succinic acid, glutamic acid, isoprene, adipic acid, muconic acid, lysine, dodecanedioic acid, farnesene, and 2,4-dihydroxybutyric acid to be increased.

More particularly, the method of the invention allows the production of molecules of interest selected from glycolic acid, 1,2-propanediol, and 1,3-propanediol to be improved.

The term 'improving 1,2-propanediol production' refers to an increased productivity of 1,2-propanediol and/or an increased titer of 1,2-propanediol and/or an increased 1,2-propanediol/carbon source yield and/or an increased purity of 1,2-propanediol in comparison to the microorganism prior to the deletion or the attenuation of ppsR gene. The production of 1,2-propanediol by the microorganism in the culture broth can be recorded unambiguously by standard analytical means known by those skilled in the art and in particular with HPLC. Some examples of genetically modified microorganisms with increased 1,2-propanediol production are disclosed in the WO2015173247 and WO2012172050 patent applications, the U.S. Pat. No. 6,087,140 patent, and in Altaras a Cameron (1999) for *E. coli* strains and in Joon-Young et al (2008) for yeast strains. All of these disclosures are herein incorporated by reference.

Preferably, the microorganism producing 1,2-propanediol of the invention is an *Escherichia coli* strain and comprises at least:

- the overexpression of the mgsA or mgsA* gene of SEQ ID NO: 3 or 5 and/or a gene chosen among the genes yqhD or yafB or yahK of SEQ ID NO: 7, 9 or 11 and/or adh gene from *Clostridium beijerinckii* of SEQ ID NO: 13 and/or gldA gene of SEQ ID NO: 15
- the deletion of at least one gene selected from the genes gldA of SEQ ID NO:17, pflAB of SEQ ID NO:19 and 21, adhE of SEQ ID NO:23, IdhA of SEQ ID NO:25, aldA and aldB of SEQ ID NO:27 and 29, edd of SEQ ID NO:31, arcA of SEQ ID NO:33, ndh of SEQ ID NO:35 and frdABCD of SEQ ID NO:37, 39, 41, 43.

The term "improved glycolic acid production" refers to an increased productivity of glycolic acid and/or an increased titer of glycolic acid and/or an increased glycolic acid/carbon source yield and/or an increased purity of glycolic acid compared to its parent strain, i.e. the microorganism prior to the deletion or the attenuation of ppsR gene. The production of glycolic acid by the microorganism in the culture broth can be recorded unambiguously by standard analytical means known by those skilled in the art and in particular with HPLC. Some genetically modified microorganisms with increased glycolic acid production are disclosed in patent applications WO2014162063 and WO2013050659 for yeast strains producing glycolic acid and in WO 2012025780 and WO 2011157728 for *E. coli* strains producing glycolic acid. All of these disclosures are herein incorporated by reference.

Preferably, the microorganism producing glycolic acid of the invention is an *Escherichia coli* strain and comprises at least:

- attenuation of the expression of at least one gene selected from genes aceB of SEQ ID NO:45, glcB of SEQ ID NO:47, gcl of SEQ ID NO:49, eda of SEQ ID NO:51, glcDEFG of SEQ ID NO:53-55-57-59 respectively, aldA of SEQ ID NO:27, icd of SEQ ID NO:61, aceK of SEQ ID NO:63, pta of SEQ ID NO:65, ackA of SEQ ID NO:67, poxB of SEQ ID NO:69, iclR of SEQ ID NO:71 or fadR of SEQ ID NO:73, pgi of SEQ ID NO:75, udhA of SEQ ID NO:77, edd of SEQ ID NO:31, IdhA of SEQ ID NO:25, mgsA of SEQ ID NO:3, arcA of SEQ ID NO:33, glcA of SEQ ID NO:79, lldP of SEQ ID NO:81 and yjcG of SEQ ID NO:83 and/or
- overexpression of aceA of SEQ ID NO:85 and/or ycdW of SEQ ID NO:87.

The term "improved 1,3-propanediol production" refers to an increased productivity of 1,3-propanediol and/or an increased titer of 1,3-propanediol and/or an increased 1,3-propanediol/carbon source yield and/or an increased purity of 1,3-propanediol compared to its parent strain, i.e. the microorganism prior to the deletion or the attenuation of ppsR gene. The production of 1,3-propanediol by the microorganism in the culture broth can be recorded unambiguously by standard analytical means known by those skilled in the art and in particular with GC-MS. Some genetically modified microorganisms with increased 1,3-propanediol production are disclosed in patent applications WO2008052595, WO2010128070 and WO2012062832 for *Clostridium* strains producing 1,3-propanediol and in WO2004033646, WO2010076324, WO2012004247 and WO2016050959 for *E. coli* strains producing 1,3-propanediol. All of these disclosures are herein incorporated by reference.

Preferably, the microorganism producing 1,3-propanediol of the invention is an *Escherichia coli* strain and comprises at least:

- overexpression of at least one gene selected from of yciK of SEQ ID NO:89, btuR of SEQ ID NO:91, ppc of SEQ ID NO:93, galP of SEQ ID NO:95, glk of SEQ ID NO:97, dhaB1 from *Klebsiella pneumoniae* of SEQ ID NO:99, dhaB2 from *Klebsiella pneumoniae* of SEQ ID NO:101, dhaB3 from *Klebsiella pneumoniae* of SEQ ID NO:103, dhaB4 from *Klebsiella pneumoniae* of SEQ ID NO:105, orfX from *Klebsiella pneumoniae* of SEQ ID NO:107, DAR1 from *Saccharomyces cerevisiae* of SEQ ID NO:109, GPP2 from *Saccharomyces cerevisiae* of SEQ ID NO:111 and/or
- attenuation of the expression of at least one gene selected from gapA of SEQ ID NO:113, yqhC of SEQ ID NO:115, glpK of SEQ ID NO:117, gldA of SEQ ID NO:15, mgsA of SEQ ID NO:03, ack of SEQ ID NO:67, pta of SEQ ID NO:65, arcA of SEQ ID NO:33, edd of SEQ ID NO:31, ptsH of SEQ ID NO:119, ptsI of SEQ ID NO:121, crr of SEQ ID NO:123 and ndh of SEQ ID NO:35.

TABLE 1

Enzymes and genes according to the invention

| Name | Micro-organism of origin | Enzyme Function | Gene RefSeq or GenBank reference | Gene SEQ ID NO: | Enzyme Uniprot reference | Protein SEQ ID NO: |
|---|---|---|---|---|---|---|
| PpsR | *Escherichia coli* | bifunctional ADP-dependent kinase-Pi-dependent pyrophosphorylase | NP_416218.1 | 1 | P0A8A4 | 2 |
| MgsA | *Escherichia coli* | methylglyoxal synthase | NP_415483.2 | 3 | P0A731 | 4 |
| MgsA* (H21Q) | n/a | n/a | n/a | 5 | n/a | 6 |
| YqhD | *Escherichia coli* | alcohol dehydrogenase | NP_417484.1 | 7 | Q46856 | 8 |
| YafB | *Escherichia coli* | 2,5-diketo-D-gluconic acid reductase B | NP_414743.1 | 9 | P30863 | 10 |
| YahK | *Escherichia coli* | aldehyde reductase | NP_414859.1 | 11 | P75691 | 12 |
| Adh | *Clostridium beijerinckii* | NADP-dependent isopropanol dehydrogenase | GenBank: AF157307.2 | 13 | P25984 | 14 |
| GldA | *Escherichia coli* | glycerol dehydrogenase | NP_418380.4 | 15 | P0A9S5 | 16 |
| GloA | *Escherichia coli* | lactoyl glutathione lyase | NP_416168.1 | 17 | P0AC81 | 18 |
| PflA | *Escherichia coli* | pyruvate formate lyase activating enzyme | NP_415422.1 | 19 | P0A9N4 | 20 |
| PflB | *Escherichia coli* | pyruvate formate lyase | NP_415423.1 | 21 | P09373 | 22 |
| AdhE | *Escherichia coli* | aldehyde-alcohol dehydrogenase | NP_415757.1 | 23 | P0A9Q7 | 24 |
| LdhA | *Escherichia coli* | D-lactate dehydrogenase | NP_415898.1 | 25 | P52643 | 26 |
| AldA | *Escherichia coli* | lactaldehyde dehydrogenase A | NP_415933.1 | 27 | P25553 | 28 |
| AldB | *Escherichia coli* | aldehyde dehydrogenase B | NP_418045.4 | 29 | P37685 | 30 |
| Edd | *Escherichia coli* | phosphopho gluconate dehydratase | NP_416365.1 | 31 | P0ADF6 | 32 |
| ArcA | *Escherichia coli* | transcriptional dual regulator | NP_418818.1 | 33 | P0A9Q1 | 34 |
| Ndh | *Escherichia coli* | NADH dehydrogenase | NP_415627.1 | 35 | P00393 | 36 |

TABLE 1-continued

Enzymes and genes according to the invention

| Name | Micro-organism of origin | Enzyme Function | Gene RefSeq or GenBank reference | Gene SEQ ID NO: | Enzyme Uniprot reference | Protein SEQ ID NO: |
|---|---|---|---|---|---|---|
| FrdA | *Escherichia coli* | Fumarate reductase flavoprotein subunit | NP_418578.1 | 37 | P00363 | 38 |
| FrdB | *Escherichia coli* | Fumarate reductase iron-sulfur subunit | NP_418577.1 | 39 | P0AC47 | 40 |
| FrdC | *Escherichia coli* | Fumarate reductase subunit C | NP_418576.1 | 41 | P0A8Q0 | 42 |
| FrdD | *Escherichia coli* | Fumarate reductase subunit D | NP_418575.1 | 43 | P0A8Q3 | 44 |
| AceB | *Escherichia coli* | malate synthase | NP_418438.1 | 45 | P08997 | 46 |
| GlcB | *Escherichia coli* | malate synthase | NP_417450.1 | 47 | P37330 | 48 |
| Gcl | *Escherichia coli* | glyoxylate carboligase | NP_415040.1 | 49 | P0AEP7 | 50 |
| Eda | *Escherichia coli* | -keto-3-deoxygluconate 6-phosphate aldolase | NP_416364.1 | 51 | P0A955 | 52 |
| GlcD | *Escherichia coli* | Glycolate oxidase subunit | NP_417453.1 | 53 | P0AEP9 | 54 |
| GlcE | *Escherichia coli* | Glycolate oxidase subunit | YP_026191.1 | 55 | P52073 | 56 |
| GlcF | *Escherichia coli* | Glycolate oxidase 4Fe—4S iron-sulfur cluster subunit | YP_026190.1 | 57 | P52074 | 58 |
| GlcG | *Escherichia coli* | DUF336 family protein | NP_417451.1 | 59 | P0AEQ1 | 60 |
| Icd | *Escherichia coli* | isocitrate dehydrogenase | NP_415654.1 | 61 | P08200 | 62 |
| AceK | *Escherichia coli* | isocitrate dehydrogenase kinase/phosphatase | NP_418440.1 | 63 | P11071 | 64 |
| Pta | *Escherichia coli* | Phosphate acetyltransferase | NP_416800.1 | 65 | P0A9M8 | 66 |
| AckA | *Escherichia coli* | acetate kinase activity | NP_416799.1 | 67 | P0A6A3 | 68 |
| PoxB | *Escherichia coli* | Pyruvate oxidase | NP_415392.1 | 69 | P07003 | 70 |
| IclR | *Escherichia coli* | glyoxylate pathway repressors | NP_418442.2 | 71 | P16528 | 72 |
| FadR | *Escherichia coli* | glyoxylate pathway repressors | NP_415705.1 | 73 | P0A8V6 | 74 |
| Pgi | *Escherichia coli* | phosphoglucose isomerase | NP_418449.1 | 75 | P0A6T1 | 76 |
| UdhA | *Escherichia coli* | pyridine nucleotide transhydrogenase, soluble | NP_416120.1 | 77 | P07001 | 78 |
| GlcA | *Escherichia coli* | glycolate transporter | NP_417449.1 | 79 | Q46839 | 80 |
| LldP | *Escherichia coli* | probable lactate/proton symporter | NP_418060.1 | 81 | P33231 | 82 |
| YjcG | *Escherichia coli* | acetate/glycolate permease | NP_418491.1 | 83 | P32705 | 84 |
| AceA | *Escherichia coli* | isocitrate lyase | NP_418439.1 | 85 | P0A9G6 | 86 |
| YcdW | *Escherichia coli* | NADPH-glyoxylate reductase | NP_415551.2 | 87 | P75913 | 88 |
| YciK | *Escherichia coli* | Uncharacterized oxidoreductase | NP_415787.1 | 89 | P31808 | 90 |
| BtuR | *Escherichia coli* | Cob(I)alamin adenosyltransferase | NP_415786.1 | 91 | P0A9H5 | 92 |
| Ppc | *Escherichia coli* | Phosphoenolpyruvate carboxylase | NP_418391.1 | 93 | P00864 | 94 |
| GalP | *Escherichia coli* | Galactose-proton symporter | NP_417418.1 | 95 | P0AEP1 | 96 |
| GlK | *Escherichia coli* | Glucokinase | NP_416889.1 | 97 | P0A6V8 | 98 |
| DhaB1 | *Klebsiella pneumoniae* | Glycerol dehydratase large subunit | WP_002917676.1 | 99 | Q59476 | 100 |
| DhaB2 | *Klebsiella pneumoniae* | Glycerol dehydratase medium subunit | WP_002917672.1 | 101 | A8CIV5 | 102 |
| DhaB3 | *Klebsiella pneumoniae* | Glycerol dehydratase small subunit | WP_002917670.1 | 103 | Q59475 | 104 |
| DhaB4 | *Klebsiella pneumoniae* | Glycerol dehydratase reactivation factor large subunit | WP_021440745.1 | 105 | Q59474 | 106 |
| OrfX | *Klebsiella pneumoniae* | OrfX | AF282595 | 107 | Q7BK08 | 108 |

TABLE 1-continued

Enzymes and genes according to the invention

| Name | Micro-organism of origin | Enzyme Function | Gene RefSeq or GenBank reference | Gene SEQ ID NO: | Enzyme Uniprot reference | Protein SEQ ID NO: |
|---|---|---|---|---|---|---|
| DAR1 | *Saccharomyces cerevisiae* | Glycerol-3-phosphate dehydrogenase | NP_010262.1 | 109 | Q00055 | 110 |
| GPP2 | *Saccharomyces cerevisiae* | Glycerol-1-phosphate phosphohydrolase | NP_010984.3 | 111 | P40106 | 112 |
| GapA | *Escherichia coli* | Glyceraldehyde-3-phosphate dehydrogenase A | NP_416293.1 | 113 | P0A9B2 | 114 |
| YqhC | *Escherichia coli* | Uncharacterized HTH-type transcriptional regulator YqhC | NP_417483.2 | 115 | Q46855 | 116 |
| GlpK | *Escherichia coli* | Glycerol kinase | NP_418361.1 | 117 | P0A6F3 | 118 |
| PtsH | *Escherichia coli* | Phosphocarrier protein HPr | NP_416910.1 | 119 | P0AA04 | 120 |
| Ptsl | *Escherichia coli* | Phosphoenolpyruvate-protein phosphotransferase | NP_416911.1 | 121 | P08839 | 122 |
| crr | *Escherichia coli* | Glucose-specific phosphotransferase enzyme IIA component | NP_416912.1 | 123 | P69783 | 124 |

(n/a: not available)

As discussed above, sugar is transported into bacterial cells and phosphorylated by the phosphoenolpyruvate: sugar phosphotransferase system (PTS)). Phosphorylated sugar and particularly, phosphorylated glucose is toxic to cells in high concentrations and as a result the PTS system is highly regulated. This, coupled with the fact that the system is complex, makes manipulation of the system very difficult. However, as described below, the inventors have surprisingly produced a genetically modified microorganism comprising functional genes coding for a PTS carbohydrate utilization system while lacking at least one protein regulating PPS expression.

In a second aspect, the present invention thus relates to a genetically modified microorganism for the enhanced production of a molecule of interest from a carbohydrate as source of carbon, said genetically modified microorganism comprising functional genes coding for the PTS carbohydrate utilization system and a decreased expression of the bifunctional ADP-dependent kinase-Pi-dependent pyrophosphorylase protein regulating the expression of the Phosphenolpyruvate synthase (PPS).

This genetically modified microorganism has the same genetic characteristics as those used in the method of the present invention. Particularly, in this microorganism, the gene ppsR coding for the bifunctional ADP-dependent kinase-Pi-dependent pyrophosphorylase DUF229 is deleted or attenuated. More preferentially the gene ppsR is deleted in the microorganism of the invention.

Consequently, it may be used in the fermentative method according to the invention for increasing the production of a molecule of interest, for instance a molecule selected from ethanol, ethylene, ethylene glycol, glycolic acid, propylene, acrylic acid, isopropanol, lactic acid, 1,3-propanediol, 1,2-propanediol, prenol, isobutene, butadiene, butanediol, butanol, isobutanol, methyl ethyl ketone, succinic acid, glutamic acid, isoprene, adipic acid, muconic acid, lysine, dodecanedioic acid, farnesene, and 2,4-dihydroxybutyric acid.

Preferably, said microorganism may be used in the fermentative method according to the invention for increasing production of at least one of compound selected from 1,3-propanediol, 1,2-propanediol, and glycolic acid.

EXAMPLES

Example 1: Methods for Strain Construction

In the examples given below, methods well known in the art were used to construct *E. coli* strains containing replicating vectors and/or various chromosomal deletions, and substitutions using homologous recombination well described by Datsenko & Wanner, (2000) for *E. coli*. In the same manner, the use of plasmids or vectors to express or overexpress one or several genes in a recombinant microorganism are well-known by the man skilled in the art. Examples of suitable *E. coli* expression vectors include pTrc, pACYC184n pBR322, pUC18, pUC19, pKC30, pRep4, pHS1, pHS2, pPLc236, etc . . . .

Several protocols have been used in the following examples. Protocol 1 (chromosomal modifications by homologous recombination, selection of recombinants), protocol 2 (transduction of phage P1) and protocol 3 (antibiotic cassette excision, the resistance genes were removed when necessary) used in this invention have been fully described in patent application EP 2532751. The antibiotic resistant cassette can be amplified on pKD3, pKD4, pKD13 or any other plasmid containing another antibiotic resistant gene surrounded by FRT sites. Chromosomal modifications were verified by PCR analysis with appropriate oligonucleotides that the person skilled in the art is able to design.

Example 2: Construction of Strains 1 to 6

Construction of Strain 1

To express the triose phosphate isomerase encoded by the tpiA gene and to regulate the expression of the glyceraldehyde phosphate dehydrogenase encoded by the gapA gene, the homologous recombination strategy was used (according to Protocols 1 and 3). The tpiA gene was introduced as described in example 3 of patent application WO2008116852 into the evolved strain MG1655 lpd* DtpiA DpflAB DadhE DldhA DgloA DaldA DaldB Dedd DarcA Dndh DfrdABCD described in example 2 of patent application WO2015173247. Then, the genomic modification to regulate the gapA expression “CI857-PRO1/RBS11- gapA" was introduced as described in patent EP2532751 into the previous strain. The gldA*(A160T) gene was cloned into the pME101VB06 plasmid as described in patent application EP2532751. This plasmid was named pPG0078. To allow the growth of *Escherichia coli* on sucrose, the genes scrK, scrYAB and scrR from the plasmid pUR400 (Schmid et al., 1982) were cloned under their natural promoters on the plasmid pBBR1MCS3. This plasmid was named pPG0231.

Finally, plasmids pPG0078 and pPG0231 were transformed into the previous strain, giving rise to strain 1.

Construction of Strain 2

To inactivate the gldA gene, the homologous recombination strategy was used (according to Protocol 1). Oligonucleotides for DgldA: SEQ ID No 125 and 126, were used to amplify the resistance cassette by PCR. The strain retained was designated MG1655 DgldA::Cm. The DgldA::Cm deletion was transferred by P1 phage transduction (according to Protocol 2) into the evolved strain MG1655 lpd* DtpiA DpflAB DadhE DldhA DgloA DaldA DaldB Dedd DarcA Dndh DfrdABCD. The adh gene from *Clostridium beijerinckii* (Hanai et al., 2007) was cloned into the pME101VB01 plasmid described in patent application WO2008/116853. This plasmid was named pPG0468.

Finally, plasmids pPG0231 and pPG0468 were transformed into the previous strain, giving rise to strain 2.

Construction of Strain 3

To inactivate the ptsHI+crr operon, the homologous recombination strategy was used (according to Protocol 1). Oligonucleotides for DptsHIcrr: SEQ ID No 127 and 128, were used to PCR amplify the resistance cassette. The strain retained was designated MG1655 DptsHI+crr::Km. The DptsHI+crr::Km deletion was transferred by P1 phage transduction (according to Protocol 2) into strain 2, giving rise to strain 3.

Construction of Strains 4 and 5

Table 2 below indicates the references of the patent applications describing full protocols for constructing strains 4 and 5.

TABLE 2

Construction of strains 4 and 5

| Strain number | Described in patent |
|---|---|
| Strain 4 | WO2010108909: example 2 |
| Strain 5 | WO2004033646: strain TT pSYCO109 |

Construction of Strain 6

To reconstruct the ptsHI+crr operon, the Km resistance cassette was introduced downstream of the operon using the homologous recombination strategy (according to Protocol 1). Oligonucleotides for ptsHIcrr: SEQ ID No 129 and 130, were used to PCR amplify the resistance cassette. The strain retained was designated MG1655 ptsHI+crr::Km. The ptsHI+crr::Km modification was transferred by P1 phage transduction (according to Protocol 2) into strain 5, giving rise to strain 6.

Example 3: Construction of Strains 7 to 12

To inactivate the PEP synthase regulatory protein PSRP encoded by the ppsR gene, the homologous recombination strategy was used (according to Protocols 1 and 3). Oligonucleotides for DppsR: SEQ ID No 131 and 132, were used to PCR amplify the resistance cassettes. The strains retained were designated MG1655 DppsR::Km or MG1655 DppsR::Gt. Finally, the DppsR::Km or MG1655 DppsR::Gt deletion was transferred by P1 phage transduction (according to Protocol 2) into the strains given in example 2.

TABLE 3

Construction of strains 7 to 12

| DppsR::Km deletion was transferred into | giving rise to |
|---|---|
| Strain 1 | Strain 7 |
| Strain 2 | Strain 8 |
| Strain 3 | Strain 9 |
| Strain 4 | Strain 10 |
| Strain 5 | Strain 11 |
| Strain 6 | Strain 12 |

Construction of Strain 13

To overexpress the phosphoenolpyruvate synthase from *Escherichia coli*, the pJB137-PgapA-ppsA plasmid described in patent application WO2008116853 was transformed into the strain 1, giving rise to strain 13.

Example 4: Shake Flask Cultures and Yields 1,2-propanediol production strains were cultivated in flask cultures as described in patent application EP 2532751, except that either sucrose or glucose or mannose or maltose were used as sugars, as well as 40 g/L MOPS. When necessary 100 μM IPTG were added to the medium. Residual sugars as well as produced 1,2-propanediol (PG) and hydroxacetone (HA) were quantified by HPLC with refractometric detection.

Methods for shake flasks cultures and glycolic acid (AG) quantification were as described in WO2010108909.

Methods for shake flask cultures and 1,3-propanediol (PDO) quantification were as described in WO2004033646.

For all the cultures, when it was necessary, antibiotics were added at a concentration of 50 $mg \cdot L^{-1}$ for kanamycin and spectinomycin, at a concentration of 30 $mg \cdot L^{-1}$ for chloramphenicol and at a concentration of 10 $mg \cdot L^{-1}$ for gentamycin.

TABLE 4

Yields (g product/g consumed sugar) of the strains described above

| Strain | Control strain | Culture conditions | Product | Yield (g product/g consumed sugar) |
|---|---|---|---|---|
| 7 | 1 | Sucrose 37° C. | PG + HA | ++ |
| 7 | 1 | Sucrose 30° C. | PG + HA | + |
| 7 | 1 | Glucose 37° C. | PG + HA | +++ |
| 7 | 1 | Glucose 30° C. | PG + HA | ++ |
| 7 | 1 | Mannose 37° C. | PG + HA | +++ |
| 7 | 1 | Maltose 37° C. | PG + HA | = |
| 13 | 1 | Sucrose 37° C. | PG + HA | = |
| 8 | 2 | Sucrose 37° C. | PG + HA | + |
| 9 | 3 | Sucrose 37° C. | PG + HA | = |
| 10 | 4 | Glucose 37° C. | AG | +++ |
| 11 | 5 | Glucose 37° C. | PDO | = |
| 12 | 6 | Glucose 37° C. | PDO | +++ |

=: no difference with control strain,
+: yield higher than control strain (110%-120%),
++: yield higher than control strain (120%-150%),
+++: yield higher than control strain (>150%)

Strain 7 had better yield than strain 1 in all conditions except with maltose which is not transported by a PTS system. Strain 13 was not different from strain 1 indicating that overexpressing pps is not efficient if ppsR is still expressed. Strains 10 and 12 had better yields than corresponding control strains 4, and 6. Strain 11 was not different from strain 5, compliant with the non-PTS transport system for glucose in this strain.

CONCLUSION

As demonstrated by the above examples, the deletion of ppsR coding for the bifunctional ADP-dependent kinase-Pi-dependent pyrophosphorylase DUF299 protein allows the production of 1,2-propanediol, 1, 3-propanediol and glycolic acid in microorganisms using the PTS system for sugar transport to be increased.

BIBLIOGRAPHY

Altaras N E and Cameron D C (1999), Appl. Environ. Microbiol., 65: 1180-1185
Altschul S, Gish W, Miller W, Myers E, Lipman D J (1990). J. Mol. Biol; 215 (3): 403-410
Anderson, Proc. Natl. Acad. Sci. USA., 1946, 32:120-128.
Burnell J N (2010) BMC Biochemistry 11 (1)
Canovas J L, Kornberg H L (1965). Biochim Biophys Acta 96; 169-72.
Cooper R A, Kornberg H L (1965). Biochim Biophys Acta 104(2); 618-20.
Datsenko K A Et Wanner B L, (2000), Proc Nati Acad Sci USA., 97: 6640-6645
Davis J J Et Olsen G J. (2011). Mol. Biol. Evol.; 28(1):211-221
Deml L, Bojak A, Steck S, Graf M, Wild J, Schirmbeck R, Wolf H, Wagner R. (2011). J. Virol., 75(22): 10991-11001.
Gabor E, Gaiter A K, Kosfeld A, Staab A, Kremling A, Jahreis K. (2011). Eur. J. Cell Biol., 90(9): 711-720
Graf M, Bojak A, Deml L, Bieler K, Wolf H, Wagner R. (2000). J. Virol.; 74(22): 10/22-10826
Gosset G, Yong-Xiao J, Berry A (1996). Journal of Industrial Microbiology 17: 47-52.
Hanai T, Atsumi S, Liao J (2007), Appl. Environ. Microbiol., 73: 7814-7818
Joon-Young J, Choi E S, Oh M K. (2008). J. Microbiol. Biotechnol., 18(11): 1797-1802
Kim P, Laivenieks M, Vieille C, Gregory Zeikus J. (2004). Applied and Environmental Microbiology 70(2):1238-1241.
Kornberg H L, Malcovati M (1973). FEBS Lett 32(2); 257-9.
Kotrba P, Inui M, Yukawa H (2001). J. Bioscience Et Bioeng. 92(6):502-517
Meza E, Becker J, Bolivar F, Gosset G, Wittmann C (2012). Microbial Cell Factories 11: 127.
Miller, 1992; "A Short Course in Bacterial Genetics: A Laboratory Manual and Handbook for *Escherichia coli* and Related Bacteria", Cold Spring Harbor Laboratory Press, Cold Spring Harbor, N.Y.
Patnaik R, Roof W D, Young R F, Liao J C. (1992). Journal of Bacteriology 174(23):7527-7532.
Pittard J, Wallace B J. (1966). Journal of Bacteriology 91(4):1494-1508.
Postma, P. W., Roseman, S. (1976). Biochim Biophys Acta 457(3-4); 213-57.
Sambrook and Russell, (2001), Molecular Cloning: 3rd edition, Cold Spring Harbor Laboratory Press, NY, Vol 1, 2, 3
Schaefer U, Boos W, Takors R, Weuster-Botz D, (1999). Anal. Biochem. 270: 88-96.
Schmid K, Schupfner M, Schmitt R (1982). J. Bacteriol. 151: 68-76
Tatarko M, Romeo T (2001). Current Microbiology 43: 26-32.

The invention claimed is:

1. A method for the production of a molecule of interest by conversion of a source of carbon in a fermentative process comprising the following steps:

culturing a microorganism genetically modified for the production of the molecule of interest in an appropriate culture medium comprising a carbohydrate as source of carbon and recovering the molecule of interest from the culture medium, wherein said genetically modified microorganism comprises functional genes coding for a phosphotransferase carbohydrate utilization system, wherein in said genetically modified microorganism the expression of the bifunctional ADP-dependent kinase-Pi-dependent pyrophosphorylase protein regulating the expression of the phosphoenolpyruvate synthase (PPS) is decreased, wherein the molecule of interest is selected from glycolic acid, lactic acid, 1,3-propanediol, 1,2-propanediol, prenol, isobutene, butadiene, butanediol, methyl ethyl ketone, succinic acid, glutamic acid, adipic acid, muconic acid, lysine, dodecanedioic acid, farnesene, and 2,4-dihydroxybutyric acid, and wherein the carbohydrate is selected from the group consisting of glucose, fructose, mannose, cellobiose, and sucrose, and any combination thereof.

2. The method of claim 1, wherein the functional genes coding for a phosphotransferase carbohydrate utilization system are heterologous to the genetically modified microorganism.

3. The method of claim 1, wherein the functional genes coding for a phosphotransferase carbohydrate utilization system are native to the genetically modified microorganism.

4. The method of claim 1, wherein the native gene coding for the bifunctional ADP-dependent kinase-Pi-dependent pyrophosphorylase protein regulating the expression of the phosphoenolpyruvate synthase (PPS) is attenuated or deleted in said genetically modified microorganism.

5. The method of claim 4, wherein the microorganism is selected among the group consisting of Enterobacteriaceae, Bacillaceae, Clostridiaceae, Streptomycetaceae, Corynebacteriaceae, Saccharomyceteceae and yeasts.

6. The method of claim 5, wherein the microorganism is selected from the group consisting of *Escherichia coli, Klebsiella pneumoniae, Thermoanaerobacterium thermosaccharolyticum, Clostridium sphenoides* and *Saccharomyces cerevisiae.*

7. The method of claim 6, wherein the microorganism is *E. coli Escherichia coli.*

8. The method of claim 7, wherein the gene ppsR coding for the bifunctional ADP-dependent kinase-Pi-dependent pyrophosphorylase DUF299 protein is attenuated or deleted.

9. The method of claim 1, wherein when the molecule of interest is 1,2-propanediol, the genetically modified microorganism comprises:

overexpression of at least one gene selected from the group consisting of mgsA of SEQ ID NO: 3, mgsA* of SEQ ID NO: 5, yqhD of SEQ ID NO: 7, yafB of SEQ ID NO: 9, yahK of SEQ ID NO: 11, adh of SEQ ID NO: 13, gdlA of SEQ ID NO: 15, and deletion of at least one gene selected from the group consisting of gloA of SEQ ID NO: 17, pflAB of SEQ ID NOs: 19 and 21, adhE of SEQ ID NO: 23, ldhA of SEQ ID NO: 25, aldA and aldB of SEQ ID NOs: 27 and 29, edd of SEQ ID NO: 31, arcA of SEQ ID NO: 33, ndh of SEQ ID NO: 35 and frcABCD of SEQ ID NOs: 37, 39, 41, 43.

10. The method of claim 1, wherein when the molecule of interest is glycolic acid, the genetically modified microorganism comprises:

attenuation of the expression of at least one gene selected from the group consisting of aceB of SEQ ID NO: 45, glcB of SEQ ID NO: 47, gcl of SEQ ID NO: 49, eda of SEQ ID NO: 51, glcDEFG of SEQ ID NO:53,55,57,59, aldA of SEQ ID NO:27, icd of SEQ ID NO:61, aceK of SEQ ID NO:63, pta of SEQ ID NO:65, ackA of SEQ ID NO:67, poxB of SEQ ID NO:69, iclR of SEQ ID NO:71 or fadR of SEQ ID NO:73, pgi of SEQ ID NO:75, udhA of SEQ ID NO:77, edd of SEQ ID NO:31, ldhA of SEQ ID NO:25, mgsA of SEQ ID NO:3, arcA of SEQ ID NO:33, glcA of SEQ ID NO:79, lldP of SEQ ID NO:81 and yjcG of SEQ ID NO:83, or overexpression of at least one gene selected from the group consisting of aceA of SEQ ID NO:85 and ycdW of SEQ ID NO:87, or a combination thereof.

11. The method of claim 1, wherein when the molecule of interest is 1,3-propanediol, the genetically modified microorganism comprises:

overexpression of at least one gene selected from the group consisting of yciK of SEQ ID NO:89, btuR of SEQ ID NO:91, ppc of SEQ ID NO:93, galP of SEQ ID NO:95, glk of SEQ ID NO:97, dhaB1 of SEQ ID NO:99, dhaB2 of SEQ ID NO:101, dhaB3 of SEQ ID NO:103, dhaB4 of SEQ ID NO:105, orfX of SEQ ID NO:107, DAR1 of SEQ ID NO:109, and GPP2 of SEQ ID NO:111, or attenuation of the expression of at least one gene selected from the group consisting of gapA of SEQ ID NO:113, yqhC of SEQ ID NO:115, glpK of SEQ ID NO:117, gldA of SEQ ID NO:15, mgsA of SEQ ID NO:03, ack of SEQ ID NO:67, pta of SEQ ID NO:65, arcA of SEQ ID NO:33, edd of SEQ ID NO:31, ptsH of SEQ ID NO:119, ptsI of SEQ ID NO:121, crr of SEQ ID NO:123 and ndh of SEQ ID NO:35, or a combination thereof.

* * * * *